US009649354B2

(12) United States Patent
Panitch et al.

(10) Patent No.: US 9,649,354 B2
(45) Date of Patent: *May 16, 2017

(54) POLYPEPTIDE INHIBITORS OF HSP27 KINASE AND USES THERFOR

(71) Applicant: Purdue Research Foundation, West Lafayette, IN (US)

(72) Inventors: Alyssa Panitch, West Lafayette, IN (US); Brandon Seal, West Lafayette, IN (US); Brian P. Ward, Lebanon, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/280,722

(22) Filed: Sep. 29, 2016

(65) Prior Publication Data

US 2017/0072009 A1 Mar. 16, 2017

Related U.S. Application Data

(62) Division of application No. 13/934,933, filed on Jul. 3, 2013, now Pat. No. 9,493,508, which is a division of application No. 11/972,459, filed on Jan. 10, 2008, now Pat. No. 8,536,303.

(60) Provisional application No. 60/880,137, filed on Jan. 10, 2007.

(51) Int. Cl.
*C07K 7/06* (2006.01)
*A61K 38/16* (2006.01)

(52) U.S. Cl.
CPC .................................. *A61K 38/16* (2013.01)

(58) Field of Classification Search
None
See application file for complete search history.

(56) References Cited

U.S. PATENT DOCUMENTS

| | | | |
|---|---|---|---|
| 4,105,027 A | 8/1978 | Lundquist | |
| 4,192,309 A | 3/1980 | Poulsen | |
| 4,227,522 A | 10/1980 | Carris | |
| 4,627,432 A | 12/1986 | Newell et al. | |
| 4,778,054 A | 10/1988 | Newell et al. | |
| 4,811,731 A | 3/1989 | Newell et al. | |
| 5,035,237 A | 7/1991 | Newell et al. | |
| 5,175,144 A | 12/1992 | Walser | |
| 5,415,864 A | 5/1995 | Kopecek et al. | |
| 5,565,350 A | 10/1996 | Kmiec et al. | |
| 6,855,693 B2 | 2/2005 | Mochly-Rosen et al. | |
| 6,921,527 B2 | 7/2005 | Platz et al. | |
| 7,041,814 B1 | 5/2006 | Weinstock et al. | |
| 7,135,453 B2 | 11/2006 | Brophy et al. | |
| 7,361,352 B2 | 4/2008 | Birkett et al. | |
| 8,536,303 B2 * | 9/2013 | Panitch ................ | C07K 14/001 530/323 |
| 8,741,849 B2 | 6/2014 | Panitch et al. | |
| 9,034,815 B2 | 5/2015 | Panitch | |
| 9,493,508 B2 * | 11/2016 | Panitch ................ | C07K 14/001 |
| 2002/0009491 A1 | 1/2002 | Rothbard et al. | |
| 2002/0041899 A1 | 4/2002 | Chudzik et al. | |
| 2002/0128444 A1 | 9/2002 | Gingras et al. | |
| 2003/0134810 A1 | 7/2003 | Springate et al. | |
| 2003/0187232 A1 | 10/2003 | Hubbell et al. | |
| 2003/0190364 A1 | 10/2003 | Panitch et al. | |
| 2005/0153372 A1 | 7/2005 | Greengard et al. | |
| 2006/0024264 A1 | 2/2006 | Kuroda et al. | |
| 2006/0035814 A1 | 2/2006 | Brophy et al. | |
| 2006/0115453 A1 | 6/2006 | Yaffe et al. | |
| 2006/0293234 A1 | 12/2006 | Schroeder | |
| 2007/0026518 A1 | 2/2007 | Healy et al. | |
| 2007/0078092 A1 | 4/2007 | Livnah et al. | |
| 2007/0154448 A1 | 7/2007 | Reid et al. | |
| 2007/0202189 A1 | 8/2007 | Ahlfors | |
| 2008/0038352 A1 | 2/2008 | Simpson et al. | |
| 2008/0113971 A1 | 5/2008 | Hanau et al. | |
| 2008/0132443 A1 | 6/2008 | Brophy et al. | |
| 2008/0293640 A1 | 11/2008 | Brophy et al. | |
| 2009/0149389 A1 | 6/2009 | Panitch et al. | |
| 2009/0176694 A1 | 7/2009 | Brophy et al. | |
| 2009/0176695 A1 | 7/2009 | Brophy et al. | |
| 2009/0196927 A1 | 8/2009 | Panitch et al. | |
| 2009/0258819 A1 | 10/2009 | Brophy et al. | |
| 2009/0269406 A1 | 10/2009 | Panitch et al. | |
| 2010/0004165 A1 | 1/2010 | Brophy et al. | |
| 2010/0009903 A1 | 1/2010 | Brophy et al. | |
| 2010/0098760 A1 | 4/2010 | Panitch | |
| 2010/0158968 A1 | 6/2010 | Panitch et al. | |
| 2011/0052658 A1 | 3/2011 | Panitch et al. | |
| 2011/0288036 A1 | 11/2011 | Lander et al. | |
| 2012/0263680 A1 | 10/2012 | Lander et al. | |
| 2014/0112947 A1 | 4/2014 | Panitch et al. | |

FOREIGN PATENT DOCUMENTS

| | | |
|---|---|---|
| CA | 2689296 | 7/2008 |
| CN | 1747949 | 3/2006 |

(Continued)

OTHER PUBLICATIONS

Zhongshu Song at al., "Fusarin C biosynthesis in Fusarium moniliforme and Fusarium venenatum," *Chembiochem*, 2004, 5(9): 1196-1203.
Morrison et al., "Combinatorial alanine-scanning," Current Opinion in Chemical Biology, 2001, 5:302-307.
Del Gaizo et al. A Novel TAT-Mitochondrial Signal Sequence Fusion Protein Is Processed, Stays in Mitochondria, and Crosses the Placenta, Molecular Therapy, 2003, 7(6):720-730.
Yu, Pey-Jen et al; "Vascular injury and modulation of MAPKs: A targeted approach to therapy of restenosis." Cell. Signal, (2007) 19 p. 1359-1371.

(Continued)

*Primary Examiner* — Maury Audet
(74) *Attorney, Agent, or Firm* — McCarter & English LLP

(57) ABSTRACT

The present invention provides polypeptide inhibitors of HSP27 kinase, compositions thereof, and methods for using such polypeptides and compositions for various therapeutic uses.

5 Claims, 11 Drawing Sheets

(56) References Cited

FOREIGN PATENT DOCUMENTS

| | | |
|---|---|---|
| JP | 2002-505077 | 2/2002 |
| JP | 2006-515159 | 2/2004 |
| WO | WO 91/16038 | 10/1991 |
| WO | WO 93/22443 | 11/1993 |
| WO | WO02/083933 | 10/2002 |
| WO | WO 03/018758 | 3/2003 |
| WO | WO03/076333 | 9/2003 |
| WO | WO 2004/075914 | 9/2004 |
| WO | WO 2004/110337 | 12/2004 |
| WO | WO 2005/037236 | 4/2005 |
| WO | WO 2005/114221 | 12/2005 |
| WO | 2006/053315 | 5/2006 |
| WO | 2006071458 | 7/2006 |
| WO | WO 2006/071456 | 7/2006 |
| WO | WO 2007/053512 | 5/2007 |
| WO | WO 2008/008772 | 1/2008 |
| WO | WO 2008/085191 | 7/2008 |
| WO | WO 2009/021137 | 2/2009 |
| WO | WO 2009/123759 | 10/2009 |
| WO | WO 2010/065206 | 6/2010 |
| WO | WO 2010/068692 | 6/2010 |
| WO | WO 2011/017132 | 2/2011 |

OTHER PUBLICATIONS

Tucker, Erik I. et al; "Prevention of vascular graft occlusion and thrombus-associated thrombin generation by inhibition of factor XI." Blood (2009) 113(4) p. 936-944.
Babapulle, Mohan N. et al; "A hierarchial bayesian meta analysis of randomized clinical trials of drug eluting stents." Lancet (2004) 364 p. 583-591.
Cyrus, Tillmann et al; "Effect of low dose aspirin on vascular inflammation, plaque stability, and atherogenesis in low density lipoprotein receptor deficient mice." Circulation (2002) 106 p. 1282-1287.
Dinarello, C. A.; "The IL-1 family and inflammatory diseases." Clin. Exp. Rheumatol. (2002) 20 (suppl. 27) p. S1-S13.
Tourneau Christophe Le et al; "Dose escalation methods in phase I cancer clinical trials." J. Natl. Cancer. Inst (2009) 101 (10) p. 708-720, publication date May 20, 2009.
Schneider et al., 1998, In Vivo Evaluation of hsp27 as an Inhibitor of Actin Polymerization: Hsp27 Limits Actin Stress Fiber and Focal Adhesion Formation After Heat Shock, Journal of Cellular Physiology, 177: 575-584.
Beck et al., 2000, Molecular chaperones in the kidney: distribution, putative roles, and regulation, Am J Physiol Renal Physiol, 279: 203-215.
Keezer et al., Angiogenesis Inhibitors Target the Endothelial Cell Cytoskeleton through Altered Regulation of Heat Shock Protein 27 and Cofilin, Cancer Res, 63: 6405-6412.
Abergel et al, "Biochemical composition of the connective tissue in keloids and analysis of collagen metabolism in keloid fibroblast cultures," J Invest Dermatol, vol. 84, pp. 384-390, May 1985.
Achari et al., 1997, J Polym Sci A: Polym Chem, 35: 2513-2520.
Allaire at al. (1997) Ann Thorac Surg 63(2):582-91.
Altschul et al., Nucleic Acids Res. 25:3389-3402 (1997).
Amano et al., "Formation of Actin Stress Fibers and Focal Adhesions Enhanced by RhoKinase", Science, Feb. 28, 1997, vol. 275, No. 5304, 1308-1311.
Andrew et al., "Spinothalamic lamina I neurons selectively sensitive to histamine: a central neural pathway for itch," Nature Neuroscience, 2001.4(1): p. 72-77.
Andrews et al. (1993). "Report of the AVMA panel on Euthanasia" Journal of the American Veterinary Association, 202(2): 229-249.
Auwerx, "The Human Leukemia-Cell Line, Thp-1-a Multifaceted Model for the Study of Monocyte-Macrophage Differentiation," Experientia, 1991, 47, (1), 22-31.
Bareyre et al., "Inflammation, degeneration and regeneration in the injured spinal cord: insights from DNA microarrays," Trends Neurosci, 2003, 26(10): p. 555-563.

Beutler, 1999; J. Rheumatol., 26:16-21.
Biomol International (online), Kinase Inhibitors. 2006, retrieved from http://www.biomol.com/Online_Catalog/Online_Catalog/Products/36/?search=&mode=product&lastSort=&all=true&categoryId=714.
Biomol International (online), Kinases. 2006, retrieved from http://www.biomol.com/Online_Catalog/Online_Catalog/Products/36/?search=&mode=product&lastSort=&all=true&categoryld=713.
Brennan et al., "Expression in Chronic Inflammatory Disease," British Medical Bulletin, 1995, 51(2), 368-384.
Brophy et al. (1998) J Reprod Fertil 114(2):351-355.
Buckenmaier, C.C., 3$^{rd}$, et al., "Comparison of antiadhesive treatments using an objective rat model," Am. Surg., 1999, 65(3): 274-82.
Butler et al., "Use of organotypic coculture to study keloid biology," Am J Surg, 195(2): 144-148, Feb. 2008.
Calderon et al., "Increased proliferation in keloid fibroblasts wounded in vitro," J Surg Res, vol. 61, pp. 343-347, Mar. 1996.
Carpino et al., 1972, J. Org. Chem., 37: 3403-3409.
Davies et al. (2000) Biochem J 351(Pt 1):95-105.
DeGrado et al. (1999) Annual Review of Biochemistry 68:779-819.
DeMarzo et al., "Prostate stem cell compartments: expression of the cell cycle inhibitor p27Kip1 in normal, hyperplastic, and neoplastic cells", Am. J. Pathol., Sep. 1998, vol, 153, No. 3, 911-919.
Dreiza et al., "Transducible heat shock protein 20 phosphopeptide alters cytoskeletal dynamics," FASEB J. 19. 261-263: 2004.
Dreiza et al. (2005) FASEB J 19(2):261-3.
Duncan et al. (1999) FASEB J 13(13): 1774-86.
Fawell et al., Proc Nail Acad Sci USA, 1994, 91(2): 664-668.
Feldmann et al., "Role of cytokines in rheumatoid arthritis," Annual Review of Immunology, 1996, 14, 397-440.
Feldmann et al., "The role of cytokines in the pathogenesis of rheumatoid arthritis," Rheumatology, 1999, 38, 3-7.
Fields et al., 1990, Int. J. Pept. Protein Res., 35: 161-214.
Firestein et al., "How important are T cells in chronic rheumatoid synovitis? II. T cell-independent mechanisms from beginning to end," Arthritis and Rheumatism 2002, 46, (2), 298-308.
Fisher et al., 1994, Macromol Chem Phys, 195: 679-687.
Fragonas et al., Aricular cartilage repair in rabbits by using suspensions of allogenic chondrocytes in alginate, Biomaterials, 2000, 21(8):795-801.
Frankel et al., Cell, 55(6): 1189-1193, 1988.
Fuchs et al. (1997) J Hypertens 15(3): 301-307.
Fuchs et al. (2000) Am J Physiol Regul Integr Comp Physiol 279(2): R492-8.
Gaestel et al., "Protein kinases as small molecule inhibitor targets in inflammation," Current Medicinal Chemistry, 2007, 14 (21): 2214-2234.
Gaestel, Nat. Rev. Mol. Cell. Biol. 7, 120-130, 2006.
Gerthoffer et al. (2001) J Appl Physiol 91:963-972, 2001.
Green et al., Cell, 1988, 55(60: 1179-1188.
Gu et al., 2002, J Appl Poly Sci, 86: 3412-3419.
Haapasalo et al., "Truncated trkB.T1 is dominant negative inhibitor of trkB.TK+-mediated cell survival", Biochem Biophys Res Commun, Feb. 9, 2001, vol. 280, No. 5, 1352-1358 (Abstract only).
Hanasono at al., "Autocrine growth factor production by fetal, keloid, and normal dermal fibroblasts," Arch Facial Plast Surg, vol. 5, pp. 26-30, Jan.-Feb. 2003.
Hayess at al., "Effect of protein kinase inhibitors on activity of mammalian small heat-shock protein (HSP25) kinase", *Biochemical Pharmacology*, May 9, 1997, vol. 53, No. 9, 1239-1247.
Hedges et al., J Biol. Chem. 274, 24211-24219, 1999.
Hegen et al., "MAPKAP kinase 2-deficient mice are resistant to collagen-induced arthritis," Journal of Immunology 2006, 177(3), 1913-1917.
Henikoff et al. (1989) Proc. Natl. Acad. Sci. USA 89:10915).
Higgins et al., CABIOS, 5:151-153 (1989).
Higgins et al., Gene, 73:237-244 (1988).
Hirano et al., Journal of Surgical Research 102, 77-84, 2002.
Ho et al., "Synthetic Protein Transduction Domains: Enhanced Transduction Potential in Vitro and in Vivo," *Cancer Research*, 2001, 61: 474-477.

(56) References Cited

OTHER PUBLICATIONS

Hong et al., "Growth of keloid-producing fibroblasts in commercially available serum-free media," Otolaryngol Head Neck Surg, vol. 121, pp. 469-73, Oct. 1999.
Hruby, V. J. (2002) Nat Rev Drug Discov 1(11): 847-58.
Huang, et al., Computer Applications in the Biosciences 8:155-65 (1992).
Iwasaki et al., "Effect of transforming growth factor beta 1 on spinal motor neurons after axotomy," J Neurol Sci, 1997, 147(1): 9-12.
Jacovella, Long-lasting results with hydroxylapatide (Radiesse) facial filler, Plastic and Reconstructive Surgery, 2006, 118(3S):15S-21S.
Jenkins et al., "The pathogenesis of rheumatoid arthritis: A guide to therapy," American Journal of the Medical Sciences, 2002, 323(4), 171-180.
Jobanputra et al., Colorectal Dis. Oct. 2007; 9 Suppl 2: 54-9.
Johnson et al. (2004) Nature Biotech 22(9):1093-1094.
Karlin et al., Proc. Natl. Acad. Sci. USA 90:5873-5787 (1993).
Kent et al. (2004) Ann Vasc Surg 18(2): 135-7.
Knoepp et al. (2000) J Vasc Surg 31:343-353.
Koch et al., "Serum-free keloid fibroblast cell culture: an in vitro model for the study of aberrant wound healing," in Plast Reconstr Surg., vol. 99, 1997, pp. 1094-1098.
Koonin et al., "Origin and evolution of eukaryotic apoptosis: the bacterial connection", Cell Death Differ, Apr. 2002, vol. 9, No. 4, 394-404.
Kossi et al., "Different metabolism of hexose sugars and sucrose in wound fluid and in. fibroblast cultures derived from granulation tissue, hypertrophic scar and keloid," Pathobiology; vol. 68, pp. 29-35, Jan.-Feb. 2000.
Kotlyarov et al., "MAPKAP kinase 2 is essential for LPS-induced TNF-alpha biosynthesis," Nature Cell Biology, 1999, 1(2): 94-97.
Kumar et al., "p38 map kinases: Key signaling molecules as therapeutic targets for inflammatory diseases," Nature Reviews Drug Discovery, 2003, 2, (9), 717-726.
Kwon et al., "The cdk2 Binding Domain of p27Kip Correlates with the Inhibition of the Kinase Activity of cdk2/Cyclin Complexes", Biochem Biophys Res Comm, 1996, vol. 220, 703-709.
Langer, 1990 Science 249, 1527-1533.
Lavoie et al., J Biol. Chem. 268, 24210-24214, 1993.
Lavoie et al., Mol Cell Biol. 15: 505-516, 1995.
Liu et al., De novo design, synthesis, and characterization of antimicrobial beta-peptides, J Am Chem Soc, 2001, 123(31): 7553-7559.
LoGerfo et al. (1984) Arch Surg 119:1212-1214.
Lopes et al., "Inhibition of HSP27 phosphorylation by a cell-permeant MAPKAP Kinase 2 inhibitor", *Biochemical and Biophysical Research Communcations*, May 8, 2009, vol. 382, No. 3, 535-539.
Macomson et al. (2002) Neurosurgery 51(1): 204-10; discussion 210-1.
Mann et al. (1999) Lancet 354(9189): 1493-8.
Marijnissen et al., Tissue-engineered cartilage using serially passaged articular chondrocytes. Chondrocytes in alginate, combined in vivo with a synthetic (E210) or biologic degradable carrier (DBM), Biomaterials, 2000.
Matsuoka et al., "Ultrastructural characteristics of keloid fibroblasts," Am J Dermatopathol, vol. 10, pp. 505-508, Dec. 1988.
McCormack et al., "The effect of copper tripertide and tretinoin on growth factor production in a serum-free fibroblast model," Arch Facial Plast Surg, vol. 3, pp. 28-32, Jan.-Mar. 2001.
McLemore et al. (2005) J Am Coll Surg 201(1): 30-6.
Merrifield, 1963, J. Am. Chem. Soc., 85: 2149-2154.
Meyers et al., Computer Applic. Biol. Sci., 4:11-17 (1988).
Mosse et al. (1985) Lab Invest 53(5): 556-62.
Needleman et al., J. Mol. Biol., 48: 443 (1970).
Neidigh et al. (2002) Nature Structural Biology 9(6): 425-430.
Pearson et al., Methods in Molecular Biology, 24: 307-331 (1994).
Pearson et al., Proc. Natl. Acad. Sci., 85: 2444 (1988).

Pincus et al., "What Is the Natural-History of Rheumatoid-Arthritis," Rheumatic Disease Clinics of North America, 1993, 19, (1), 123-151.
Pineau et al., Proinflaminatory cytokine synthesis in the injured mouse spinal cord: multiphasic expression pattern and identification of the cell types involved,: J Comp Neurol, 2007, 500(2): p. 267-285.
Pinol et al., "Effect of minoxidil on DNA synthesis in cultured fibroblasts from healthy skin or keloids," Med Cutan Ibero Lat Am, vol. 18, pp. 13-17, 1990.
Podolin et al., "Attenuation of murine collagen-induced arthritis by a novel, potent, selective small molecule inhibitor of I kappa B kinase 2, TPCA-1 (2-[(aminocarbonyl)amino]-5-(4-fluorophenyl)-3-thiophenecarboxamide), occurs via reduction of proinflammatory cytokines and antigen-induced T cell proliferation," Journal of Pharmacology and Experimental Therapeutics, 2005, 312, (1), 373-381.
Polo et al., "Effect of TGF-beta2 on proliferative scar fibroblast cell kinetics," Ann Plast Surg, vol. 43, pp. 185-90, Aug. 1999.
Powell et al. (2003) Molecular and Cellular Biology, 23(15) 5376-5387.
Ridley et al., "Actions of 11-1 are Selectively Controlled by P38 Mitogen-Activated Protein Kinase: regulation of prostaglandin H synthase-2, metalloproteinases, and IL-6 at different levels", *J. Immonol.*, 1997, vol. 158, 3165.
Ross et al., "High-content screening analysis of the p38 pathway: Profiling of structurally related p38 alpha kinase inhibitors using cell-based assays," Assay and Drug Development Technologies, 2006, 4, (4), 397-409.
Russel et al., "The effect of histamine on the growth of cultured fibroblasts isolated from normal and keloid tissue," J Cell Physiol, vol. 93, pp. 389-393, Dec. 1977.
Sahara et al., "Suppression of in vitro proliferative scar fibroblast contraction by interferon alfa-2b," Wound Repair Regen, vol. 1, pp. 22-27, Jan. 1993.
Saklatvala, "The p38 MAP kinase pathway as a therapeutic target in inflammatory disease," Current Opinion in Pharmacology, 2004, 4, (4), 372-377.
Sawhney et al., Macromolecules (1993) 26, 581-587.
Schenk et al., Signal perception and transduction: the role of protein kinases, *Biochemica et Biophyica Acta*, 1999, vol. 1449, 1-24.
Schwarze et al., Science, 1999, 285(54339: 1569-1572.
Seal et al., Biomacromolecules, 2003, 4: 1572-1582.
Sestier et al., "In vitro toxicity of magnetic fluids evaluated for macrophage cell lines," Journal of Magnetism and Magnetic Materials, 2002, 252, (1-3), 403-405.
Shi et al. (2002) Biol Chem 383:1519-1536 , 2002.
Silver et al., "Regeneration beyond the glial scar," Nature Reviews Neuroscience, 2004. 5(2): p. 146-156.
Smith and Waterman, Adv. Appl. Math., 2: 482 (1981).
Sousa et al. (2007) J Cell Biochem 100(6):1581-1592.
Stokoe, Biochem. J., 1993, 296 (Pt 3): 843-849.
Takemura et al., "Evaluation of a human monocytic cell line THP-1 model for assay of the intracellular activities of antimicrobial agents against Legionella pneumophila," Journal of Antimicrobial.
Tanaka et al., 1976, Bulletin of the Chemical Society of Japan, 49(10): 2821-2823.
Tang et al., Synthesis of urea oligomers and their antibacterial activity, Chem Commun, 2005, 1537-1539.
Terashima et al. (2002) J Am Coil Cardiol 39:228A.
Tessier et al. (2004) J Vasc Surg 40(1): 106-14.
Tew et al., De novo design of biomimetic antimicrobial polymers, PNAS, 2002, 99(8): 5110-5114.
Tapash et al., Transdermal and Topical Drug Delivery, pp. 249-297 (1997).
Tyagi et al., J Biol Chem., 2001, 276(5): 3254-3261.
Vassalli, 1992, Annu. Rev. Immunol., 10:411-452.
Verlardo et al., "Patterns of Gene Expression Reveal a Temporally Orchestrated Wound Healing Response in the Injured Spinal Cord," J. Neurosci.: 2004. 24(39): p. 8562-8576.
Vincent et al., "Human Skin Keloid Fibroblasts Display Bioenergetics of Cancer Cells," J Invest Dermatol, 128(3): 702-709, Mar. 2008.

(56) References Cited

OTHER PUBLICATIONS

Violette et al., Mimicking helical antibacterial peptides with nonpeptidic folding oligomers, Chemistry and Biology, 2006, 13(5): 531-538.
Wang et al., "Construction of animal models of keloid by tissue engineering," Di Yi Jun Yi Da Xue Xue Bao, vol. 25, pp. 815-819, 832, Jul. 2005.
Wang et al., "p27Kip1 overexpression causes apoptotic death in mammalian cells", Oncogene, Dec. 11, 1997, vol. 15, No. 24, 2991-2997.
Ward et al., "Design of a bioactive cell-penetrating peptide: when a transduction domain does more than transduce", *Journal of Peptide Science*, Oct. 2009, vol. 15, No. 10, 668-674.
Weibel et al., Am. J. Surg. 1973; 126: 345-53.
Woerly et al. (2001). "Spinal cord reconstruction using Neurogel™ Implants and functional recovery after chronic injury." Journal of Neuroscience Research, 66: 1187-1197.
Wooten et al., Comput. Chem., 17: 149-163 (1993).
Worm et al., "Aberrant p27Kip1 promoter methylation in malignant melanoma", Oncogene, Oct. 19, 2000, vol. 19, No. 44, 5111-5115.
Xia et al., "Increased CCN2 transcription in keloid fibroblasts requires cooperativity between AP-1 and SMAD binding sites," Ann Surg, vol. 246, pp. 886-895, Nov. 2007.
Xia et al., "P38 MAP kinase mediates transforming growth factor-beta2 transcription in human keloid fibroblasts," Am J Physiol Regul Integr Comp Physiol, vol. 290, pp. R501-508, Mar. 2006.
Xu et al., Oncogene 25, 2987-2998, 2006.
Yamanishi et al., "Regulation of joint destruction and inflammation by p53 in collagen-induced arthritis," American Journal of Pathology 2002, 160, (1), 123-130.
Yamboliev et al., Am. J Physiol. Heart Circ Physiol., 278, H1899-1907, 2000.
Yang et al., "Establishment of an animal model of human hyperplastic scar in nude mice," Zhonghua Shao Shang Za Zhi, vol. 20, pp. 82-4, Apr. 2004.
Yang et al., "Early expression and cellular localization of proinflammatory cytokines interleukin-I beta, interleukin-6, and tumor necrosis factor-alpha in human traumatic spinal cord injury," Spine, 2004.
Zong, X., et al., "Prevention of postsurgery-induced abdominal adhesions by electrospun bioabsorable nanofibrous poly(lactide-co-clucolide)-based membranes," Am. Surg., 2004, 240(5): p. 910-915.
Colomer, Sub-Cellular Biochemistry, 2007, 45: 169-214.
Barone et al., "Inhibition of p38Mitogen-Activated Protein Kinase Provides Neuroprotection in Cerebral Focal Ischemia", Med Res. Rev., 2001, vol. 21, No. 2, 129-145.
Schindler et al., Examination of the kinetic mechanism of mitogen-activated protein kinase activated protein kinase-2, Biochimica et Biophysica Acta, Jul. 29, 2002, 1598(1-2): 88-97.
Burgess et al., J of Cell Bio., 1990, 111: 2129-2138.
Bowie et al., Science, 1990, 247: 1306-1310.
Pawson et al., Science, 2003, 300: 445-452.
Carroll et al., "Heparin stimulates production of bFGF and TGF-beta 1 by human normal, keloid, and fetal dermal fibroblasts," Med Sci Monit, vol. 9, pp. BR97-108, Mar. 2003.
Carroll et al., "Triamcinolone stimulates bFGF production and inhibits TGF-beta 1 production by human dermal fibroblasts," Dermato Surg, vol. 28, pp. 704-709, Aug. 2002.
Chiu et al., "Photodynamic therapy on keloid fibroblasts in tissue-engineered keratinocyte-fibroblast co-culture," Lasers Surg Med, vol. 37, pp. 231-44, Sep. 2005.
Choi, et al., 2005, Angewandte Chemie, 44(41): 6685-6689.
Claverie et al., Comput. Chem., 17:191-201 (1993).
Clowes et al. (1991) J Vasc Surg, 13(6):885-91.
Corpet, et al., Nucleic Acids Research, 16:10881-90 (1988).
Coumans et al. (2001). "Axonal regeneration and functional recovery after complete spinal cord transection in rats by delayed treatment with transplants and neurotrophins." The Journal of Neuroscience, 21(23): 9334-9344.
Dalkowski et al., "Cryotherapy modifies synthetic activity and differentiation of keloidal fibroblasts in vitro," Exp Dermatol, vol. 12, pp. 673-81, Oct. 2003.

\* cited by examiner

POLYPEPTIDE INHIBITORS OF HSP27 KINASE AND USES THERFOR

CROSS REFERENCE TO RELATED APPLICATIONS

This application is a divisional application of U.S. patent application Ser. No. 13/934,933, filed Jul. 3, 2013, which is a divisional application of U.S. patent application Ser. No. 11/972,459, filed Jan. 10, 2008, which issued as U.S. Pat. No. 8,536,303 and claims priority to U.S. provisional patent application Ser. No. 60/880,137, filed Jan. 10, 2007, the contents of which are incorporated by reference herein in their entirety.

STATEMENT OF GOVERNMENT FUNDING

This invention was made with Government support under Grant Number K25 HL074968 awarded by the National Institutes of Health. The Government has certain rights in the invention.

FIELD OF THE INVENTION

The invention is in the fields of cell and molecular biology, polypeptides, drug discovery, and therapeutic methods of use.

SUMMARY OF THE INVENTION

The present invention provides polypeptide inhibitors of HSP27 kinase, compositions thereof, and methods for using such polypeptides and compositions for various therapeutic uses.

In one embodiment, the present invention provides a polypeptide comprising or consisting of a sequence according to general formula I:

Z1-X1-X2-X3-X4X5-X6-X7-X8-X9-X10-Z2 (SEQ ID NO: 69)

wherein Z1 and Z2 are independently absent or are transduction domains;

XI is selected from the group consisting of A, KA, KKA, KKKA (SEQ ID NO: 70), and RA, or is absent;

X2 is selected from the group consisting of G, L, A, V, I, M, Y, W, and F, or is an aliphatic amino acid;

X3 is selected from the group consisting of V, L, I, A, G, Q, N, S, T, and C, or is an aliphatic amino acid;

X4 is selected from the group consisting of Q, N, H, R and K;

X5 is selected from the group consisting of Q and N;

X6 is selected from the group consisting of C, A, G, L, V, I, M, Y, W, and F or is an aliphatic amino acid;

X7 is selected from the group consisting of S, A, C, T, and G or is an aliphatic amino acid;

X8 is selected from the group consisting of V, L, I, and M;

X9 is absent or is any amino acid; and

X10 is absent or is any amino acid;

wherein at least one of the following is true:
 (a) X3 is N and X7 is not G;
 (b) X7 is G and X3 is not N;
 (c) X2 is not L;
 (d) X4 is not R;
 (e) X5 is not Q;
 (f) X6 is not L;
 (g) X8 is not V;
 (h) XI0 is absent; or
 (i) X9 and XI0 are absent.

In another embodiment of the isolated polypeptide according to general formula I, X4 is R, X5 is Q and X8 is V (SEQ ID NO: 71). In another embodiment, the polypeptide comprises KAFAKLAARLYRKALARQLGVAA (SEQ ID NO: 48). In another embodiment, the polypeptide comprises FAKLAARLYRKALARQLGVAA (SEQ ID NO: 49). In another embodiment, the invention includes variants of SEQ ID NO: 48 that are at least 90% identical to SEQ ID NO: 48 and inhibit TNF-α excretion. In another embodiment, the invention includes variants of SEQ ID NO: 49 that are at least 90% identical to SEQ ID NO: 49 and inhibit TNF-α excretion.

The present invention further provides compositions comprising one or more isolated polypeptides comprising a sequence according to general formula I and a pharmaceutically acceptable carrier. In one embodiment, the composition comprises the isolated polypeptide KAFAKLAARLYRKALARQLGVAA (SEQ ID NO: 48) and a pharmaceutically acceptable carrier. In another embodiment, the composition comprises the isolated polypeptide FAKLAARLYRKALARQLGVAA (SEQ ID NO: 49) and a pharmaceutically acceptable carrier. In another embodiment, the composition comprises variants of SEQ ID NO: 48 that are at least 90% identical to SEQ ID NO: 48 and inhibit TNF-α excretion and a pharmaceutically acceptable carrier. In another embodiment, the composition comprises variants of SEQ ID NO: 49 that are at least 90% identical to SEQ ID NO: 49 and inhibit TNF-α excretion and a pharmaceutically acceptable carrier.

The invention also provides an isolated nucleic acid sequence encoding one or more isolated polypeptides comprising a sequence according to general formula I. In one embodiment, the isolated nucleic acid encodes the isolated polypeptide KAFAKLAARLYRKALARQLGVAA (SEQ ID NO: 48). In another embodiment, the isolated nucleic acid encodes the isolated polypeptide FAKLAARLYRKALARQLGVAA (SEQ ID NO: 49). In another embodiment, the isolated nucleic acid encodes variants of SEQ ID NO: 48 that are at least 90% identical to SEQ ID NO: 48 and inhibit TNF-α excretion. In another embodiment, the isolated nucleic acid encodes variants of SEQ ID NO: 49 that are at least 90% identical to SEQ ID NO: 49 and inhibit TNF-α excretion. The present invention also provides recombination expression vectors comprising these nucleic acids and a host cell transfected with the recombinant expression vectors.

The present invention further provides a biomedical device comprising one or more isolated polypeptides comprising a sequence according to general formula 1, wherein the one or more isolated polypeptides are disposed on or in the device. In one embodiment, the biomedical device comprises the polypeptide of SEQ ID NO: 48. In another embodiment, the biomedical device comprises the polypeptide of SEQ ID NO: 49. In another embodiment, the biomedical device comprises variants of SEQ ID NO: 48 that are at least 90% identical to SEQ ID NO: 48 and inhibit TNF-α excretion. In another embodiment, the biomedical device comprises variants of SEQ ID NO: 49 that are at east 90% identical to SEQ ID NO: 49 and inhibit TNF-α excretion.

The present invention further provides a biomedical device comprising one or more isolated polypeptides comprising a sequence according to general formula 1, where the one or more isolated polypeptides are disposed in a matrix disposed on the device. In one embodiment, the biomedical device comprises the polypeptide of SEQ ID NO: 48. In another embodiment, the biomedical device comprises the polypeptide of SEQ ID NO: 49. In another embodiment, the biomedical device comprises variants of SEQ ID NO: 48 that are at least 90% identical to SEQ ID NO: 48 and inhibit TNF-α excretion. In another embodiment, the biomedical device comprises variants of SEQ ID NO: 49 that are at least 90% identical to SEQ ID NO: 49 and inhibit TNF-α excretion. In some embodiments, the matrix is a heparin coating.

The present invention moreover provides a method for treating an inflammatory disease, disorder or condition in a subject in need thereof, the method comprising the step of (a) administering a therapeutically effective amount of a composition of the invention. In one embodiment, the inflammatory disease, disorder, or condition is selected from the group consisting of hyperplastic scarring, keloids, rheumatoid arthritis, chronic obstructive pulmonary disease, atherosclerosis, intimal hyperplasia, Crohn's disease, inflammatory bowel disease, osteoarthritis, Lupus, tendonitis, psoriasis, gliosis, inflammation, type II diabetes mellitus, type I diabetes mellitus, Alzheimer's disease, and adhesions. In another embodiment, the disease, disorder or condition is hyperplastic scarring. In another embodiment, the disease, disorder or condition is rheumatoid arthritis. In another embodiment, the disease, disorder or condition is chronic obstructive pulmonary disease. In another embodiment, the disease, disorder or condition is atherosclerosis. In another embodiment, the disease, disorder or condition is intimal hyperplasia. In another embodiment, the disease, disorder or condition is Crohn's disease. In another embodiment, the disease, disorder or condition is inflammatory bowel disease. In another embodiment, the disease, disorder or condition is osteoarthritis. In another embodiment, the disease, disorder or condition is tendonitis. In another embodiment, the disease, disorder or condition is psoriasis. In another embodiment, the disease, disorder or condition comprises glial scarring. In another embodiment, the disease, disorder or condition is a traumatic brain injury. In another embodiment, the disease, disorder or condition is a spinal cord injury. In another embodiment, the method further comprises the steps of (b) monitoring a level of at least one biomarker in a target tissue, wherein the at least one biomarker is selected from the group consisting of: TGFβ1 expression; collagen I expression; CTGF expression; α-smooth muscle actin expression; TNF-α; IL-1; IL-6; IL-8; COX-2; MIP-1α; and MIP-2; and (c) maintaining the level of the biomarker in the target tissue substantially at normal levels during treatment.

BRIEF DESCRIPTION OF THE FIGURES

FIG. 5 also discloses "KKKALNRQLGVAA" as SEQ ID NO: 72.

DETAILED DESCRIPTION OF THE INVENTION

Figure 1A:
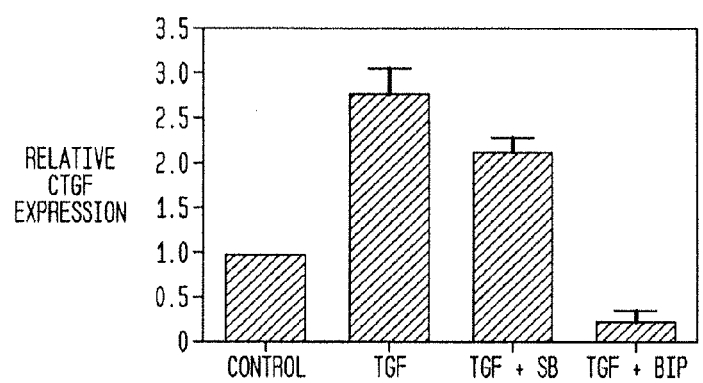
FIG. 1: Data graph showing that HSP27 kinase inhibitor peptide (BIP) inhibits TGF-β1 induced expression of CTGF (FIG. 1A) and collagen (FIG. 1B) in human keloid fibroblasts.

Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique*, 2$^{nd}$ Ed. (R. I. Freshney. 1987. Liss, Inc. New York, N.Y.), and *Gene Transfer and Expression Protocols*, pp. 109-128, ed. E. J. Murray, The Humana Press Inc., Clifton, N.J.).

The single letter designation for amino acids is used predominately herein. As is well known by one of skill in the art, such single letter designations are as follows: A is alanine; C is cysteine; D is aspartic acid; E is glutamic acid; F is phenylalanine; G is glycine; H is histidine; I is isoleucine; K is lysine; L is leucine; M is methionine; N is asparagine; P is proline; Q is glutamine; R is arginine; S is serine; T is threonine; V is valine; W is tryptophan; and Y is tyrosine.

As used herein, the singular forms "a", "an" and "the" include plural referents unless the context clearly dictates otherwise. For example, reference to a "polypeptide" means one or more polypeptides.

In a first aspect, the present invention provides a polypeptide comprising or consisting of a sequence according to general formula I:

Z1-X1-X2-X3-X4X5-X6-X7-X8-X9-X10-Z2    (SEQ ID NO: 69)

wherein Z1 and Z2 are independently absent or are transduction domains;

XI is selected from the group consisting of A, KA, KKA, KKKA (SEQ ID NO: 70), and RA, or is absent;

X2 is selected from the group consisting of G, L, A, V, I, M, Y, W, and F, or is an aliphatic amino acid;

X3 is selected from the group consisting of V, L, I, A, G, Q, N, S, T, and C, or is an aliphatic amino acid;

X4 is selected from the group consisting of Q, N, H, R and K;

X5 is selected from the group consisting of Q and N;

X6 is selected from the group consisting of C, A, G, L, V, I, M, Y, W, and F or is an aliphatic amino acid;

X7 is selected from the group consisting of S, A, C, T, and G or is an aliphatic amino acid;

X8 is selected from the group consisting of V, L, I, and M;

X9 is absent or is any amino acid; and

XI0 is absent or is any amino acid;

wherein at least one of the following is true;
(a) X3 is N and X7 is not G;
(b) X7 is G and X3 is not N;
(c) X2 is not L;
(d) X4 is not R;
(e) X5 is not Q;
(f) X6 is not L;
(g) X8 is not V;
(h) XI0 is absent; or
(i) X9 and XI0 are absent.

In addition to the recited amino acids, X2, X3, X6 and X7 can be any aliphatic amino acid (whether naturally occurring or not), including but not limited to beta-alanine and 2-aminocyclohexane-1-carboxylic acid.

In various further embodiments, X4 is R; X5 is Q, and/or X8 is V. In various further embodiments, X3 is selected from the group consisting of V, L, I, A, G, Q, and N. In further embodiments, X6 is selected from the group consisting of C, A, G, L, V, I, M, Y, W, and F. In various further embodiments, X7 is selected from the group consisting of S, A, C, T, and G.

In some embodiments, at least one of Z1 and Z2 are a transduction domain.

The polypeptides of the present invention are useful, for example, as HSP27 kinase inhibitors, which can be used as therapeutic agents for a variety of disorders, as disclosed in more detail below.

The term "polypeptide" is used in its broadest sense to refer to a sequence of subunit amino acids, amino acid analogs, or peptidomimetics. The subunits are linked by peptide bonds, except where noted. The polypeptides described herein may be chemically synthesized or recombinantly expressed.

Preferably, the polypeptides of the present invention are chemically synthesized. Synthetic polypeptides, prepared using the well known techniques of solid phase, liquid phase, or peptide condensation techniques, or any combination thereof, can include natural and unnatural amino acids. Amino acids used for peptide synthesis may be standard Boc (N-α-amino protected N-α-t-butyloxycarbonyl) amino acid resin with the standard deprotecting, neutralization, coupling and wash protocols of the original solid phase procedure of Merrifield (1963, J. Am. Chem. Soc. 85:2149-2154), or the base-labile N-α-amino protected 9-fluorenylmethoxycarbonyl (Fmoc) amino acids first described by Carpino and Han (1972, J. Org. Chem. 37:3403-3409). Both Fmoc and Boc N-α-amino protected amino acids can be obtained from Sigma, Cambridge Research Biochemical, or other chemical companies familiar to those skilled in the art. In addition, the polypeptides can be synthesized with other N-α-protecting groups that are familiar to those skilled in this art.

Solid phase peptide synthesis may be accomplished by techniques familiar to those in the art and provided, for example, in Stewart and Young, 1984, Solid Phase Synthesis, Second Edition, Pierce Chemical Co., Rockford, Ill.; Fields and Noble, 1990, Int. J. Pept. Protein Res. 35:161-214, or using automated synthesizers. The polypeptides of the invention may comprise D-amino acids (which are resistant to L-amino acid-specific proteases in vivo), a combination of D- and L-amino acids, and various "designer" amino acids (e.g., β-methyl amino acids, C-α-methyl amino acids, and N-α-methyl amino acids, etc.) to convey special properties. Synthetic amino acids include ornithine for lysine, and norleucine for leucine or isoleucine.

In addition, the polypeptides can have peptidomimetic bonds, such as ester bonds, to prepare peptides with novel properties. For example, a peptide may be generated that incorporates a reduced peptide bond, i.e., $R_1$—$CH_2$—NH—$R_2$, where $R_1$ and $R_2$ are amino acid residues or sequences. A reduced peptide bond may be introduced as a dipeptide subunit. Such a polypeptide would be resistant to protease activity, and would possess an extended half-live in vivo.

In some embodiments, at least one of Z1 and Z2 is a transduction domain. As used herein, the term "transduction domain" means one or more amino acid sequence or any other molecule that can carry the active domain across cell membranes. These domains can be linked to other polypeptides to direct movement of the linked polypeptide across cell membranes. In some cases the transducing molecules do not need to be covalently linked to the active polypeptide. In one embodiment, the transduction domain is linked to the rest of the polypeptide via peptide bonding. (See, for example. Cell 55: 1179-1188, 1988; Cell 55:1189-1193, 1988; Proc Natl Acad Sci USA 91: 664-668, 1994; Science 285: 1569-1572, 1999; J Biol Chem 276: 3254-3261, 2001; and Cancer Res 61: 474-477, 2001). In a further embodiment, both Z1 and Z2 are transduction domains. In another embodiment, the transduction domain(s) is/are selected from the group consisting of $(R)_{4-9}$ (SEQ ID NO: 1); GRKKRRQRRRPPQ (SEQ ID NO: 2); RQRRKKRG (SEQ ID NO: 3); GRKKRRQR (SEQ ID NO: 4); AYARAAAR-QARA (SEQ ID NO: 5); DAATATRGRSAASRPTERPRA-PARSASRPRRRPVE (SEQ ID NO: 6); GWTLNSAGYLL-GLINLKALAALAKKIL (SEQ ID NO: 7); PLSSIFSRIGDP (SEQ ID NO: 8); AAVALLPAVLLALLAP (SEQ ID NO: 9); AAVLLPVLLAAP (SEQ ID NO: 10); VTVLALGALAGVGVG (SEQ ID NO: 11); GALFLGWL-GAAGSTMGAWSQP (SEQ ID NO: 12); GWTLNSAGYL-LGLINLKALAALAKKIL (SEQ ID NO: 13); KLALKLA-LKALKAALKLA (SEQ ID NO: 14); KETWWETWWTEWSQPKKKRKV (SEQ ID NO: 15); KAFAKLAARLYRKA (SEQ ID NO: 16); KAFAKLAAR-LYRAA (SEQ ID NO: 17); AAFAKLAARLYRKA (SEQ ID NO: 18); KAFAALAARLYRKA (SEQ ID NO: 19); KAF-AKLAARLYRKAGC (SEQ ID NO: 20); KAFAKLAAR-LYRAAGC (SEQ ID NO: 21); AAFAKLAARLYRKAGC (SEQ ID NO: 22); KAFAALAARLYRKAGC (SEQ ID NO: 23); KAFAKLAAQLYRKAGC (SEQ ID NO: 24), AGGGGYGRKKRRQRRR (SEQ ID NO: 25); YARAAAR-QARA (SEQ ID NO: 26); YGRKKRRQRRR (SEQ ID NO:

27); WLRRIKAWLRRIKA (SEQ ID NO: 28); WLR-RIKAWLRRIKAWLRRIKA (SEQ ID NO: 29); FAKLAARLYRKA (SEQ ID NO: 30); KAFAALAARLYRKA (SEQ ID NO: 31); KAFAKLAARLYRAA (SEQ ID NO: 32); KAFAKLAARLYRA (SEQ ID NO: 33); FAKLAARLYRAA (SEQ ID NO: 34); and FAKLAARLYRA (SEQ ID NO: 35).

Further exemplary polypeptides according to the invention include, but are not limited to any of those listed above, wherein one or both of Z1 and Z2 are selected from the group consisting of WLRRIKAWLRRIKA (SEQ ID NO: 28); WLRRIKA WLRRIKA WLRRIKA (SEQ ID NO: 29); YGRKKRRQRRR (SEQ ID NO: 27); YARAAARQARA (SEQ ID NO: 26); RQRRKKRG (SEQ ID NO: 3); GRKKRRQR (SEQ ID NO: 4); KAFAKLAARLYRKA (SEQ ID NO: 16); FAKLAARLYRKA (SEQ ID NO: 30); KAFAALAARLYRKA (SEQ ID NO: 31); KAFAKLAARLYRAA (SEQ ID NO: 32); KAFAKLAARLYRA (SEQ ID NO: 33); FAKLAARLYRAA (SEQ ID NO: 34); and FAKLAARLYRA (SEQ ID NO: 35).

In various further embodiments, exemplary polypeptides according to the invention include, but are not limited to those comprising or consisting of:

```
                                    (SEQ ID NO: 36)
YARAAARQARAKALARQLGVAA;

(SEQ ID NO: 37)
YGRKKRRQRRRKALARQLGVAA;

(SEQ ID NO: 38)
RQRRKKRGKALARQLGVAA;

(SEQ ID NO: 39)
GRKKRRQRKALARQLGVAA;

(SEQ ID NO: 40)
WLRRIKAWLRRIKAKALARQLGVAA;

(SEQ ID NO: 41)
WLRRIKAWLRRIKAWLRRIKAKALARQLGVAA;

(SEQ ID NO: 42)
YARAAARQARAKKKALARQLGVAA;

(SEQ ID NO: 43)
YGRKKRRQRRRKKKALARQLGVAA;

(SEQ ID NO: 44)
RQRRKKRGKKKALARQLGVAA;

(SEQ ID NO: 45)
GRKKRRQRKKKALARQLGVAA;

(SEQ ID NO: 46)
WLRRIKAWLRRIKAKKKALARQLGVAA;

(SEQ ID NO: 47)
WLRRIKAWLRRIKAWLRRIKAKKKALARQLGVAA;

(SEQ ID NO: 48)
KAFAKLAARLYRKALARQLGVAA;

(SEQ ID NO: 49)
FAKLAARLYRKALARQLGVAA;

(SEQ ID NO: 50)
KAFAKLAARLYRAALARQLGVAA;

(SEQ ID NO: 51)
KAFAKLAARLYRALARQLGVAA;

(SEQ ID NO: 52)
KAFAALAARLYRAALARQLGVAA;

(SEQ ID NO: 53)
FAKLAARLYRAALARQLGVAA;

(SEQ ID NO: 54)
WLRRIKAWLRRIKA-LNRQLGVAA;

(SEQ ID NO: 55)
YARAAARQARAKALNRQLGVA;

(SEQ ID NO: 56)
KAFAKLAARLYRKALNRQLAVAA;

(SEQ ID NO: 57)
FAKLAARLYRKALNRQLAVAA;

(SEQ ID NO: 58)
KAFAKLAARLYRKA-LNRQLGVAA;

(SEQ ID NO: 59)
FAKLAARLYRKA-LNRQLGVAA.
```

In another aspect, the present invention provides compositions, comprising one or more of the polypeptides disclosed herein, and a pharmaceutically acceptable carrier. Such pharmaceutical compositions are especially useful for carrying out the methods of the invention described below.

The term "active" refers to the ingredient, component or constituent of the compositions of the present invention responsible for the intended therapeutic effect.

A "pharmaceutical composition" is one that is employed to prevent, reduce in intensity, cure, or otherwise treat a target condition, syndrome, disorder or disease that has undergone federal regulatory review.

As used herein the term "pharmaceutically acceptable carrier" refers to any substantially non-toxic carrier conventionally useable for administration of pharmaceuticals in which the isolated polypeptide of the present invention will remain stable and bioavailable.

For administration, the polypeptides are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, dextran sulfate, glycosaminoglycan-containing gel or non-gel compositions or coatings, and/or polyvinyl alcohol, and tableted or encapsulated for conventional administration. Examples of glycosaminoglycans include but are limited to heparin, heparan sulfate, dermatan sulfate, chondroitin sulfate, hyaluronic acid, and keratan sulfate. Alternatively, the polypeptides of this invention may be dissolved in saline, water, polyethylene glycol, propylene glycol, carboxymethyl cellulose colloidal solutions, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art. The polypeptides may be linked to other compounds to promote an increased half-life in vivo, such as polyethylene glycol. Such linkage can be covalent or non-covalent as is understood by those of skill in the art.

The polypeptides may be made up in a solid form (including granules, powders or suppositories) or in a liquid form (e.g., solutions, suspensions, or emulsions). The polypeptides of the invention may be applied in a variety of solutions. Suitable solutions for use in accordance with the invention are sterile, dissolve sufficient amounts of the polypeptides, and are not harmful for the proposed application.

In another aspect, the present invention provides an isolated nucleic acid encoding a polypeptide of the present invention. Appropriate nucleic acids according to this aspect of the invention will be apparent to one of skill in the art based on the disclosure provided herein and the general level of skill in the art.

In another aspect, the present invention provides an expression vector comprising DNA control sequences operably linked to the isolated nucleic acids of the present invention, as disclosed above. "Control sequences" operably linked to the nucleic acids of the invention are nucleic acid sequences capable of effecting the expression of the nucleic acids of the invention. The control sequences need not be contiguous with the nucleic acids, so long as they function to direct the expression thereof. Thus, for example, intervening untranslated yet transcribed sequences can be present between a promoter sequence and the nucleic acid and the promoter sequence can still be considered "operably linked" to the coding sequence. Other such control sequences include, but are not limited to, polyadenylation signals, termination signals, and ribosome binding sites. Such expression vectors can be of any type known in the art, including but not limited to plasmid and viral-based expression vectors.

In a further aspect, the present invention provides genetically engineered host cells comprising the expression vectors of the invention. Such host cells can be prokaryotic cells or eukaryotic cells, and can be either transiently or stably transfected, or can be transduced with viral vectors.

In another aspect, the invention provides biomedical devices comprising one or more of the polypeptides of the present invention disposed on or in the biomedical device. As used herein, a "biomedical device" refers to a device to be implanted into a subject, for example, a human being, in order to bring about a desired result. Particularly preferred biomedical devices according to this aspect of the invention include, but are not limited to, stents (including but not limited to coronary stents), grafts (including but not limited to vascular grafts), shunts, stent grafts, fistulas, angioplasty devices, balloon catheters, venous catheters, implantable drug delivery devices, adhesion barriers (including but not limited to carboxymethylcellulose, hyaluronic acid, and PTFE sheets) to separate tissue, wound dressings such as films (e.g., polyurethane films), hydrocolloids (hydrophilic colloidal particles bound to polyurethane foam), hydrogels (cross-linked polymers containing about at least 60% water), other viscous liquids and hydrogel-like species (including but not limited to, those disclosed in US 20030190364), foams (hydrophilic or hydrophobic), calcium alginates (nonwoven composites of fibers from calcium alginate), cellophane, pluronics (ie: poly(ethylene glycol)-block-poly(propylene glycol), and biological polymers.

As used herein, the term "grafts" refers to both natural and prosthetic grafts and implants. In a preferred embodiment, the graft is a vascular graft.

As used herein, the term "stent" includes the stent itself, as well as any sleeve or other component that may be used to facilitate stent placement.

As used herein, "disposed on or in" means that the one or more polypeptides can be either directly or indirectly in contact with an outer surface, an inner surface, or embedded within the biomedical device. "Direct" contact refers to disposition of the polypeptides directly on or in the device, including but not limited to soaking a biomedical device in a solution containing the one or more polypeptides, spin coating or spraying a solution containing the one or more polypeptides onto the device, implanting any device that would deliver the polypeptide, and administering the polypeptide through a catheter directly on to the surface or into any organ.

"Indirect" contact means that the one or more polypeptides do not directly contact the biomedical device. For example, the one or more polypeptides may be disposed in a matrix, such as a gel matrix (such as a heparin coating) or a viscous fluid, which is disposed on the biomedical device. Such matrices can be prepared to, for example, modify the binding and release properties of the one or more polypeptides as required. In one non-limiting example, a heparin coating is disposed on the biomedical device (such as a poly(tetrafluoroethylene) (PTFE) vascular device or sheet) and the one or more polypeptides are disposed on or in a heparin coating; in this example, the one or more polypeptides can be delivered to a subject in need thereof in a controlled manner. In one non-limiting example, the release of the one or more polypeptides from interstitial surfaces of poly(tetrafluoroethylene) (PTFE) vascular devices or sheets can be controlled by first adsorbing or bonding heparin to the surface and/or interstices of the PTFE device followed by adsorption of polypeptide. Alternating layers of heparin and the polypeptide can also be used to increase the polypeptide dose and/or time of release. Under physiological conditions within the body, the kinetics of the association and dissociation of polypeptides disclosed herein to and from heparin will lead to a delayed release profile as compared to release of the polypeptide from a bare PTFE device. In addition, the release profile can be further altered through changes in local temperature, pH or ionic strength. Such controlled release is of great value for use in the various therapeutic treatments for which the biomedical devices can be used, as discussed below.

Heparin coatings on various medical devices are known in the art. Applications in humans include central venous catheters, coronary stents, ventricular assist devices, extracorporeal blood circuits, blood sampling devices, and vascular grafts. Such coatings can be in a gel or non-gel form. As used herein "heparin coating" includes heparin adsorbed to the surface, heparin bonded to the surface, and heparin imbedded in the PTFE polymer surface. An example of a method for bonding the heparin would be to use ammonia plasma to treat, for example, a PTFE surface and reacting the resultant amines with oxidized heparin. Layer-by-layer buildup of the heparin and one or more polypeptides could then be used to increase polypeptide on the surface and expand the delivery time. Gel forms of the heparin coating can include, but are not limited to, any hydrogel containing heparin either covalently or physically bound to the gel. The heparin coating is disposed on the biomedical device, which includes direct contact with an outer surface or an inner surface of the biomedical device, or embedded within the biomedical device. "Direct" contact refers to disposition directly on or in the device, including but not limited to soaking a biomedical device in a heparin coating solution (wherein the polypeptides may be added as part of the heparin coating solution, or may be subsequently disposed on or in the heparin coating after it is contacted with the device), spin coating or spraying a heparin coating solution onto the device (wherein the polypeptides may be added as part of the heparin coating solution, or may be subsequently disposed on or in the heparin coating after it is contacted with the device), and administering the heparin coating solution containing the polypeptides through a catheter directly on to the surface or into any organ. The physical characteristics and specific composition of the heparin layer can be any that provides the desired release profile of the one or more polypeptides. See, for example, Seal and Panitch, Biomacromolecules 2003(4):1572-1582 (2003); US20030190364, incorporated by reference herein in its entirety; and Carmeda BioActive Surface (CBAS™) the product of Carmeda AB in Stockholm, Sweden. "Indirect" contact means that the heparin coating is not directly in contact with the device such as, for example, when an intervening coating is placed between the device surface and the heparin coating. In one non-limiting example, the one or more polypeptides could be initially adsorbed (directly or indirectly), and then adsorbing a heparin coating; this can optionally be followed by subsequent polypeptide layers, heparin layers, or combinations thereof, as desired. As will be understood by those of skill in the art, any sulfated polysaccharide or negatively charged polymer can be used in like manner to heparin as described above, to provide desired release characteristics.

In a further aspect, the present invention provides methods for one or more of the following therapeutic uses: (a) reducing smooth muscle cell proliferation and/or migration; (b) promoting smooth muscle relaxation; (c) increasing the contractile rate in heart muscle; (d) increasing the rate of heart muscle relaxation; (e) promoting wound healing; (f) treating and/or reducing fibrotic disorders and/or keloids; (g) reducing scar formation; (h) disrupting focal adhesions; (i) regulating actin polymerization; and (j) treating or reducing incidence of one or more of intimal hyperplasia, stenosis, restenosis, atherosclerosis, smooth muscle cell tumors and metastasis, smooth muscle spasm, angina, Prinzmetal's angina, ischemia, stroke, bradycardia, hypertension, cardiac hypertrophy, renal failure, stroke, pulmonary hypertension, asthma, toxemia of pregnancy, pre-term labor, pre-eclampsia/eclampsia, Raynaud's disease or phenomenon, hemolytic-uremia, non-occlusive mesenteric ischemia, anal fissure, achalasia, impotence, migraine, ischemic muscle injury associated with smooth muscle spasm, vasculopathy, bradyarrythmia, bradycardia, congestive heart failure, stunned myocardium, pulmonary hypertension, diastolic dysfunction, gliosis (proliferation of astrocytes, and may include deposition of extracellular matrix, including but not limited to such proliferation and extracellular matrix ("ECM") deposition in damaged areas of the central nervous system); chronic obstructive pulmonary disease (i.e., respiratory tract diseases characterized by airflow obstruction or limitation; includes but is not limited to chronic bronchitis and emphysema), osteopenia, endothelial dysfunction, inflammation, rheumatoid arthritis, degenerative arthritis, ankylosing spondylitis, Sjogren's disease, Guilliame-Barre disease, infectious disease, sepsis, endotoxemic shock, psoriasis, radiation enteritis, scleroderma, cirrhosis, interstitial fibrosis, Crohn's disease, colitis, inflammatory bowel disease, appendicitis, gastritis, laryngitis, meningitis, pancreatitis, otitis, reperfusion injury, traumatic brain injury, spinal cord injury, peripheral neuropathy, multiple sclerosis, Lupus, allergy, cardiometabolic diseases, cardiovascular diseases, obesity, type II diabetes mellitus, type I diabetes mellitis, NASH/cirrhosis, and Alzheimer's disease; wherein the method comprises administering to a subject in need thereof an effective amount to carry out the one or more therapeutic uses of one or more polypeptides or compositions according to the present invention, or functional equivalents thereof.

Without being bound by theory, it is believed that the polypeptides of the present invention provide their therapeutic effect as a result of inhibiting HSP27 phosphorylation by HSP27 kinase (MAPKAP kinase 2), although alternative mechanisms, including but not limited to inhibition of HSP27 phosphorylation by MAPKAP kinase 3, and MAPKAP kinase 5 are also encompassed by the present invention.

Since MAPKAP2 is downstream of p38 MAP kinase, any therapeutic uses for which p38 MAPK inhibitors are useful are within the scope of the present invention as well.

As used herein, "treat" or "treating" means accomplishing one or more of the following: (a) reducing the severity of the disorder; (b) limiting development of symptoms characteristic of the disorder(s) being treated; (c) limiting worsening of symptoms characteristic of the disorder(s) being treated; (d) limiting recurrence of the disorder(s) in patients that have previously had the disorder(s); and (e) limiting recurrence of symptoms in patients that were previously symptomatic for the disorder(s).

As used herein, the term "reduce" or "reducing" means to limit occurrence of the disorder in individuals at risk of developing the disorder.

As used herein, "administering" includes in vivo administration, as well as administration directly to tissue ex vivo, such as vein grafts. The compositions of the present invention may be administered systemically either orally, buccally, parenterally, topically, by inhalation or insufflation (i.e., through the mouth or through the nose), or rectally in dosage unit formulations containing conventional nontoxic pharmaceutically acceptable carriers, adjuvants, and vehicles as desired.

For buccal administration, the compositions of the present invention may take the form of tablets or lozenges formulated in a conventional manner.

The term "parenteral" as used herein refers to introduction into the body by way of an injection (i.e., administration by injection), including, for example, subcutaneously (i.e., an injection beneath the skin), intramuscularly (i.e., an injection into a muscle); intravenously (i.e., an injection into a vein), intrathecally (i.e., an injection into the space around the spinal cord), intrasternal injection, or infusion techniques. A parenterally administered composition of the present invention is delivered using a needle, e.g., a surgical needle. The term "surgical needle" as used herein, refers to any needle adapted for delivery of fluid (i.e., capable of flow) compositions of the present invention into a selected anatomical structure. Injectable preparations, such as sterile injectable aqueous or oleaginous suspensions, may be formulated according to the known art using suitable dispersing or wetting agents and suspending agents.

The sterile injectable preparation also may be a sterile injectable solution or suspension in a nontoxic parenterally acceptable diluent or solvent, for example, as a solution in 1, 3-butanediol. A solution generally is considered as a homogeneous mixture of two or more substances; it is frequently, though not necessarily, a liquid. In a solution, the molecules of the solute (or dissolved substance) are uniformly distributed among those of the solvent. A suspension is a dispersion (mixture) in which a finely-divided species is combined with another species, with the former being so finely divided and mixed that it doesn't rapidly settle out. In everyday life, the most common suspensions are those of solids in liquid water. Among the acceptable vehicles and solvents that may be employed are water, Ringer's solution, and isotonic sodium chloride solution. In addition, sterile, fixed oils are conventionally employed as a solvent or suspending medium. For parenteral application, particularly suitable vehicles consist of solutions, preferably oily or aqueous solutions, as well as suspensions, emulsions, or implants. Aqueous suspensions may contain substances which increase the viscosity of the suspension and include, for example, sodium carboxymethyl cellulose, sorbitol and/or dextran. Optionally, the suspension may also contain stabilizers.

The term "topical" refers to administration of an inventive composition at, or immediately beneath, the point of application. The phrase "topically applying" describes application onto one or more surfaces(s) including epithelial surfaces. Although topical administration, in contrast to transdermal administration, generally provides a local rather than a systemic effect, as used herein, unless otherwise stated or implied, the terms topical administration and transdermal administration are used interchangeably.

Topical administration also may involve the use of transdermal administration such as transdermal patches or iontophoresis devices which are prepared according to techniques and procedures well known in the art. The terms "transdermal delivery system", transdermal patch" or "patch" refer to an adhesive system placed on the skin to deliver a time released dose of a drug(s) by passage from the dosage form through the skin to be available for distribution via the systemic circulation. Transdermal patches are a well-accepted technology used to deliver a wide variety of pharmaceuticals, including, but not limited to, scopolamine for motion sickness, nitroglycerin for treatment of angina pectoris, clonidine for hypertension, estradiol for postmenopausal indications, and nicotine for smoking cessation. Patches suitable for use in the present invention include, but are not limited to, (1) the matrix patch; (2) the reservoir patch; (3) the multi-laminate drug-in-adhesive patch; and (4) the monolithic drug-in-adhesive patch; TRANSDERMAL AND TOPICAL DRUG DELIVERY SYSTEMS, pp. 249-297 (Tapash K. Ghosh et al. eds., 1997), hereby incorporated herein by reference. These patches are well known in the art and generally available commercially.

The compositions of the present invention may be in the form of a dispersible dry powder for delivery by inhalation or insufflation (either through the mouth or through the nose). Dry powder compositions may be prepared by processes known in the art, such as lyophilization and jet milling, as disclosed in International Patent Publication No. WO 91/16038 and as disclosed in U.S. Pat. No. 6,921,527, the disclosures of which are incorporated by reference. The composition of the present invention is placed within a suitable dosage receptacle in an amount sufficient to provide a subject with a unit dosage treatment. The dosage receptacle is one that fits within a suitable inhalation device to allow for the aerosolization of the dry powder composition by dispersion into a gas stream to form an aerosol and then capturing the aerosol so produced in a chamber having a mouthpiece attached for subsequent inhalation by a subject in need of treatment. Such a dosage receptacle includes any container enclosing the composition known in the art such as gelatin or plastic capsules with a removable portion that allows a stream of gas (e.g., air) to be directed into the container to disperse the dry powder composition. Such containers are exemplified by those shown in U.S. Pat. No. 4,227,522; U.S. Pat. No. 4,192,309; and U.S. Pat. No. 4,105,027. Suitable containers also include those used in conjunction with Glaxo's Ventolin® Rotahaler brand powder inhaler or Fison's Spinhaler® brand powder inhaler. Another suitable unit-dose container which provides a superior moisture barrier is formed from an aluminum foil plastic laminate. The pharmaceutical-based powder is filled by weight or by volume into the depression in the formable foil and hermetically sealed with a covering foil-plastic laminate. Such a container for use with a powder inhalation device is described in U.S. Pat. No. 4,778,054 and is used with Glaxo's Diskhaler® (U.S. Pat. Nos. 4,627,432; 4,811,731; and 5,035,237). All of these references are incorporated herein by reference.

The compositions of the present invention may be in the form of suppositories for rectal administration of the composition. "Rectal" or "rectally" as used herein refers to introduction into the body through the rectum where absorption occurs through the walls of the rectum. These compositions can be prepared by mixing the drug with a suitable nonirritating excipient such as cocoa butter and polyethylene glycols which are solid at ordinary temperatures but liquid at the rectal temperature and will therefore melt in the rectum and release the drug. When formulated as a suppository the compositions of the invention may be formulated with traditional binders and carriers, such as triglycerides.

The following are nonlimiting examples of routes of delivery for various indications of the different embodiments of the methods of the invention: topical administration may be used for methods involving treatment or reducing the incidence of vein graft spasm, intimal hyperplasia, restenosis, prosthetic graft failure due to intimal hyperplasia, stent, stent graft failure due to intimal hyperplasia/constrictive remodeling, microvascular graft failure due to vasospasm, transplant vasculopathy, scarring, fibrosis, keloid formation, male and female sexual dysfunction, prevention of hydrocephalus caused by subarachnoid hemorrhage, and for promoting wound healing; intrathecal administration may be used for treating or reducing incidence of stroke and subarachnoid hemorrhage induced vasospasm; intraperitoneal administration may be used for treating or reducing incidence of non-occlusive mesenteric ischemia; oral administration may be used for treating or reducing incidence of achalasia; intravenous administration may be used for treating or reducing incidence of hypertension and bradycardia; rectal administration may be used for treating or reducing incidence of anal fissure; aerosol delivery may be used for treating or reducing incidence of asthma (ie: bronchospasm); and intrauterine administration may be used for treating or reducing incidence of pre-term labor and pre-eclampsia/eclampsia.

The term "disease" or "disorder", as used herein, refers to an impairment of health or a condition of abnormal functioning. The term "syndrome," as used herein, refers to a pattern of symptoms indicative of some disease or condition. The term "injury," as used herein, refers to damage or harm to a structure or function of the body caused by an outside agent or force, which may be physical or chemical. The term "condition", as used herein, refers to a variety of health states and is meant to include disorders or diseases caused by any underlying mechanism or disorder, injury, and the promotion of healthy tissues and organs.

The term "modulate" as used herein means to regulate, alter, adapt, or adjust to a certain measure or proportion.

The term "subject" or "individual" are used interchangeably to refer to a member of an animal species of mammalian origin, including humans.

Intimal hyperplasia is a complex process that leads to graft failure, and is the most common cause of failure of arterial bypass grafts. While incompletely understood, intimal hyperplasia is mediated by a sequence of events that include endothelial cell injury and subsequent vascular smooth muscle proliferation and migration from the media to the intima. This process is associated with a phenotypic modulation of the smooth muscle cells from a contractile to a synthetic phenotype. The "synthetic" smooth muscle cells secrete extracellular matrix proteins, which leads to pathologic narrowing of the vessel lumen leading to graft stenoses and ultimately graft failure. Such endothelial cell injury and subsequent smooth muscle cell proliferation and migration into the intima also characterize restenosis, most commonly after angioplasty to clear an obstructed blood vessel.

In some embodiments of the methods of the invention, such as those relating to reducing occurrence of smooth muscle cell proliferation and/or migration, or promoting smooth muscle relaxation, the administering may be direct, by contacting a blood vessel in a subject being treated with one or more polypeptides of the invention. For example, a liquid preparation of one or more polypeptides according to the invention can be forced through a porous catheter, or otherwise injected through a catheter to the injured site, or a gel or viscous liquid containing the one or more polypeptides according to the invention can be spread on the injured site. In these embodiments of direct delivery, one or more polypeptides according to the invention is delivered into smooth muscle cells at the site of injury or intervention. This can be accomplished, for example, by delivering the recombinant expression vectors (most preferably a viral vector, such as an adenoviral vector) of the invention to the site. Alternatively, delivery into smooth muscle cells is accomplished by using the one or more polypeptides according to the invention that include at least one transduction domain to facilitate entry into the smooth muscle cells.

In various other embodiments of the methods of the invention, particularly those that involve reducing occurrence of smooth muscle cell proliferation and/or migration, the method is performed on a subject who has undergone, is undergoing, or will undergo a procedure selected from the group consisting of angioplasty, vascular stent placement, endarterectomy, atherectomy, bypass surgery (such as coronary artery bypass surgery; peripheral vascular bypass surgeries), vascular grafting, organ transplant, prosthetic device implanting, microvascular reconstructions, plastic surgical flap construction, and catheter emplacement.

In another embodiment, the methods comprise treating or reducing occurrence of one or more disorders selected from the group consisting of intimal or neointimal hyperplasia, stenosis, restenosis, and atherosclerosis, comprising contacting a subject in need thereof with an amount effective to treat or reduce intimal or neointimal hyperplasia, stenosis, restenosis, and/or atherosclerosis of one or more polypeptides according to the invention.

In a further embodiment of this aspect of the invention, the method is used to treat tumors and/or metastasis, including but not limited to smooth muscle tumors. In one embodiment, the tumor is a leiomyosarcoma, which is defined as a malignant neoplasm that arises from muscle. Since leiomyosarcomas can arise from the walls of both small and large blood vessels, they can occur anywhere in the body, but peritoneal, uterine, and gastro-intestinal (particularly esophageal) leiomyosarcomas are more common. Alternatively, the smooth muscle tumor can be a leiomyoma, a non-malignant smooth muscle neoplasm. In a further embodiment, the method can be combined with other treatments for smooth muscle cell tumors and/or metastasis, such as chemotherapy, radiation therapy, and surgery to remove the tumor. Without being limited by theory, administration of the polypeptides of the invention can be used to treat tumors and/or metastasis by any or all of the following mechanisms: preventing drug resistance to anticancer drugs or promoting susceptibility to anti cancer drugs as a kinase inhibitor, promoting apoptosis of cancer cells, decreasing cell invasion through decreased matrix metalloproteinase expression and decreased migration of cancer cells, and through suppressing viral oncogenesis.

In a further embodiment, the methods of the invention are used for treating or reducing occurrence of smooth muscle spasm, comprising contacting a subject or graft in need thereof with an amount effective to reduce smooth muscle spasm of one or more polypeptides according to the invention.

Smooth muscles are found in the walls of blood vessels, airways, the gastrointestinal tract, and the genitourinary tract. Pathologic tonic contraction of smooth muscle constitutes spasm. Many pathological conditions are associated with spasm of vascular smooth muscle ("vasospasm"), the smooth muscle that lines blood vessels. This can cause symptoms such as angina and ischemia (if a heart artery is involved), or stroke as in the case of subarachnoid hemorrhage induced vasospasm if a brain vessel is involved. Hypertension (high blood pressure) is caused by excessive vasoconstriction, as well as thickening, of the vessel wall, particularly in the smaller vessels of the circulation.

Thus, in a further embodiment of the methods of the invention, the muscle cell spasm comprises a vasospasm, and the methods of the invention are used to treat or reduce occurrence of vasospasm. Embodiments of the method include, but are not limited to, methods to treat or inhibit angina, coronary vasospasm, Prinzmetal's angina (episodic focal spasm of an epicardial coronary artery), ischemia, stroke, bradycardia, and hypertension.

In another embodiment of the methods of the invention, occurrence of smooth muscle spasm is reduce by treatment of a graft, such as a vein or arterial graft, with the one or more polypeptides according to the invention. One of the ideal conduits for peripheral vascular and coronary reconstruction is the greater saphenous vein. However, the surgical manipulation during harvest of the conduit often leads to vasospasm. The exact etiology of vasospasm is complex and most likely multifactorial. Most investigations have suggested that vasospasm is either due to enhanced constriction or impaired relaxation of the vascular smooth muscle in the media of the vein. Numerous vasoconstricting agents such as endothelin-1 and thromboxane are increased during surgery and result in vascular smooth muscle contraction. Other vasoconstrictors such as norepinephrine, 5-hydroxytryptamine, acetylcholine, histamine, angiotensin II, and phenylephrine have been implicated in vein graft spasm. Papaverine is a smooth muscle vasodilator that has been used. In circumstances where spasm occurs even in the presence of papaverine, surgeons use intraluminal mechanical distension to break the spasm. This leads to injury to the vein graft wall and subsequent intimal hyperplasia. Intimal hyperplasia is the leading cause of graft failure.

Thus, in this embodiment, the graft can be contacted with the one or more polypeptides according to the invention, during harvest from the graft donor, subsequent to harvest (before implantation), and/or during implantation into the graft recipient (ie: ex vitro or in vivo). This can be accomplished, for example, by delivering the recombinant expression vectors (most preferably a viral vector, such as an adenoviral vector) of the invention to the site, and transfecting the smooth muscle cells. Alternatively, delivery into smooth muscle is accomplished by using the one or more polypeptides according to the invention that include at least one transduction domain to facilitate entry into the smooth muscle cells. In some embodiments, during graft implantation, the subject receiving the graft is treated systemically with heparin, as heparin has been shown to bind to protein transduction domains and prevent them from transducing into cells. This approach will lead to localized protein transduction of the graft alone, and not into peripheral tissues. The methods of this embodiment of the invention reduce occurrence of vein graft spasm during harvest and/or implantation of the graft, and thus improve both short and long term graft success.

In various other embodiments of the methods of the invention, the muscle cell spasm is associated with a disorder including, but not limited to pulmonary (lung) hypertension, asthma (bronchospasm), toxemia of pregnancy, pre-term labor, pre-eclampsia/eclampsia, Raynaud's disease or phenomenon, hemolytic-uremia, non-occlusive mesenteric ischemia (ischemia of the intestines that is caused by inadequate blood flow to the intestines), anal fissure (which is caused by persistent spasm of the internal anal sphincter), achalasia (which is caused by persistent spasm of the lower esophageal sphincter), impotence (which is caused by a lack of relaxation of the vessels in the penis, erection requires vasodilation of the corpra cavernosal (penile) blood vessels), migraine (which is caused by spasm of the intracranial blood vessels), ischemic muscle injury associated with smooth muscle spasm, and vasculopathy, such as transplant vasculopathy (a reaction in the transplanted vessels which is similar to atherosclerosis, it involves constrictive remodeling and ultimately obliteration of the transplanted blood vessels, this is the leading cause of heart transplant failure).

In other embodiments, the methods of the invention are used for one or more of promoting wound healing, reducing scar formation, treating and/or reducing fibrotic disorders and treating and/or reducing keloids. In these embodiments, an "individual in need thereof" is an individual that has suffered or will suffer (for example, via a surgical procedure) a wound that may result in scar formation, or has resulted in scar formation. As used herein, the term "wound" refers broadly to injuries to the skin and subcutaneous tissue. Such wounds include, but are not limited to lacerations; burns; punctures; pressure sores; bed sores; canker sores; trauma; bites; fistulas; ulcers; lesions caused by infections; periodontal wounds; endodontic wounds; burning mouth syndrome; laparotomy wounds; surgical wounds; incisional wounds; contractures after burns; tissue fibrosis, including but not limited to idiopathic pulmonary fibrosis, hepatic fibrosis, renal fibrosis, retroperitoneal fibrosis, and cystic fibrosis, but excluding blood vessel fibrosis or heart tissue fibrosis; and wounds resulting from cosmetic surgical procedures. In these embodiments, the one or more polypeptides or compositions are disposed on or in a wound dressing or other topical administration. Such wound dressings can be any used in the art, including but not limited to films (e.g., polyurethane films), hydrocolloids (hydrophilic colloidal particles bound to polyurethane foam), hydrogels (cross-linked polymers containing about at least 60% water), foams (hydrophilic or hydrophobic), calcium alginates (nonwoven composites of fibers from calcium alginate), cellophane, and biological polymers such as those described in US patent application publication number 20030190364, published Oct. 9, 2003, which is incorporated herein by reference.

As used herein, the phrase "reducing scar formation" means any decrease in scar formation that provides a therapeutic or cosmetic benefit to the patient. Such a therapeutic or cosmetic benefit can be achieved, for example, by decreasing the size and/or depth of a scar relative to scar formation in the absence of treatment with the methods of the invention, or by reducing the size of an existing scar. As used herein, such scars include scars of all types, including but not limited to keloids; hypertrophic scars; and adhesion formation between organ surfaces, including but not limited to those occurring as a result of surgery.

The methods of these embodiments are clinically useful for treating all types of wounds to reduce scar formation, both for reducing initial scar formation, and for therapeutic treatment of existing scars (i.e.: cutting out the scar after its formation, treating it with the compounds of the invention, and letting the scar heal more slowly). In some embodiments, individuals in need of treatment or limiting of scarring (such as keloids or hypertrophic scarring) are highly pigmented individuals, including but not limited to individuals of Asian or African descent, that are susceptible to keloids, and thus can benefit from the methods of the invention for prophylactic therapy to limit development of keloids, as well as for treating keloids. In various other embodiments, individuals in need of therapy for treating or limiting fibrotic disorders are those suffering from or at risk of one or more fibrotic disorders associated with TGFβ-induced CTGF expression, including but not limited to tissue fibrosis (including but not limited to idiopathic pulmonary fibrosis, hepatic fibrosis, renal fibrosis, retroperitoneal fibrosis, cystic fibrosis, blood vessel fibrosis, CNS fibrosis, and heart tissue fibrosis); diabetic nephropathy, glomerulosclerosis, and IgA nephropathy (causes of kidney failure and the need for dialysis and retransplant); diabetic retinopathy and macular degeneration (fibrotic diseases of the eye and leading causes of blindness); cirrhosis and biliary atresia (leading causes of liver fibrosis and failure); congestive heart failure; lung fibrosis; scleroderma; abdominal adhesions; and interstitial fibrosis.

In various other embodiments, individuals in need of therapy for treating and/or limiting fibrotic disorders and/or keloids are those with elevated levels of one or more of the following biomarkers:

TGFβ1 expression;
Collagen I;
CTGF expression; and
alpha smooth muscle actin.

Elevated levels of such biomarkers can be detected using standard techniques, including but not limited to immunological techniques (ELISA, immunocytochemistry, etc.) using commercially available antibodies against the one or more biomarkers As disclosed below, the polypeptides of the invention inhibit TGFβ1-induced CTGF and collagen expression in human keloid fibroblasts, which are elevated in fibrotic conditions, indicating that individuals with elevated levels of one or more of these biomarkers can especially benefit from the methods of the present invention. As used herein, an "elevated" level of the one or more biomarkers means any increase above normal for that individual or similarly situated individuals in a relevant target tissue. Such target tissues are those affected by fibrotic conditions, including but not limited to blood, wound exudate, and biopsies taken from tissues affected by fibrosis including but not limited to those disclosed above (skin, kidney, lung, liver, peritoneum, blood vessel, heart, retina, etc.) In various further embodiments, an individual in need thereof is one that has a level of one or more of the recited biomarkers 5%, 10%, 15%, 20%, 25%, 50%, 75%, 100%, or more above normal levels. Determining the level of the one or more biomarkers can be done using standard techniques in the art for measuring protein and/or gene expression, including but not limited to those disclosed below.

A "normal" level of these one or more biomarkers may be established by any suitable means, including but not limited to determining a normal level in that individual or similarly situated individuals in the absence of fibrotic conditions and/or keloids, or any other suitable means to establish a standard for reference. A method to treat a disease, disorder or condition according to the present invention comprises the steps of (1) administering to a subject in need thereof a therapeutically effective amount of a composition according to the present invention; (2) monitoring a level of at least one biomarker in a target tissue, wherein the at least one biomarker is selected from the group consisting of:

TGFβ1 expression;
collagen I expression;
CTGF expression; and
α-smooth muscle actin expression;

and (3) maintaining the level of the biomarker in the target tissue substantially at normal levels during treatment.

In another embodiment of the methods of the invention, the methods are used to increase the contractile rate in heart muscle. Individuals that can benefit from such treatment include those who exhibit a reduced heart rate relative to either a normal heart rate for the individual, or relative to a "normal" heart rate for a similarly situated individual. As used herein, the phrase "increasing the contractile rate in heart muscle" means any increase in contractile rate that provides a therapeutic benefit to the patient. Such a therapeutic benefit can be achieved, for example, by increasing the contractile rate to make it closer to a normal contractile rate for the individual, a normal contractile rate for a similarly situated individual, or some other desired target contractile rate. In a one embodiment, the methods result in an increase of at least 5% in the contractile rate of the patient in need of such treatment. In further embodiments, the methods of the invention result in an increase of at least 10%, 15%, 20%, 25%, 30%, 35%, 40%, 45%, and/or 50% in the contractile rate of the patient in need of such treatment. In some embodiments, increasing the contractile rate in heart muscle is accomplished by increasing the heart muscle relaxation rate (i.e., if the muscles relax faster, they beat faster). In other embodiments, the methods of the invention result in an increase of at least 5% in the heart muscle relaxation rate of the patient in need of such treatment. In further embodiments, the methods of the invention result in an increase of at least 10%, 15%, 20%, 25%, 30%, 35%, 40%, 45%, and/or 50% in the heart muscle relaxation rate of the patient in need of such treatment.

In a further embodiment of the methods of the invention, the methods are performed to treat one or more cardiac disorders that can benefit from increasing the contractile rate in heart muscle. Such cardiac disorders include bradyarrythmias, bradycardias congestive heart failure, pulmonary hypertension, stunned myocardium, and diastolic dysfunction. As used herein, "bradyarrythmia" means an abnormal decrease of the rate of the heartbeat to less than 60 beats per minute, generally cased by a disturbance in the electrical impulses to the heart. A common cause of bradyarrythmias is coronary heart disease, which leads to the formation of atheromas that limit the flow of blood to the cardiac tissue, and thus the cardiac tissue becomes damaged. Bradyarrythmias due to coronary artery disease occur more frequently after myocardial infarction. Symptoms include, but are not limited to, loss of energy, weakness, syncope, and hypotension.

As used herein, "Congestive heart failure" means an inability of the heart to pump adequate supplies of blood throughout the body. Such heart failure can be due to a variety of conditions or disorders, including but not limited to hypertension, anemia, hyperthyroidism, heart valve defects including but not limited to aortic stenosis, aortic insufficiency, and tricuspid insufficiency; congenital heart defects including but not limited to coarctation of the aorta, septal defects, pulmonary stenosis, and tetralogy of Fallot; arrythmias, myocardial infarction, cardiomyopathy, pulmonary hypertension, and lung disease including but not limited to chronic bronchitis and emphysema. Symptoms of congestive heart failure include, but are not limited to, fatigue, breathing difficulty, pulmonary edema, and swelling of the ankles and legs.

As used herein, "Stunned myocardium" means heart muscle that is not functioning (pumping/beating) due to cardiac ischemia (lack of blood flow/oxygen to the vessels supplying the heat muscle).

As used herein, "Diastolic dysfunction" means an inability of the heart to fill with blood during diastole (the resting phase of heart contraction). This condition usually occurs in the setting of left ventricular hypertrophy. The heart muscle becomes enlarged and stiff such that it cannot fill adequately. Diastolic dysfunction can result in heart failure and inadequate heart function.

As used herein, "Pulmonary hypertension" means a disorder in which the blood pressure in the arteries supplying the lungs is abnormally high. Causes include, but are not limited to, inadequate supply of oxygen to the lungs, such as in chronic bronchitis and emphysema; pulmonary embolism, and intestinal pulmonary fibrosis. Symptoms and signs of pulmonary hypertension are often subtle and nonspecific. In the later stages, pulmonary hypertension leads to right heart failure that is associated with liver enlargement, enlargement of veins in the neck and generalized edema.

In a further embodiment of the methods of the invention, the methods are used for treating a heart muscle disorder comprising administering to an individual suffering from one or more of bradyarrythmia, bradycardia, congestive heart failure, stunned myocardium, pulmonary hypertension, and diastolic dysfunction, an amount effective to increase heart muscle contractile rate of one or more polypeptides according to the present invention.

Treating bradyarrythmia includes one or more of the following (a) improving the rate of the heartbeat to closer to normal levels for the individual, closer to a desired rate, or increasing to at least above 60 beats per minute; (b) reducing the occurrence of one or more of loss of energy, weakness, syncope, and hypotension in patients suffering from bradyarrythmia; (c) reducing worsening of one or more of loss of energy, weakness, syncope, and hypotension in patients suffering from bradyarrythmia and its symptoms; (d) reducing recurrence of bradyarrythmia in patients that previously suffered from bradyarrythmia; and (e) reducing recurrence of one or more of loss of energy, weakness, syncope, and hypotension in patients that previously suffered from bradyarrythmia.

Similarly, treating congestive heart failure includes one or more of the following (a) improving the heart's ability to pump adequate supplies of blood throughout the body to closer to normal levels for the individual, or closer to a desired pumping capacity; (b) reducing development of one or more of fatigue, breathing difficulty, pulmonary edema, and swelling of the ankles and legs in patients suffering from congestive heart failure; (c) reducing worsening of one or more of fatigue, breathing difficulty, pulmonary edema, and swelling of the ankles and legs in patients suffering from congestive heart failure and its symptoms; (d) reducing recurrence of congestive heart failure in patients that previously suffered from congestive heart failure; and (e) reducing recurrence of one or more of fatigue, breathing difficulty, pulmonary edema, and swelling of the ankles and legs in patients that previously suffered from congestive heart failure.

Treating stunned myocardium means one or more of (a) improving the ability of the heart muscle to pump by improving the oxygenation of the ischemic muscle, or by decreasing the need of the myocardial cells for oxygen and (b) reducing recurrence of stunned myocardium in patients that previously suffered from stunned myocardium.

Similarly, treating diastolic dysfunction includes one or more of (a) reducing occurrence of heart failure and/or inadequate heart function by allowing the heart to relax and fill more completely; (b) reducing recurrence of diastolic dysfunction in patients that previously suffered from diastolic dysfunction; and (c) reducing recurrence of heart failure and/or inadequate heart function in patients that previously suffered from diastolic dysfunction.

Treating pulmonary hypertension includes one or more of the following (a) decreasing blood pressure in the arteries supplying the lungs to closer to normal levels for the individual, or closer to a desired pressure; (b) reducing the occurrence of one or more of enlargement of veins in the neck, enlargement of the liver, and generalized edema in patients suffering from pulmonary hypertension; (c) reducing worsening of one or more of enlargement of veins in the neck, enlargement of the liver, and generalized edema in patients suffering from pulmonary hypertension and its symptoms; (d) reducing recurrence of pulmonary hypertension in patients that previously suffered from pulmonary hypertension; and (e) reducing recurrence of one or more of enlargement of veins in the neck, enlargement of the liver, and generalized edema in patients that previously suffered from pulmonary hypertension.

In a further aspect, the present invention provides methods for reducing occurrence of a heart muscle disorder comprising administering to an individual at risk of developing bradyarrythmia, bradycardia, congestive heart failure, stunned myocardium, pulmonary hypertension, and diastolic dysfunction an amount effective to increase heart muscle contractile rate of one or more polypeptides or compositions according to the present invention.

For example, methods to reduce occurrence of congestive heart failure involve administration of one or more polypeptides or compositions according to the present invention to a subject that suffers from one or more of hypertension, anemia, hyperthyroidism, heart valve defects including but not limited to aortic stenosis, aortic insufficiency, and tricuspid insufficiency; congenital heart defects including but not limited to coarctation of the aorta, septal defects, pulmonary stenosis, and tetralogy of Fallot; arrythmias, myocardial infarction, cardiomyopathy, pulmonary hypertension, and lung disease including but not limited to chronic bronchitis and emphysema.

Similarly, methods to reduce occurrence of bradyarrythmia involve administration of the one or more polypeptides or compositions according to the present invention to a subject that suffer from one or more of coronary heart disease and atheroma formation, or that previously had a myocardial infarction or conduction disorder.

Similarly, methods to reduce occurrence of pulmonary hypertension involve administration of the one or more polypeptides or compositions according to the present invention to a subject that suffers from one or more of chronic bronchitis, emphysema, pulmonary embolism, and intestinal pulmonary fibrosis.

Reducing occurrence of stunned myocardium involves administration of the one or more polypeptides or compositions according to the present invention to a subject that suffers from cardiac ischemia.

Reducing occurrence of or treating diastolic dysfunction involves administration of the one or more polypeptides or compositions according to the present invention to a subject that suffers from left ventricular hypertrophy In other embodiments, the methods of the invention are used to treat or limit the incidence of inducing neural regeneration for central nervous system injuries. As used herein, the term "central nervous system" (CNS) refers to the brain and spinal cord. As used herein, the term "neural regeneration" includes both regenerating a damaged neural connection, as well as promoting an increase in neural function (including but not limited to treatment of Alzheimer's and peripheral neuropathy); such neural regeneration can be in peripheral nervous system or the central nervous system. Without being limited by theory, it is believed that administration of the peptides to a patient in need thereof prevents or limits activity of the protein rho, which is known to cause growth cone collapse; thus, minimizing rho activity enhances neurite outgrowth.

In other embodiments, the methods of the invention are used to treat or limit the incidence of gliosis (proliferation of astrocytes in damaged areas of the central nervous system). Astrocytes are the connective tissue cells of the CNS, and have functions including accumulating in areas with damaged neurons. Gliosis occurs during any traumatic brain injury, insertion of neural electrodes and during spinal cord injury, as well as in various neurodegenerative disorders including but not limited to Korsakoff's syndrome and AIDS dementia complex. Without being limited by theory, it is believed that administration of the peptides to a patient in need thereof prevents or limits the fibrotic response of astrocytes and possibly microglia to inhibit fibrosis.

In other embodiments, the methods of the invention are used to treat or limit the incidence of chronic obstructive pulmonary disease (COPD), which is a group of respiratory tract diseases characterized by airflow obstruction or limitation. COPD can be caused by a variety of factors, including but not limited to tobacco smoking (chronic smokers at risk), exposure to coal dust (coal mining industry workers particularly at risk), congenital defects (including but not limited to alpha 1-antitrypsin deficiency), or it may be idiopathic (no known cause). COPD includes, but is not limited to chronic bronchitis and emphysema. Symptoms characteristic of COPD (for which the methods of the invention can be used to treat or reduce incidence of) include, but are not limited to recurrent respiratory infections, severe cough, constant wheezing, shortness of breath with minimal exertion or rest, hypoxia, and excessive sputum production.

The polypeptides of the invention can be used alone or together with other treatments for COPD, including, bronchodilators, antibiotics, and oral or intravenous steroids.

In other embodiments, the methods of the invention are used to treat or limit the incidence of inflammation. As used herein, "inflammation" means the response by the immune system to infection, irritation, or associated with foreign bodies (introduction of biomaterials) in the body.

In various other embodiments, individuals in need of therapy for treating and/or limiting inflammatory disorders and/or autoimmune diseases oftentimes are those with elevated levels of one or more of the following biomarkers:

TGFβ1 expression;
TNF-α;
IL-1;
IL-6;

IL-8;
COX-2;
MIP-1α; and
MIP-2.

Elevated levels of such biomarkers can be detected using standard techniques, including but not limited to immunological techniques (ELISA, immunocytochemistry, etc.) using commercially available antibodies against the one or more biomarkers.

Symptoms characteristic of inflammation (for which the methods of the invention can be used to treat or reduce incidence of) include, but are not limited to redness, heat, swelling, pain, and dysfunction of the organs involved. Specific inflammatory disorders that can be treated, or whose incidence can be reduced, by the methods of the invention include, but are not limited to, asthma, arthritis (rheumatoid or degenerative), sepsis, endotoxemic shock, psoriasis, radiation enteritis, scleroderma, cirrhosis, interstitial fibrosis, Crohn's disease, inflammatory bowel disease, appendicitis, gastritis, laryngitis, meningitis, pancreatitis, and otitsis.

Without being limited by theory, it is believed that administration of the polypeptides of the invention to a patient in need of anti-inflammatory treatment suppresses the response to and/or expression of inflammatory cytokines including but not limited to TGF β1, tumor necrosis factor α (TNF-α), interleukin 1 (IL-1), IL-6, IL-8, COX-2, and macrophage inflammatory protein (e.g., MIP-1α and MIP-2).

In all of the above embodiments of the therapeutic methods of the invention, the polypeptides of the invention can be used as the sole active agent, or can be combined with one or more other treatments for the indication, as determined by an attending physician.

As used herein for all of the methods of the invention, a "therapeutically effective amount" or an "amount effective" of the one or more polypeptides is an amount that is sufficient to provide the intended benefit of treatment. An effective amount of the polypeptides that can be employed ranges generally between about 0.01 µg/kg body weight and about 10 mg/kg body weight, preferably ranging between about 0.05 µg/kg and about 5 mg/kg body weight. However dosage levels are based on a variety of factors, including the type of injury, the age, weight, sex, medical condition of the individual, the severity of the condition, the route of administration, and the particular compound employed. Thus, the dosage regimen may vary widely, but can be determined routinely by a physician using standard methods.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and described the methods and/or materials in connection with which the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Experiments with Polypeptide WLRRIKAWLRRIKA-LNRQLGVAA (SEQ ID NO: 54, "BIP") in an In Vitro Model of Keloid Formation and Hyperplastic Scarring:

Keloid fibroblasts are an appropriate model of keloid formation and hyperplastic scarring. First, no reliable animal models of hyperplastic scarring exist. To our knowledge, no animal species provides a natural non-cancer related model of hyperplastic scarring. Furthermore, animal models of scarring that do exist use extreme methods to induce consistent scarring such as full thickness burning of skin and allografting. [[D. Y. Yang, S. R. Li, G. Li, J. Y. Liu, Z. X. Wang, J. L. Wu, and Y. Q. Chen, "[Establishment of an animal model of human hyperplastic scar in nude mice]," *Zhonghua Shao Shang Za Zhi*, vol. 20, pp. 82-4, April 2004.] These aggressive methods are much more extreme than the simple surgical cuts than often induce keloid formation or hyperplastic scarring in humans. Another investigator has used tissue engineered scaffolds to implant human keloid fibroblast in athymic mice. [H. B. Wang and S. K. Luo, "[Construction of animal models of keloid by tissue engineering]," *Di Yi Jun Yi Da Xue Xue Bao*, vol. 25, pp. 815-9, 832, July 2005.] Athymic, asplenic mice have also been used to implant human keloid tissue into animals. [M. Polo, P. D. Smith, Y. J. Kim, X. Wang, F. Ko, and M. C. Robson, "Effect of TGF-beta2 on proliferative scar fibroblast cell kinetics," *Ann Plast Surg*, vol. 43, pp. 185-90, August 1999.] However, in both of these cases, the investigators rely on human keloid fibroblasts as the primary cells in their tissue implantations.

Second, in vitro keloid fibroblasts are widely used as models of hyperplastic scarring by a myriad of other investigators interested in studying the biochemical basis of scarring and therapies to hyperplastic scarring. [R. J. Koch, R. L. Goode, and G. T. Simpson, "Serum-free keloid fibroblast cell culture: an in vitro model for the study of aberrant wound healing," in *Plast Reconstr Surg*. vol. 99, 1997, pp. 1094-8. W. Xia, M. T. Longaker, and G. P. Yang, "P38 MAP kinase mediates transforming growth factor-beta2 transcription in human keloid fibroblasts," *Am J Physiol Regul Integr Comp Physiol*, vol. 290, pp. R501-8, March 2006. W. Xia, W. Kong, Z. Wang, T. T. Phan, I. J. Lim, M. T. Longaker, and G. P. Yang, "Increased CCN2 transcription in keloid fibroblasts requires cooperativity between AP-1 and SMAD binding sites," *Ann Surg*, vol. 246, pp. 886-95, November 2007. A. S. Vincent, T. T. Phan, A. Mukhopadhyay, H. Y. Lim, B. Halliwell, and K. P. Wong, "Human Skin Keloid Fibroblasts Display Bioenergetics of Cancer Cells," *J Invest Dermatol*, Oct. 18, 2007. R. P. Abergel, D. Pizzurro, C. A. Meeker, G. Lask, L. Y. Matsuoka, R. R. Minor, M. L. Chu, and J. Uitto, "Biochemical composition of the connective tissue in keloids and analysis of collagen metabolism in keloid fibroblast cultures," *J Invest Dermatol*, vol. 84, pp. 384-90, May 1985. K. Sahara, A. Kucukcelebi, F. Ko, L. Phillips, and M. Robson, "Suppression of in vitro proliferative scar fibroblast contraction by interferon alfa-2b," *Wound Repair Regen*, vol. 1, pp. 22-7, January 1993. J. D. Russel, S. B. Russell, and K. M. Trupin, "The effect of histamine on the growth of cultured fibroblasts isolated from normal and keloid tissue," *J Cell Physiol*, vol. 93, pp. 389-93, December 1977. G. Pinol, F. Rueda, F. Marti, L. Puig, and J. M. De Moragas, "[Effect of minoxidil on DNA synthesis in cultured fibroblasts from healthy skin or keloids]," *Med Cutan Ibero Lat Am*, vol. 18, pp. 13-7, 1990. M. C. McCormack, K. C. Nowak, and R. J. Koch, "The effect of copper tripeptide and tretinoin on growth factor production in a serum-free fibroblast model," *Arch Facial Plast Surg*, vol. 3, pp. 28-32, January-March 2001. L. Y. Matsuoka, J. Uitto, J. Wortsman, R. P. Abergel, and J. Dietrich, "Ultrastructural characteristics of keloid fibroblasts," *Am J Dermatopathol*, vol. 10, pp. 505-8, December 1988. J. Kossi and M. Laato, "Different metabolism of hexose sugars and sucrose in wound fluid and in fibroblast cultures derived from granulation tissue, hypertrophic scar and keloid," *Pathobiology*, vol. 68, pp. 29-35, January-February 2000. R. H. Hong, J. Lum, and R. Koch, "Growth of keloid-producing fibroblasts in commercially available serum-free media," *Otolaryngol Head Neck Surg*, vol. 121, pp. 469-73, October 1999. M. M. Hanasono, M. Kita, A. A. Mikulec, D. Lonergan, and R. J. Koch, "Autocrine growth factor production by fetal, keloid, and normal dermal fibroblasts," *Arch Facial Plast Surg*, vol. 5, pp. 26-30, January-February 2003. A. Dalkowski, S. Fimmel, C. Beutler, and C. Zouboulis Ch, "Cryotherapy modifies synthetic activity and differentiation of keloidal fibroblasts in vitro," *Exp Dermatol*, vol. 12, pp. 673-81, October 2003. L. L. Chiu, C. H. Sun, A. T. Yeh, B. Torkian, A. Karamzadeh, B. Tromberg, and B. J. Wong, "Photodynamic therapy on keloid fibroblasts in tissue-engineered keratinocyte-fibroblast co-culture," *Lasers Surg Med*, vol. 37, pp. 231-44, September 2005. L. A. Carroll and R. J. Koch, "Heparin stimulates production of bFGF and TGF-beta 1 by human normal, keloid, and fetal dermal fibroblasts," *Med Sci Monit*, vol. 9, pp. BR97-108, March 2003. L. A. Carroll, M. M. Hanasono, A. A. Mikulec, M. Kita, and R. J. Koch, "Triamcinolone stimulates bFGF production and inhibits TGF-beta 1 production by human dermal fibroblasts," *Dermatol Surg*, vol. 28, pp. 704-9, August 2002. M. Calderon, W. T. Lawrence, and A. J. Banes, "Increased proliferation in keloid fibroblasts wounded in vitro," *J Surg Res*, vol. 61, pp. 343-7, March 1996. P. D. Butler, D. P. Ly, M. T. Longaker, and G. P. Yang, "Use of organotypic coculture to study keloid biology," *Am J Surg*, Dec. 5, 2007.] Keloid fibroblasts are linked to increased extracellular matrix production. [R. P. Abergel, D. Pizzurro, C. A. Meeker, G. Lask, L. Y. Matsuoka, R. R. Minor, M. L. Chu, and J. Uitto, "Biochemical composition of the connective tissue in keloids and analysis of collagen metabolism in keloid fibroblast cultures," *J Invest Dermatol*, vol. 84, pp. 384-90, May 1985.] In particular, keloid cells are associated with increased type I collagen production, and type I collagen is the primary extracellular matrix molecule found in hyperplastic scars and keloids. [R. P. Abergel, D. Pizzurro, C. A. Meeker, G. Lask, L. Y. Matsuoka, R. R. Minor, M. L. Chu, and J. Uitto, "Biochemical composition of the connective tissue in keloids and analysis of collagen metabolism in keloid fibroblast cultures," *J Invest Dermatol*, vol. 84, pp. 384-90, May 1985.] Clearly, keloid fibroblasts are an appropriate model for the study of hyperplastic scarring and keloid formation.

Figure 1B:
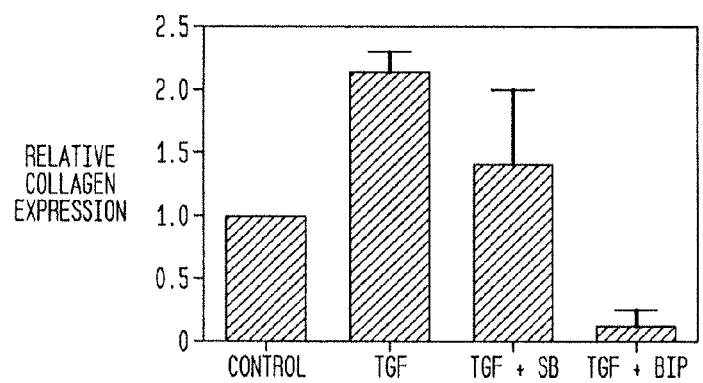

Example 1 HSP27 Kinase Inhibitor Peptide (BIP) Inhibits TGF-β1 Induced Expression of CTGF and Collagen in Human Keloid Fibroblasts Human keloid fibroblasts were maintained in Dulbecco's modified Eagle's medium (DMEM) supplemented with fetal calf serum (10%) and streptomycin/penicillin (1%). They were grown to 80% confluence, and then serum starved for 48 hours. The cells were subsequently stimulated with nothing (control), with 1.25 ng/ml of transforming growth factor beta 1 (TGF) for 24 hours, with 25 µM of a p38 MAP kinase inhibitor, SB 203580, for 2 h followed by TGF-β1 (TGF+SB) or with 60 µM of test polypeptide WLR-RIKAWLRRIKA-LNRQLGVAA (BIP) (SEQ ID NO: 56) for 2 hours followed by TGF-β1 for 24 hours (TGF+BIP). The expression of connective tissue growth factor (CTGF) and collagen was assessed by immunoblot and normalized to GAPDH (loading control) expression. Results in the graphs (FIG. 1) represent average±standard deviation from three independent experiments. These results demonstrate that BIP inhibits TGF-β1 induced expression of CTGF and collagen in human keloid fibroblasts.

Figure 2:
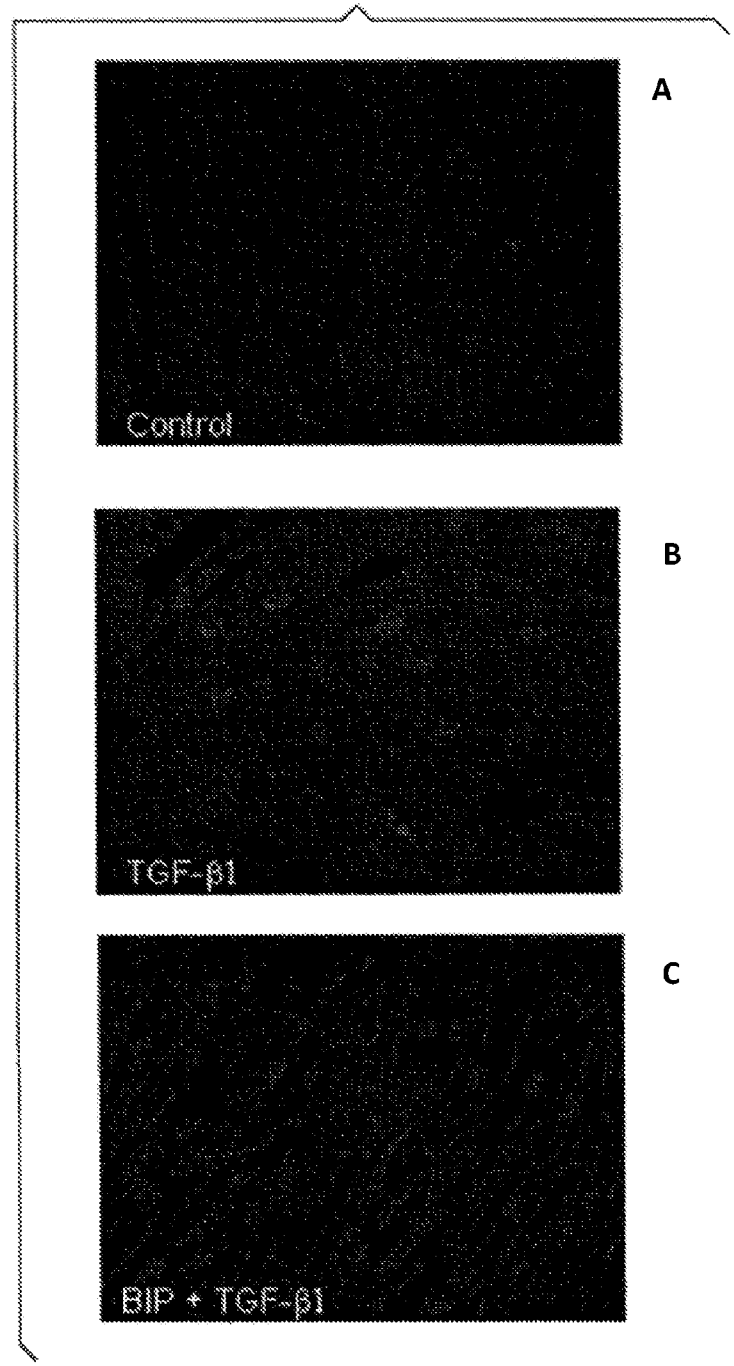
FIG. 2: Data graph showing that HSP27 kinase inhibitor peptide (BIP) (SEQ ID NO: 54) inhibits TGF-β1 induced stress fiber formation in human keloid fibroblasts. Panel A: control; Panel B: human keloid fibroblasts treated with TGF-β1; and Panel C: human keloid fibroblasts treated with BIP and TGF-β1.

Example 2 HSP27 Kinase Inhibitor Peptide (BIP) Inhibits TGF-β1 Induced Stress Fiber Formation in Human Keloid Fibroblasts Human keloid fibroblasts were maintained in Dulbecco's modified Eagle's medium (DMEM) supplemented with fetal calf serum (10%) and streptomycin/penicillin (1%). They were grown on cover slips and then serum starved for 48 hours. The cells were subsequently stimulated with nothing (control), with 1.25 ng/ml of transforming growth factor beta 1 (TGF-β1) for 24 hours, or with 60 µM test polypeptide WLRRIKAWLRRIKALNRQLGVAA (BIP) (SEQ ID NO: 54) for 2 hours followed by TGF-β1 for 24 h (TGF-β1+BIP). Cells were washed, processed for microscopy and labeled with Alexa 586-conjugated phalloidin to reveal the actin cytoskeleton and DAPI to reveal the nucleus. FIG. 2, at a magnification of 40×, demonstrates that pre-treatment of cells with BIP followed by TGF-β1 led to loss of central actin and reduced stress fiber formation in keloid fibroblasts.

Example 3 HSP27 Kinase Inhibitor Peptide (BIP) Inhibits TGF-β1 Induced Phosphorylation of HSP27 in Human Keloid Fibroblasts (Fluorescence Microscopy)

Figure 3:
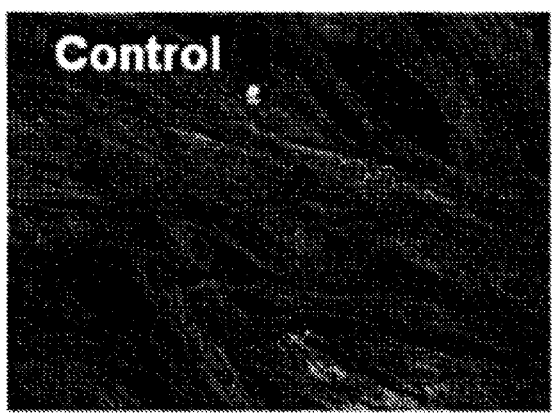
FIG. 3: Data graph showing that HSP27 kinase inhibitor peptide (BIP) inhibits TGF-β1 induced phosphorylation of HSP27 in human keloid fibroblasts. Panel A: control; Panel B: human keloid fibroblasts treated with TGF-β1; and Panel C: human keloid fibroblasts treated with BIP and TGF-β1.
Figure 3:
Figure 3:
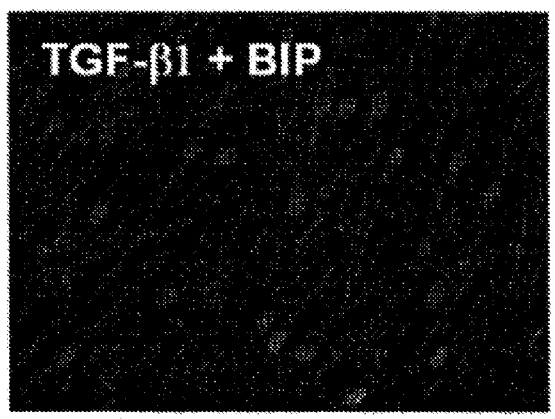

Human keloid fibroblasts were maintained in Dulbecco's modified Eagle's medium (DMEM) supplemented with fetal calf serum (10%) and streptomycin/penicillin (1%). They were grown on cover slips and then serum starved for 48 hours. The cells were subsequently stimulated with nothing (control), with 1.25 ng/ml of transforming growth factor beta 1 (TGF-β1) for 24 hours or with 60 µM test polypeptide WLRRIKAWLRRIKALNRQLGVAA (BIP) (SEQ ID NO:

54) for 2 hours followed by TGF-β1 for 24 hours (TGF-β1+BIP). Cells were washed, processed for microscopy and labeled with Cy2 for phospho-HSP27 (ser 78/82, green fluorescence), Alexa 586-conjugated phalloidin (red) to reveal the actin cytoskeleton and DAPI (blue) to reveal nucleus. FIG. 3, each panel shown at a magnification of 40×, shows that pre-treatment of cells with BIP followed by TGF-β1 reduced phosphorylation of HSP27 in keloid fibroblasts. These data demonstrated that BIP inhibits TGF-β1 induced phosphorylation of HSP27 in human keloid fibroblasts.

Example 4 HSP27 Kinase Inhibitor Peptide (BIP) Inhibits TGF-β1 Induced Phosphorylation of HSP27 in Human Keloid Fibroblasts (Immunoblot)

Figure 4A:
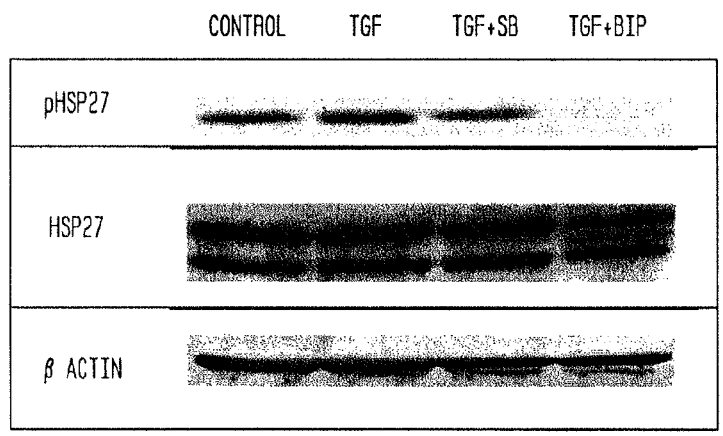
(FIG. 4A) Immunoblot, and (FIG. 4B) Data graph showing that HSP27 kinase inhibitor peptide (BIP) inhibits TGF-β1 induced phosphorylation of HSP27 in human keloid fibroblasts.
Figure 4B:
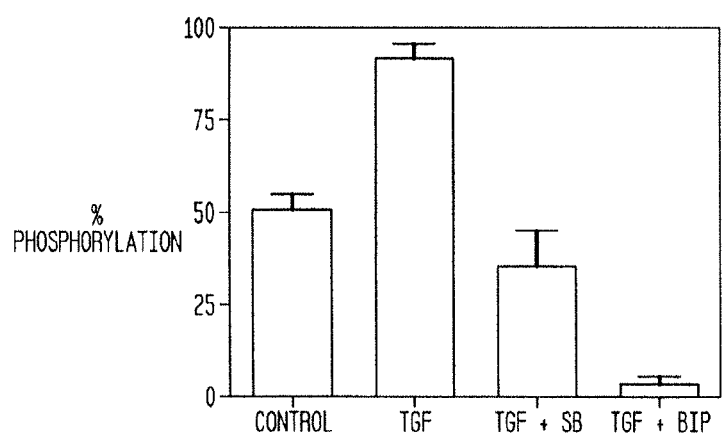
FIG. 4.

Human keloid fibroblasts were maintained in Dulbecco's modified Eagle's medium (DMEM) supplemented with fetal calf serum (10%) and streptomycin/penicillin (1%). They were grown to 80% confluence, and then serum starved for 48 hours. The cells were subsequently stimulated with nothing (control), with 1.5 ng/ml of transforming growth factor beta 1 (TGF-β1) (shown as TGF in FIG. 4) for 24 hours (TGF), with 25 μM of a p38 MAP kinase inhibitor, SB 203580 for 2 hours followed by TGF-β1 for 24 hours (TGF+SB), or with 60 μM test polypeptide WLRRIKAWL-RRIKA-LNRQLGVAA (BIP) (SEQ ID NO: 54) for 2 hours followed by TGF-β1 for 24 hours (TGF+BIP). The phosphorylation of HSP27 was assessed by immunoblot analysis using antibodies against phospho-HSP27 (ser 78/82), HSP27, and P actin as a loading control. These data are shown in FIG. 4A. The ratio of phospho-HSP27 to HSP27 was calculated, and the percent phosphorylation was determined with respect to the phosphorylation obtained with TGF-β1 (TGF). These data are shown in FIG. 4B. These data further demonstrate that BIP effectively inhibited phosphorylation of HSP27.

Figure 5:
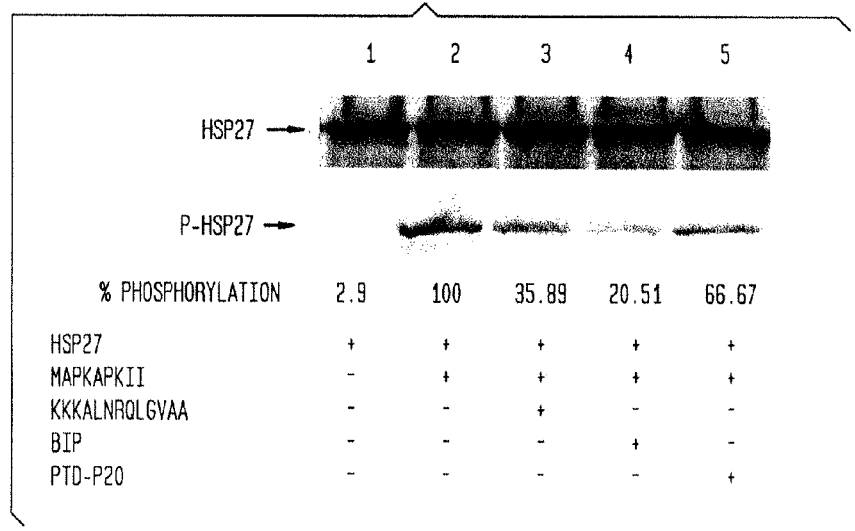
FIG. 5: Data graph showing that HSP27 kinase inhibitor peptide (BIP) (SEQ ID NO: 54) inhibits in vitro phosphorylation of HSP27 by MAPKAP kinase 2.

Example 5 HSP27 Kinase Inhibitor Peptide (BIP) Inhibits Phosphorylation of HSP27 In Vitro Recombinant HSP27 (1 μg) was phosphorylated with no enzyme (control, lane 1), MAPKAP kinase 2 (MAPKAP-KII) (50 ng) in the absence (lane 2) or presence of 200 KKKALNRQLGVAA (SEQ ID NO: 72) (published by Hayess and Benndorf) obtained from Calbiochem (lane 3), BIP (HSP27 kinase inhibitor peptide, WLRRIKAWLR-RIKALNRQLGVAA (SEQ ID NO: 54) (lane 4), or HSP20 phosphopeptide (PTD-P20, lane 4) for 30 min at 30° C. The reaction mixtures were inactivated and separated by SDS-PAGE and transferred to PVDF membrane. The blot was probed with antibodies against HSP27 and phospho-HSP27. The ratio of phospho-HSP27 to HSP27 was calculated, and the percent phosphorylation was determined with respect to the phosphorylation obtained in the absence of inhibitor (lane 2). The data is shown in FIG. 5. This blot is a representative of 2 separate experiments. These data demonstrate that BIP inhibits MAPKAPKII induced phosphorylation of HSP27 in vitro.

Figure 6:
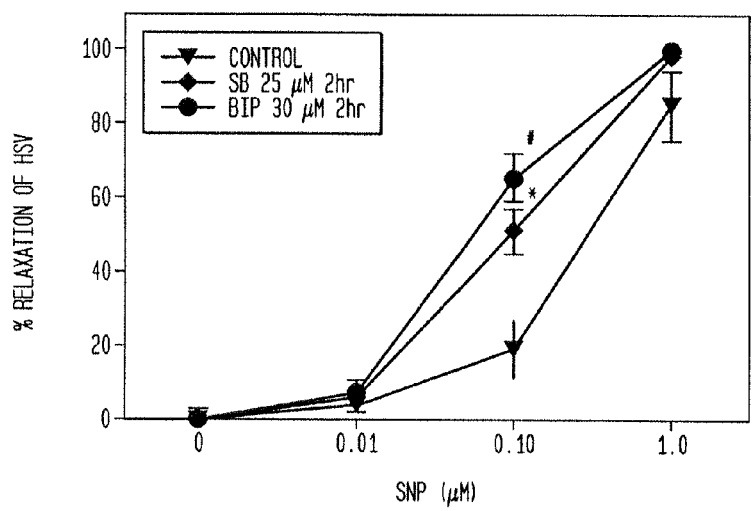
FIG. 6: Data graph showing HSP27 kinase inhibitor peptide (BIP) (SEQ ID NO: 54) enhances sodium nitroprusside-induced relaxation of human saphenous vein.

Experiments with Polypeptide WLRRIKAWLRRIKA-LNRQLGVAA (SEQ ID NO: 54, "BIP") in an In Vitro Model of Intimal Hyperplasia:

Example 6 the p38 MAP Kinase Inhibitor, SB 203580 and HSP27 Kinase Inhibitor, BIP, Enhance Sodium Nitroprusside Induced Relaxation of Saphenous Vein Segments of human saphenous vein (HSV) were equilibrated in a muscle bath and pretreated with buffer (control), 25 μM SB203580 (SB) or 30 μM WLRRIKAWLRRIKA-LNRQLGVAA (BIP) (SEQ ID NO: 54) for 2 hours and then contracted with norepinephrine (NE, 0.5 μM) and relaxed with increasing doses of sodium nitroprusside (SNP, 0-1 μM). The results are shown in FIG. 6. SB or BIP treatment led to significant increases in the relaxation of saphenous vein at 0.1 μM SNP compared to control.

Figure 7:
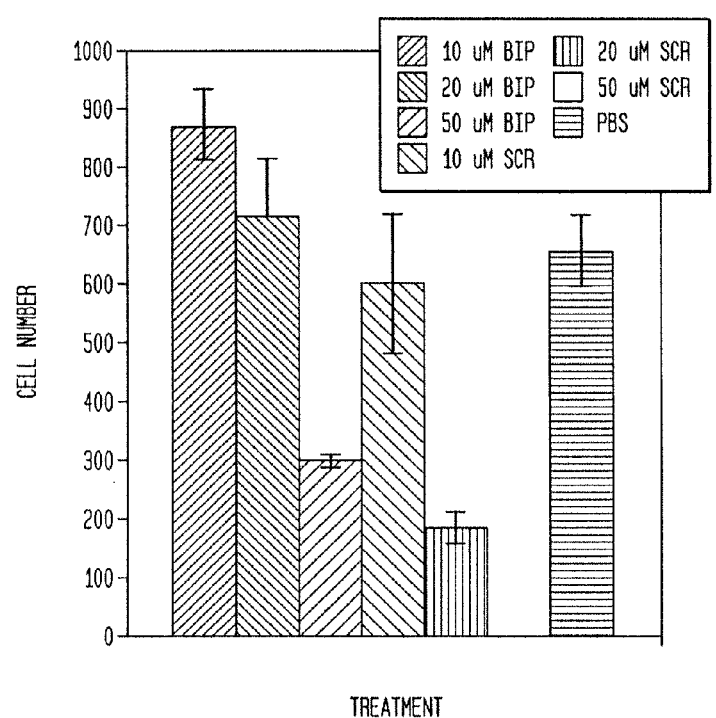
FIG. 7: Data graph showing HSP27 kinase inhibitor peptide (BIP) (SEQ ID NO: 54) does not inhibit endothelial cell proliferation.

Example 7 HSP27 Kinase Inhibitor does not Inhibit Endothelial Cell Proliferation Human Aortic Endothelial Cells (Passage 2) (Cascade Biologies) were seeded into 96-well plates at a concentration of 2000 cells per well as determined using a hemocytometer and allowed to adhere for 4 hours. They were then treated with a final concentration of 1, 10 or 50 μM WLRRIKAWL-RRIKA-LNRQLGVAA (BIP) (SEQ ID NO: 54) 1, 10, or 50 μM scrambled peptide (SCR), or an equal volume of phosphate buffered saline (PBS). Cells were returned to the incubator for 16 hours and counted on a Molecular Devices M5 spectrophotometer after 1 hour treatment with CyQuant NF Cell Proliferation Assay (Invitrogen). Results of the experiment are shown in FIG. 7. These data show that at doses where the polypeptides of the invention suppress CTGF and collagen deposition by Fibroblasts, they do not inhibit endothelial cell proliferation, supporting the hypothesis thAt the polypeptides will be effective at inhibiting intimal hyperplasia and not inhibiting endothelial cell lining if delivered from grafts and stents.

CONCLUSION

Examples 1-7 demonstrate that WLRRIKAWLRRIKA-LNRQLGVAA (BIP) (SEQ ID NO: 54) inhibits TGF-β1 induced expression of CTGF and collagen in human keloid fibroblasts, leads to loss of central actin and reduced stress fiber formation in keloid fibroblasts, inhibits TGF-β1 induced phosphorylation of HSP27 in human keloid fibroblasts, inhibits MAPKAP kinase 2 induced phosphorylation of HSP27 in vitro, and increases the relaxation of saphenous vein. The examples further demonstrate that BIP doses where the polypeptide suppresses CTGF and collagen deposition by fibroblasts do not inhibit endothelial cell proliferation, supporting the hypothesis that the polypeptides will be effective at inhibiting intimal hyperplasia and not inhibiting endothelial cell lining if delivered from grafts and stents.

Example 8 Alanine Scanning Mutagenesis

Amino acids 3-9 of the peptide KALNRQLGVAA (SEQ ID NO: 60) were sequentially replaced with alanine, resulting in the following peptides:

```
                                       (SEQ ID NO: 61)
           KAANRQLGVAA (SEQ ID NO: 62)
           KALARQLGVAA (SEQ ID NO: 63)
           KALNAQLGVAA (SEQ ID NO: 64)
           KALNRALGVAA (SEQ ID NO: 65)
           KALNRQAGVAA
```

KALNRQLAVAA (SEQ ID NO: 66)

KALNRQLGAAA (SEQ ID NO: 67)

These peptides were tested in MAPKAP-K2 kinase inhibition assays and compared to the peptides KALNRQLGVAA (SEQ ID NO: 60), KKKALNRQLGVAA (SEQ ID NO: 72) (Calbiochem), or negative controls.

Briefly, a MAPKAP kinase II assay kit from Invitrogen was used for all assays. Cocktails containing varying inhibitor concentrations, a substrate peptide and kinase were prepared and pipetted into 96-well plates. The plates were placed in an M5 (Molecular Devices) and maintained at 30° C. Readings were taken every 20 seconds for 20 minutes and the resulting reaction velocities were obtained. A summary of the data is presented in Table 1.

TABLE 1

Reaction Velocities for MK2 Inhibitor Variants (n = 3)

| Peptide Sequence | SEQ ID NO: | % of KALNRQLGVAA Reaction Velocity at an Inhibitor Concentration of 100 µM (+/− SEM*) |
| --- | --- | --- |
| KALNRQLGVAA | 60 | 100% (+/− 3%) |
| KALNRQLGVA | 68 | 100% (+/− 3%) |
| KAANRQLGVAA | 61 | 152% (+/− 3%) |
| KALARQLGVAA | 62 | 39% (+/− 1%) |
| KALNAQLGVAA | 63 | 358% (+/− 8%) |
| KALNRALGVAA | 64 | 358% (+/− 15%) |
| KALNRQAGVAA | 65 | 118% (+/− 4%) |
| KALNRQLAVAA | 66 | 72% (+/− 3%) |
| KALNRQLGAAA | 67 | 373% (+/− 13%) |
| KAdLNRQLGVAA | 71 | 146% (+/− 4%) |
| KALdNRQLGVAA | 77 | 95% (+/− 6%) |
| KALNdRQLGVAA | 78 | 306% (+/− 4%) |
| KALNRdQLGVAA | 74 | 276% (+/− 3%) |
| KALNRQdLGVAA | 75 | 357% (+/− 10%) |
| KALNRQLGdVAA | 76 | 260% (+/− 14%) |
| KKKALNRQLGVAA (SEQ ID NO: 72) | Commercially available from Calbiochem | 91% (+/− 4%) |

*SEM = Standard Error of the Mean for three values

All peptides were used at the same concentration. The results of these experiments demonstrated the following in comparison to KALNRQLGVAA (SEQ ID NO: 60).

KAANRQLGVAA (SEQ ID NO: 61): Retains inhibitory activity, but reduced by up to approximately 30%;

KALARQLGVAA (SEQ ID NO: 62): Activity increased by approximately 60% compared to KALNRQLGVAA (SEQ ID NO: 60);

KALNAQLGVAA (SEQ ID NO: 63): Eliminates almost all inhibitory activity;

KALNRALGVAA (SEQ ID NO:64): Eliminates most inhibitory activity;

KALNRQAGVAA (SEQ ID NO:65): Retains inhibitory activity, but reduced by up to approximately 25%;

KALNRQLAVAA (SEQ ID NO: 66): Activity increased by approximately 25% compared to KALNRQLGVAA (SEQ ID NO:60);

KALNRQLGAAA (SEQ ID NO: 67): Eliminates almost all inhibitory activity.

These data indicate that residues 5 (R), 6 (Q), and 9 (V) play a key role in peptide activity.

Experimental results have demonstrated that the C-terminal alanine is not necessary for activity. Alanine substitution at residues 3 and 7 has little effect on inhibitory activity, and thus it is believed that these residues can be substituted with amino acids of similar size. Alanine substitutions at residues 4 and 8 increase activity compared to KALNRQLGVAA (SEQ ID NO: 60), suggesting the substitutions at these positions with small amino acids may increase activity.

Alanine substitutions at residues 5, 6, and 9 have strong effects on inhibitory activity, and thus it is likely that these positions favor very similar amino acids (i.e., size and charge profile) to those present in the starting polypeptide.

HSP27 Kinase Inhibitor Peptides Inhibit LPS-Induced TNF-α Excretion in an In Vitro Model of Inflammation.

HSP27 kinase inhibitor peptides KAF and FAK inhibit LPS-induced TNF-α excretion of THP-1 monocytes. The expression and regulation of cytokines is central to the onset and progression of many disease states including inflammatory disorders and diseases. [Brennan, F. M.; Maini, R. N.; Feldmann, M., Cytokine Expression in Chronic Inflammatory Disease. *British Medical Bulletin* 1995, 51, (2), 368-384.] Although not an exhaustive list, these disease states include rheumatoid arthritis, chronic obstructive pulmonary disease, atherosclerosis, asthma, Crohn's disease, inflammatory bowel disease, osteoarthritis, tendonitis, and psoriasis. One example of a well-studied disease involving cytokine overexpression is rheumatoid arthritis. Rheumatoid arthritis is characterized by chronic inflammation resulting in debilitating consequences ranging from pain and disability to premature mortality. [Jenkins, J. K.; Hardy, K. J.; McMurray, R. W., The pathogenesis of rheumatoid arthritis: A guide to therapy. *American Journal of the Medical Sciences* 2002, 323, (4), 171-180. Pincus, T.; Callahan, L. F., What Is the Natural-History of Rheumatoid-Arthritis. *Rheumatic Disease Clinics of North America* 1993, 19, (1), 123-151. Although the etiology of rheumatoid arthritis remains unknown, the chronic nature of the disease seems to be perpetuated by cytokines and other factors secreted by activated leukocytes recruited to the synovium. [Jenkins, J. K.; Hardy, K. J.; McMurray, R. W., The pathogenesis of rheumatoid arthritis: A guide to therapy. *American Journal of the Medical Sciences* 2002, 323, (4), 171-180. Firestein, G. S.; Zvaifler, N. J., How important are T cells in chronic rheumatoid synovitis? II. T cell-independent mechanisms from beginning to end. *Arthritis and Rheumatism* 2002, 46, (2), 298-308.] Within the synovial joint of patients with rheumatoid arthritis, cytokines including tumor necrosis factor-α (TNF-α), interleukin 1β (IL-1β), IL-6, IL-8, and granulocyte macrophage colony stimulating factor (GM-CSF) have been identified at elevated levels relative to those found in healthy synovial joints. In particular, TNF-α and IL-1β have been implicated as major mediators of inflammation in rheumatoid arthritis, and both greatly influence the expression of other proinflammatory cytokines. [Firestein, G. S.; Zvaifler, N. J., How important are T cells in chronic rheumatoid synovitis? II. T cell-independent mechanisms from beginning to end. *Arthritis and Rheumatism* 2002, 46, (2), 298-308. Feldmann, M.; Brennan, F. M.; Maini, R. N., Role of cytokines in rheumatoid arthritis. *Annual Review of Immunology* 1996, 14, 397-440. Feldmann, M.; Maini, R. N., The role of cytokines in the pathogenesis of rheumatoid arthritis. *Rheumatology* 1999, 38, 3-7.] Produced principally by activated macrophages in the synovial membrane, TNF-α and IL-1β not only stimulate expression of each other but also stimulate fibroblast-like synoviocytes to synthesize and secrete a variety of factors that further progress rheumatic disease. [Jenkins, J. K.; Hardy, K. J.; McMurray, R. W., The pathogenesis of rheumatoid arthritis: A guide to therapy. *American Journal of the Medical Sciences* 2002, 323, (4), 171-180.] During the past decade, a significant body of literature has described more of the intracellular signal transduction pathways implicated in rheumatoid arthritis. Many of these studies have implicated mitogen-activated protein kinases (MAPKs) as enzymes important in the synthesis of inflammatory mediators of many diseases including rheumatoid arthritis. [Saklatvala, J., The p38 MAP kinase pathway as a therapeutic target in inflammatory disease. *Current Opinion in Pharmacology* 2004, 4, (4), 372-377.] In particular, inhibitors of p38 MAP kinase and its downstream target MAPK-activated protein kinase 2 (MAP-KAP kinase 2) have been shown to downregulate production of cytokines such as TNF-α and IL-1β. [Kumar, S.; Boehm, J.; Lee, J. C., p38 map kinases: Key signaling molecules as therapeutic targets for inflammatory diseases. *Nature Reviews Drug Discovery* 2003, 2, (9), 717-726.] Although newer approaches in rheumatoid arthritis drug design have focused on small molecule inhibitors of p38 MAP kinase and to a lesser extent MAPKAP kinase 2, little attention has been given to the development of biologic therapeutics targeting MAPKAP kinase 2. [Gaestel, M.; Mengel, A.; Bothe, U.; Asadullah, K., Protein kinases as small molecule inhibitor targets in inflammation. *Current Medicinal Chemistry* 2007, 14, (21), 2214-2234.] Although many small molecular inhibitors of p38 MAP kinase have reduced TNF-α production in THP-1 cell lines and decreased observed characteristics/symptoms of inflammatory in animal models, p38 MAP kinase knockout mice are not viable, and many of the small molecules have shown side effects including liver toxicity. Since MAPKAP kinase 2 is a substrate of p38 MAP kinase and because MAPKAP kinase 2 knockout mice are viable and have shown decreased production of TNF-α and IL-6, a more selective inhibitor of MAPKAP kinase 2 (also referred to as HSP27 kinase) likely could provide specific inhibition with a decrease in side effects. [Hegen, M.; Gaestel, M.; Nickerson-Nutter, C. L.; Lin, L. L.; Telliez, J. B., MAPKAP kinase 2-deficient mice are resistant to collagen-induced arthritis. *Journal of Immunology* 2006, 177, (3), 1913-1917.] Although the mechanism of action is still unknown, one possibility is that HSP27, a substrate of MAPKAP kinase 2 that can be phosphorylated on serines 15, 78 or 82 (in human) acts to stabilize transcription factors or mRNA related to proinflammatory cytokines synthesis. Also, MAPKAP kinase 2 has been shown to stabilize complexes with p38 involved in maintaining stability of proinflammatory mRNA. [Saklatvala, J., The p38 MAP kinase pathway as a therapeutic target in inflammatory disease. *Current Opinion in Pharmacology* 2004, 4, (4), 372-377. Kumar, S.; Boehm, J.; Lee, J. C., p38 map kinases: Key signaling molecules as therapeutic targets for inflammatory diseases. *Nature Reviews Drug Discovery* 2003, 2, (9), 717-726.] Recent work has implicated MAPKAP kinase 2 as an essential protein for lipopolysaccharide (LPS) induced TNF-α synthesis. [Kotlyarov, A.; Neininger, A.; Schubert, C.; Eckert, R.; Birchmeier, C.; Volk, H. D.; Gaestel, M., MAPKAP kinase 2 is essential for LPS-induced TNF-alpha biosynthesis. *Nature Cell Biology* 1999, 1, (2), 94-97.]

THP-1 monocytes are used routinely as a model cell line for induction of cytokines upon stimulation with lipopolysaccharide (LPS). Cytokine excretion can be enhanced further when the cells are first differentiated with phorbol 12-myristate 13-acetate (PMA) into macrophage-like cells. [Auwerx, J., The Human Leukemia-Cell Line, Thp-1—a Multifaceted Model for the Study of Monocyte-Macrophage Differentiation. *Experientia* 1991, 47, (1), 22-31.] THP-1 monocytes and LPS-induced THP-1 monocytes have been used as a model to study efficacy of antimicrobial agents, [Takemura, H.; Yamamoto, H.; Kunishima, H.; Ikejima, H.; Hara, T.; Kanemitsu, K.; Terakubo, S.; Shoji, Y.; Kaku, M.; Shimada, J., Evaluation of a human monocytic cell line THP-1 model for assay of the intracellular activities of antimicrobial agents against *Legionella pneumophila. Journal of Antimicrobial Chemotherapy* 2000, 46, (4), 589-594] general toxicity of compounds, [Sestier, C.; Lacava, Z. G. M.; Lacava, L. M.; Da Silva, M. F.; Azevedo, R. B.; Buske, N.; Gansau, C.; Morais, P. C.; Silva, O.; Pelegrini, F.; Sabolovic, D., In vitro toxicity of magnetic fluids evaluated for macrophage cell lines. *Journal of Magnetism and Magnetic Materials* 2002, 252, (1-3), 403-405.], and especially as models of activated macrophages. [Auwerx, J., The Human Leukemia-Cell Line, Thp-1—a Multifaceted Model for the Study of Monocyte-Macrophage Differentiation. *Experientia* 1991, 47, (1), 22-31.] With regard to applications involving inflammation, THP-1 cells have often been used as a model system to investigate efficacy of anti-inflammatory agents including p38 kinase inhibitors. [Ross, S.; Chen, T.; Yu, V.; Tudor, Y.; Zhang, D. W.; Liu, L. B.; Tamayo, N.; Dominguez, C.; Powers, D., High-content screening analysis of the p38 pathway: Profiling of structurally related p38 alpha kinase inhibitors using cell-based assays. *Assay and Drug Development Technologies* 2006, 4, (4), 397-409.] Often, excreted cytokine levels are compared between controls and treatments containing anti-inflammatory agents to determine drug efficacy.

Phorbol 12-myristate 13-acetate ("PMA") is a potent tumor promote that activates the signal transduction enzyme protein kinase C ("PKC"). PKC phosphorylates proteins altering their function. Its effects are cell-specific.

Figure 8:
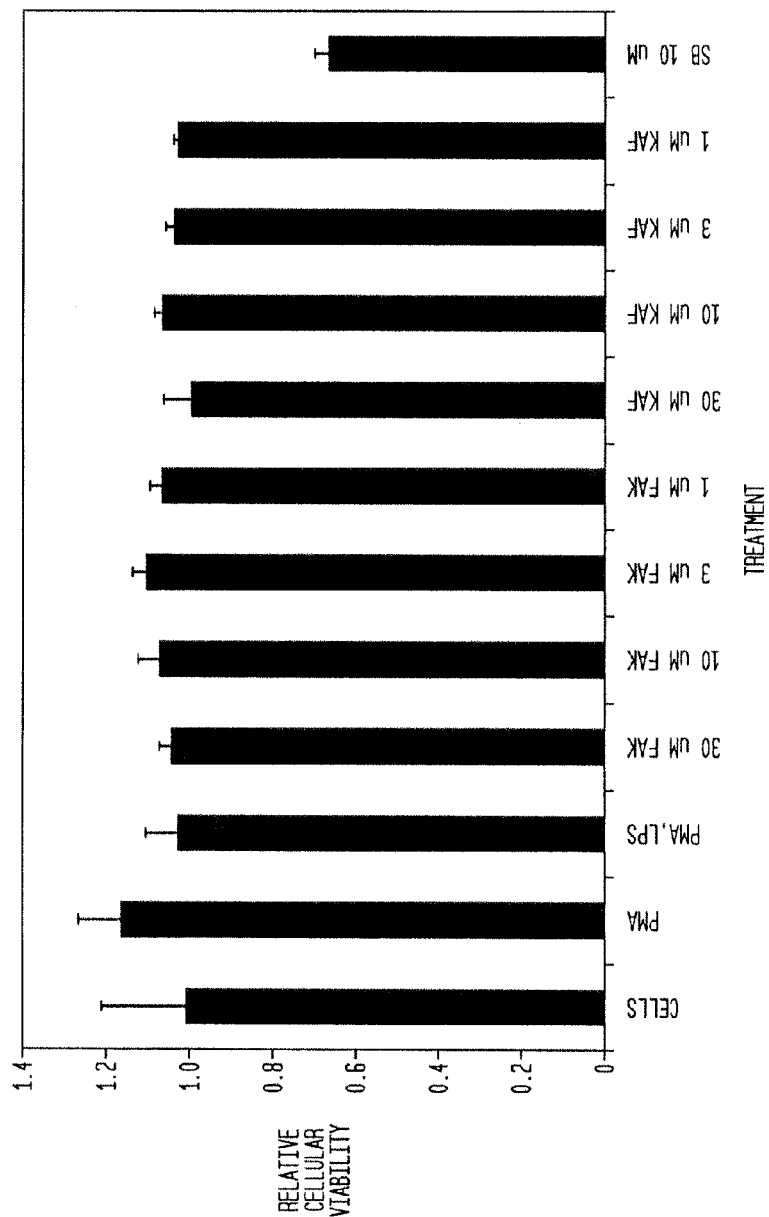
FIG. 8: Data graph showing cellular viability of LPS-induced THP-1 monocytes treated with HSP27 kinase inhibitor peptides KAF (SEQ ID NO: 48) and FAK (SEQ ID NO: 49).
Figure 9:
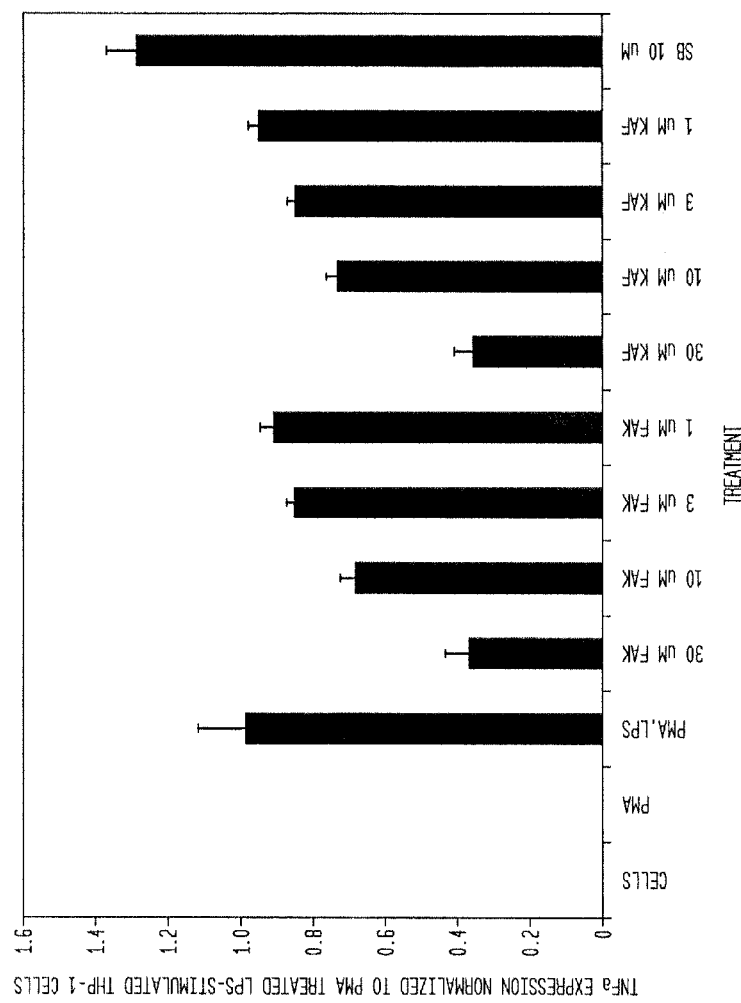
FIG. 9: Data graph showing that HSP27 kinase inhibitor peptides KAF (SEQ ID NO: 48) and FAK (SEQ ID NO: 49) inhibit LPS-induced TNF-α excretion of THP-1 monocytes.

Example 9 HSP27 Kinase Inhibitor Peptide KAF and FAK Inhibit LPS-Induced TNF-α Excretion in an In Vitro Model of Inflammation Human THP-1 monocytes were maintained in RPMI 1640 supplemented with fetal bovine serum (10%), streptomycin/penicillin (1%), 0.05 mM β-mercaptoethanol, 1 mM sodium pyruvate, and 10 mM HEPES. They were seeded at a density of 250,000 cells/ml and treated with 200 nM phorbol 12-myristate 13-acetate (PMA) for 20 hours. One cohort was not treated with PMA as a control (cells). Then, cells were treated with one of the following treatments: no treatment and no PMA (cells), no treatment (PMA), 100 ng/ml lipopolysaccharide (LPS) (PMA, LPS), 100 ng/ml LPS with 10 µM SB203580 (SB), or 100 ng/ml LPS with various concentrations of HSP27 kinase inhibitor peptides. The inhibitor peptides were KAFAKLAARLYRKALARQLGVAA (KAF) (SEQ ID NO: 48) and FAKLAARLYRKALARQL-GVAA (FAK) (SEQ ID NO: 49), and the treatment concentrations were 30 µM (KAF 30 µM or FAK 30 µM), 10 µM (KAF 10 µM or FAK 10 µM), 3 µM (KAF 3 uM or FAK 3 uM), and 1 (µM (KAF 1 µM or FAK 1 µM). After applying the treatments, the cells were grown for 6 hours at 37° C. and 5% $CO_2$. Then, the cells were centrifuged, and TNF-α concentration in the supernatant was determined by ELISA. Viability of centrifuged cells was determined using an MTT-based assay. Results of cellular viability presented in FIG. 8 represent average±standard deviation of four replicates. Results of relative TNF-α excretion presented in FIG. 9 represent average±standard deviation of four replicates. These results demonstrate that KAF and FAK inhibit LPS-induced TNF-α excretion from monocytes in a dose dependent manner without adversely affecting cellular viability.

Figure 10:
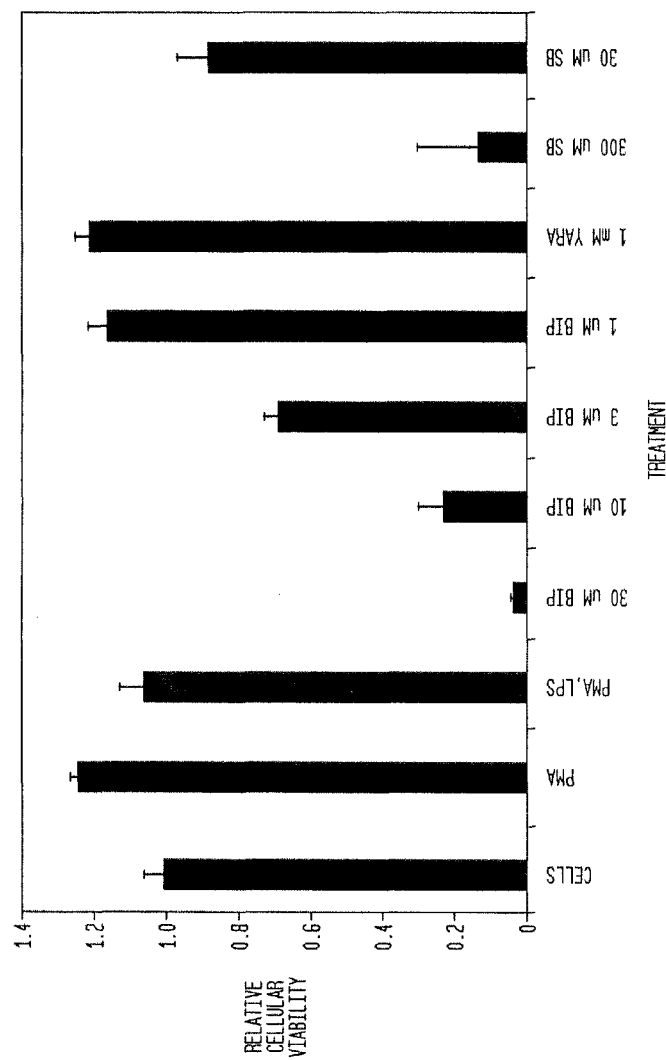
FIG. 10: Data graph showing cellular viability of LPS-induced THP-1 monocytes treated with HSP27 kinase inhibitor peptides BIP (SEQ ID NO: 54) and YARA ("YARA" disclosed as SEQ ID NO: 73, YARA full-length peptide disclosed as SEQ ID NO: 55).
Figure 11:
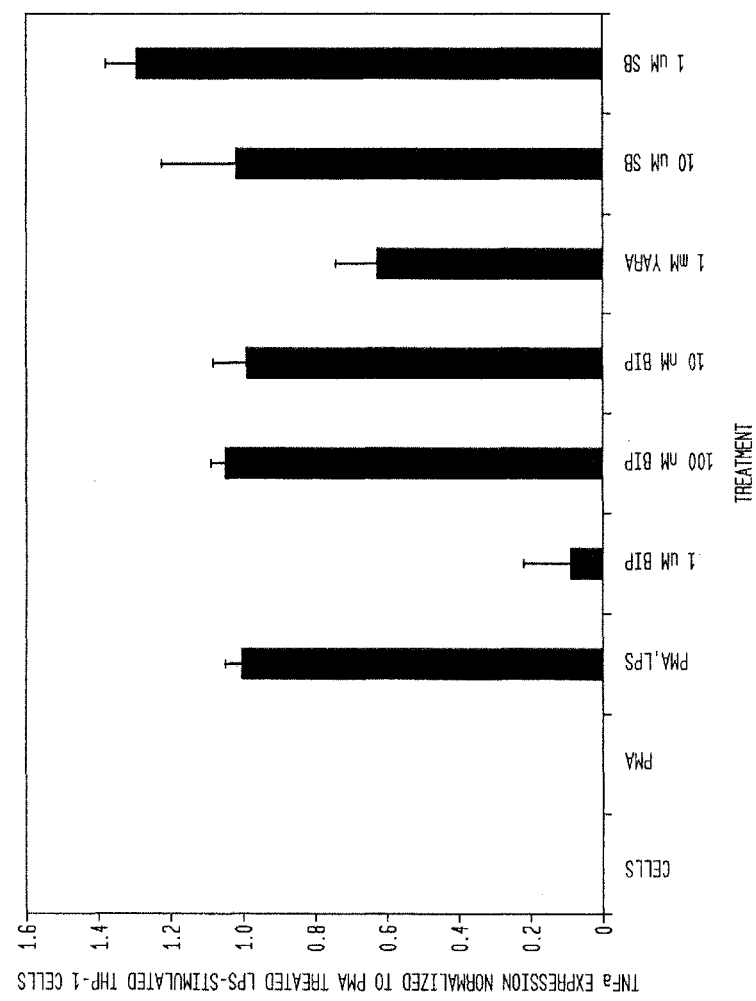
FIG. 11: Data graph showing that HSP27 kinase inhibitor peptides BIP (SEQ ID NO: 54) and YARA ("YARA" disclosed as SEQ ID NO: 73, YARA full-length peptide disclosed as SEQ ID NO: 55) inhibit LPS-induced TNF-α excretion of THP-1 monocytes.

Example 10 HSP27 Kinase Inhibitor Peptides BIP and YARA (SEQ ID NO: 73) Inhibit LPS-Induced TNF-α Excretion of THP-1 Monocytes Human THP-1 monocytes were maintained in RPMI 1640 supplemented with fetal bovine serum (10%), streptomycin/penicillin (1%), 0.05 mM β-mercaptoethanol, 1 mM sodium pyruvate, and 10 mM HEPES. They were seeded at a density of 250,000 cells/ml and treated with 200 nM phorbol 12-myristate 13-acetate (PMA) for 20 hours. One cohort was not treated with PMA as a control (cells). Then, cells were treated with one of the following treatments: no treatment and no PMA (cells), no treatment (PMA), 100 ng/ml lipopolysaccharide (LPS) (PMA, LPS), 100 ng/ml LPS with 300 μM, 30 μM, 10 μM, or 1 μM SB203580 (SB), or 100 ng/ml LPS with various concentrations of HSP27 kinase inhibitor peptides. The inhibitor peptides were WLRRIKAWLR-RIKALNRQLGVAA (BIP) (SEQ ID NO: 54) and YARAAARQARAKALNRQLGVA (YARA ("YARA" disclosed as SEQ ID NO: 73)) (SEQ ID NO: 55). For BIP, the treatment concentrations were 30 μM, 10 μM, 3 μM, 1 μM, 100 nM, and 10 nM. For YARA (SEQ ID NO: 73), the treatment concentration was 1 mM. After applying the treatments, the cells were grown for 6 hours at 37° C. and 5% $CO_2$. Then, the cells were centrifuged, and TNF-α concentration in the supernatant was determined by ELISA. Viability of centrifuged cells was determined using an MTT-based assay. Results of cellular viability presented in FIG. 10 represent average±standard deviation of four replicates. Results of relative TNF-α excretion presented in FIG. 11 represent average±standard deviation of four replicates. These results demonstrate that BIP and YARA (SEQ ID NO: 73) can be used at concentrations which inhibit LPS-induced TNF-α excretion from monocytes without adversely affecting cellular viability.

Experiments in an In Vitro Model for Gliosis and Scar Formation in the Central Nervous System Primary astrocyte cultures are an appropriate in vitro model for gliosis and scar formation in the central nervous system. Astrocytes are the primary cell type implicated in gliosis and scar formation in the central nervous system. Gliosis and scar formation are believed to be triggered by cytokines including TGF-β1, IL6 and TNF-α and serum derived factors including LPA and endothelins. Their activity is propagated by cyclic nucleotide-dependent signaling resulting in p38 MAP kinase activation followed by MAP-KAP kinase II (MK2) activation. Yang, et al. demonstrated that three cytokines, IL-1β, IL-6 and TNF-α play roles both in spinal cord tissue regeneration and in tissue damage. They further suggest that low levels of expression are likely to be beneficial to tissue maintenance and regeneration, but higher levels of expression are detrimental [Yang, L. L., et al., *Early expression and cellular localization of proinflammatory cytokines interleukin-1 beta, interleukin-6, and tumor necrosis factor-alpha in human traumatic spinal cord injury.* Spine, 2004. 29(9): p. 966-71.] Multiple studies suggest that over expression of these cytokines leads to exacerbated secondary injury [Yang, L. L., et al., *Early expression and cellular localization of proinflammatory cytokines interleukin-1 beta, interleukin-6, and tumor necrosis factor-alpha in human traumatic spinal cord injury.* Spine, 2004. 29(9): p. 966-71. Velardo, M. J., et al., *Patterns of Gene Expression Reveal a Temporally Orchestrated Wound Healing Response in the Injured Spinal Cord.* J. Neurosci., 2004. 24(39): p. 8562-8576. Bareyre, F. M. and M. E. Schwab, *Inflammation, degeneration and regeneration in the injured spinal cord: insights from DNA microarrays.* Trends Neurosci, 2003. 26(10): p. 555-63. Pineau, I. and S. Lacroix, *Proinflammatory cytokine synthesis in the injured mouse spinal cord: multiphasic expression pattern and identification of the cell types involved.* J Comp Neurol, 2007. 500(2): p. 267-85.] [Yang, L. L., et al., *Early expression and cellular localization of proinflammatory cytokines interleukin-1 beta, interleukin-6, and tumor necrosis factor-alpha in human traumatic spinal cord injury.* Spine, 2004. 29(9): p. 966-71. Velardo, M. J., et al., *Patterns of Gene Expression Reveal a Temporally Orchestrated Wound Healing Response in the Injured Spinal Cord.* J. Neurosci., 2004. 24(39): p. 8562-8576. Bareyre, F. M. and M. E. Schwab, *Inflammation, degeneration and regeneration in the injured spinal cord: insights from DNA microarrays.* Trends Neurosci, 2003. 26(10): p. 555-63. Pineau, I. and S. Lacroix, *Proinflammatory cytokine synthesis in the injured mouse spinal cord: multiphasic expression pattern and identification of the cell types involved.* J Comp Neurol, 2007. 500(2): p. 267-85.], while, as discussed above, complete depletion of cytokine signaling can lead to a decrease in neuronal survival [Iwasaki, Y., et al., *Effect of transforming growth factor beta 1 on spinal motor neurons after axotomy.* J Neurol Sci, 1997. 147(1): p. 9-12. Silver, J. and J. H. Miller, Regeneration beyond the glial scar. Nature Reviews Neuroscience, 2004. 5(2): p. 146-156.]. The approach proposed herein inhibits MK2 and thus down-regulates expression of inflammatory cytokines due to traumatic brain injury and spinal cord injury.

Example 11. HSP27 Kinase Inhibitor Peptide KAF Decreases Phosphorylation of HSP27 in Astrocytes Even in the Presence of TNF-α

Figure 12:
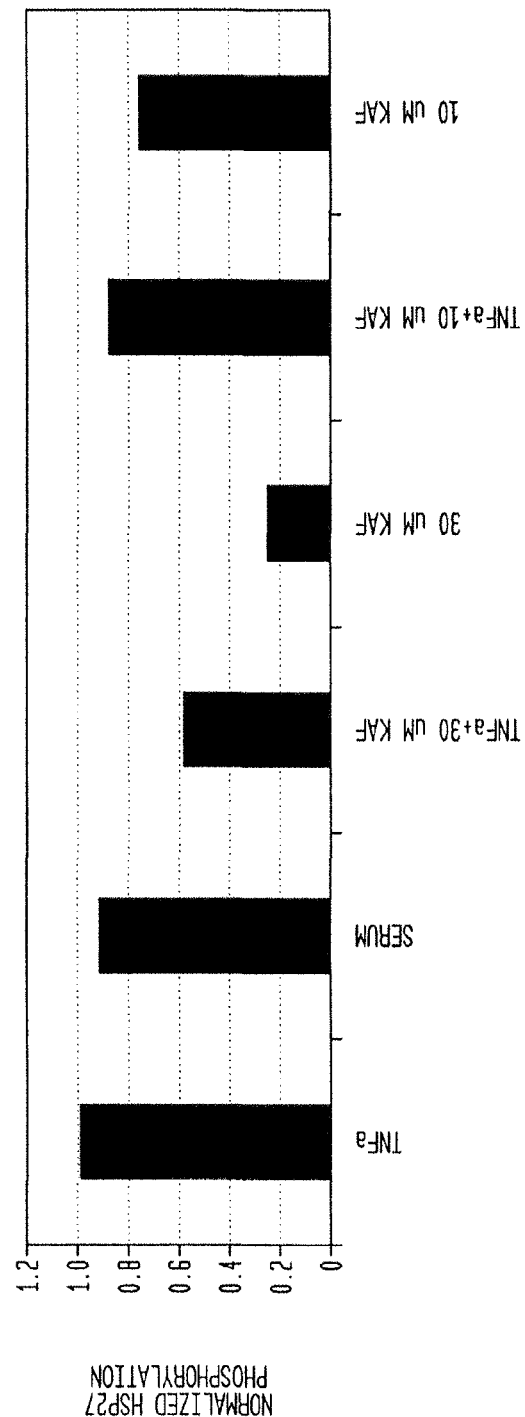
FIG. 12: Data graph showing that HSP27 kinase inhibitor peptide KAF (SEQ ID NO: 48) decreases phosphorylation of HSP27 in astrocytes even in the presence of TNF-α.

Primary rat astrocytes were isolated from cortical E19 rat brain tissue (BrainBits, LLC) following the protocol suggested by Brain Bits. Cells were resuspended in Neurobasal media containing 10% serum and 3 mM glutamine and plated at a density of 75,000 cells/cm² in 10-cm Petri dishes. Once confluent, cells were passaged twice with a 3:1 split prior to treatment. Cells were then treated with 5 ng/ml TNF-α to activate them. Negative controls were untreated, positive controls treated with TNF-α alone, and two dishes were treated with KAF (SEQ ID NO: 48) at 10 μM or 30 μM. 24 hours after treatment, media was removed, cells washed with PBS and lysed. Lysates were run on SDS-PAGE followed by transfer to PVDF membrane and western blot probing for phosphorylated HSP27. GAPDH was used as a loading control. The results of this experiment are shown in FIG. 12. These results demonstrate that KAF (SEQ ID NO: 48) decreases phosphorylation of HSP27 in astrocytes even when the astrocytes are challenged with TNF-α.

Animal Studies

In another aspect, the present invention further describes experiments in animal models of human disease that will be used to determine the effect of the polypeptides of the present invention. These animal models have been used by other investigators, and are generally accepted as such. The therapeutic results obtained with this model therefore can be extrapolated to methods of treating human subjects.

Animal Models

Intestinal adhesions model. Animal Studies will be carried out in the AAALAC accredited animal facilities at Purdue University in accordance with the National Institutes of Health Guide for Care and Use of Animals. Male Sprague-Dawley rat weighing between 240-280 g will be included in the study. The cohorts have been designed to include a positive control, cecum abrasion, no treatment, and a negative control, no abrasion, no treatment, as well as additional cohorts to evaluate the optimal delivery method to prevent intestinal adhesions. All animals will be maintained in separate cages under a 12 hour light/dark cycle and provided food and water ad libitum both before and following surgery. All animals will be anesthetized using an intra peritoneal injection of ketamine (75-100 mg/kg) and xylazine (5-10 mg/kg). Anesthesia will be maintained with an intra peritoneal injection of 10% induction dose of ketamine/xylazine. Anesthetic levels will be assessed using the toe pinch method. Also, the animal's respiration and color of mucous membrane will be monitored during the procedure. Animals will be euthanized using barbiturate overdose (e.g., Nembutal 120 mg/kg) or similar commercially available euthanasia solution at the recommended dosage IV or IP.

Anesthetized rats will be prepped for surgery by shaving the lower abdomen and cleaning it with iodine. Animals will undergo a midline celiotomy, the cecum will be identified and placed onto a gauze pad and saline used to keep the tissue moist. The cecum wall will be abraded using 1×1 cm electrosurgical tip cleaner, Johnson and Johnson, until bleeding is noted on the anterior surface. A 1.6×0.8 mm defect will be created in the peritoneum and underlying muscle using a 0.8 mm biopsy punch. The abdominal cavity will be irrigated prior to application of treatments. The appropriate treatment will be applied between the juxtaposed cecum and injured peritoneum. Specifically, in cohort 1 the abraded cecum will be juxtapose to the injured peritoneum and the surgical incision closed. Cohort 2 be subjected to only the celiotomy and the incision will be closed. Additional cohorts will be irrigated with 10 mls of PBS containing the appropriate concentration, of MK2 inhibitor If injury such as a perforated bowel occurs during surgery or the barrier fails to separate the damaged tissue, the animal will be removed from the study and replaced [Buckenmaier, C. C., 3rd, et al., Comparison of antiadhesive treatments using an objective rat model. Am Surg, 1999. 65(3): p. 274-82; Zong, X., et al., Prevention of postsurgery-induced abdominal adhesions by electrospun bioabsorbable nanofibrous poly(lactide-co-glycolide)-based membranes. Ann Surg, 2004. 240(5): p. 910-5].

Fourteen days post-surgery the rats will again be anesthetized as described above and a surgeon who is blinded to the treatments will perform a second celiotomy to evaluate the extent and severity of the adhesions. The vast majority of abdominal adhesion studies use a visual analogue scoring system rather than histology. The following scoring system will be used: 0=no adhesions, 1=thin and filmy, easily separated adhesions, 2=significant and filmy, difficult to separate tissue and 3=severe with fibrosis, instruments required to separate tissue. The number of animals within each group with adhesions and the severity of adhesions will be noted and then compared across groups using ANOVA analysis to determine the best treatment combination (barrier, rate of release and drug concentration) to inhibit adhesions.

Wound Healing/Scar Inhibition

Rat model of dermal scarring. A Sprague-Dawley model of scarring will be used. All protocols will have Institutional Animal Care and Use Committee approval. A mixture of male and female animals will between 240-280 g will be used. The animals will be anesthetized using mouse ketamine cocktail (2 ml/kg, 21 mg/ml ketamine, 2.4 mg/ml xylazine, and 0.03 mg/ml acepromazine). The area on the back will be shaved with surgical clippers and scrubbed with Chlorhexidine surgical scrub. A single linear incision 2 cm in length extending through the dermis, epidermis, and into the subcutaneous fat will be made on the upper back. The incision will be closed with interrupted 4-0 nylon sutures. Treatment with 0.1 ml of increasing concentrations from 0.01 mM to 1 mM MK2i or saline vehicle will be subcutaneously injected on each side of the incision immediately after closure (n=7-8 animals per group). Control groups will have incisions, but no peptide treatment. Sutures will be removed after 1 week, and animals were euthanized at 7, 14, and 21 days post surgery by inhalation of carbon dioxide. At termination, the healing wounds and adjacent skin (as a control) will be excised. The tissue will be placed in formalin, embedded in paraffin, and processed for histologic sectioning and Masson's trichrome staining. Each trichrome-stained specimen will be blindly scored in duplicate by a pathologist for dermal collagen fiber orientation, density, and maturity.

Arthritis Models

Accepted in vivo animal models for rheumatoid arthritis include collagen-induced arthritis (CIA), rat carrageenin-induced acute model of inflammation, adjuvant-induced arthritis in rats (AA), and streptococcal cell wall-induced arthritis. Each of these models have been used to test compounds inhibiting expression, excretion, and/or activity of inflammatory cytokines. However, CIA is the murine model most commonly used.

For collagen-induced arthritis (CIA), mice (6-8 weeks old) will be injected in the base of the tail with 0.1 ml of a mixture of bovine type II and complete Freund's adjuvant containing heat-killed *Mycobacterium tuberculosis*. After 21 days, a 0.1 ml of collagen type II in phosphate buffered saline (PBS) will be given as an injection to the base of the tail as a booster. (Hegen, M.; Gaestel, M.; Nickerson-Nutter, C. L.; Lin, L. L.; Telliez, J. B., MAPKAP kinase 2-deficient mice are resistant to collagen-induced arthritis. Journal of Immunology 2006, 177, (3), 1913-1917; Yamanishi, Y.; Boyle, D. L.; Pinkoski, M. J.; Mahboubi, A.; Lin, T.; Han, Z. N.; Zvaifler, N. J.; Green, D. R.; Firestein, G. S., Regulation of joint destruction and inflammation by p53 in collagen-induced arthritis. American Journal of Pathology 2002, 160, (1), 123-130; Podolin, P. L.; Callahan, J. F.; Bolognese, B. J.; Li, Y. H.; Carlson, K.; Davis, T. G.; Mellor, G. W.; Evans, C.; Roshak, A. K., Attenuation of murine collagen-induced arthritis by a novel, potent, selective small molecule inhibitor of I kappa B kinase 2, TPCA-1 (2-[(aminocarbonyl)amino]-5-(4-fluorophenyl)-3-thiophenecarboxamide), occurs via reduction of proinflammatory cytokines and antigen-induced T cell proliferation. Journal of Pharmacology and Experimental Therapeutics 2005, 312, (1), 373-381). HSP27 kinase inhibitor in PBS will be injected into the synovial joint of the hind limb. Control animals will receive an injection of PBS without inhibitor. Injections will begin once an animal has obtained a clinical score greater or equal to "1" for two consecutive days. Assessment of the arthritic state of the mice will be assessed using clinical arthritis scores of 0 (no arthritis), 1 (ankle swelling), 2 (ankle and midfoot swelling), 3 (ankle, midfoot, and metatarsal joint swelling), and 4 (ankle, midfoot, metatarsal joint, and digit swelling). (Yamanishi, Y.; Boyle, D. L.; Pinkoski, M. J.; Mahboubi, A.; Lin, T.; Han, Z. N.; Zvaifler, N. J.; Green, D. R.; Firestein, G. S., Regulation of joint destruction and inflammation by p53 in collagen-induced arthritis. American Journal of Pathology 2002, 160, (1), 123-130; Podolin, P. L.; Callahan, J. F.; Bolognese, B. J.; Li, Y. H.; Carlson, K.; Davis, T. G.; Mellor, G. W.; Evans, C.; Roshak, A. K., Attenuation of murine collagen-induced arthritis by a novel, potent, selective small molecule inhibitor of I kappa B kinase 2, TPCA-1 (2-[(aminocarbonyl)

amino]-5-(4-fluorophenyl)-3-thiophenecarboxamide), occurs via reduction of proinflammatory cytokines and antigen-induced T cell proliferation. Journal of Pharmacology and Experimental Therapeutics 2005, 312, (1), 373-381). Scoring of the contralateral hind limb will also be performed. Samples of synovial fluid will be taken regularly for analysis of cytokine concentrations. After sacrificing the mice, hind limbs will be fixed in formalin and processed for histology to examine inflammation and hyperplasia. (Yamanishi, Y.; Boyle, D. L.; Pinkoski, M. J.; Mahboubi, A.; Lin, T.; Han, Z. N.; Zvaifler, N. J.; Green, D. R.; Firestein, G. S., Regulation of joint destruction and inflammation by p53 in collagen-induced arthritis. American Journal of Pathology 2002, 160, (1), 123-130.)

Spinal Cord Models

Spinal cord experiments: Sprague Dawley rats (200-300 gm) will be subjected to spinal cord injury using transection (Widenfalk, Lundstromer et al. 2001). Following halothane anesthesia, dorsal laminectomies at T9 expose the cord. Complete transection leaving a 2 mm gap will be achieved using an iris scalpel. Peptide concentrations ranging from 0.01-1 mM peptide or saline (control) will be applied to the injured cord is achieved using 50-100 µl volumes. Closure will be done using absorbable suture material, and the animals recover on warmed blankets. Prophylactic antibiotics will be administered for one week, and subsequently if needed. Urinary bladders will be emptied thrice daily by mechanical expression for the first week, and twice daily thereafter to prevent urinary tract infections. Animals will be sacrificed at two time points to provide assessment of the onset and sustained regeneration of axons (typically in cohorts of 6 and 16 on days 7 and 56 respectively. The day 7 time allows determination of the extent of proliferation of astrocytes and if there is a chronic immune response. Day 56 will provide information on axonal regeneration (Coumans, J. V., T. T.-S. Lin, et al. (2001). "Axonal regeneration and functional recovery after complete spinal cord transection in rats by delayed treatment with transplants and neurotrophins." The Journal of Neuroscience 21(23): 9334-9344). A larger number of animals is needed for day 56 animals so that longitudinal and axonal sectioning as well as neuroanatomical tracing can be done (Woerly, Doan Woerly, S., V. D. Doan, et al. (2001). "Spinal cord reconstruction using Neurogel™ Implants and functional recovery after chronic injury." Journal of Neuroscience Research 66: 1187-1197).

Spinal Cord Histology:

Animals will be euthanized by CO2 inhalation according to AVMA recommendations (Andrews, E. J., B. T. Bennett, et al. (1993). "Report of the AVMA panel on Euthanasia." Journal of the American Veterinary Association 202(2): 229-249). Cardiac perfusion using 2% paraformaldehyde in PBS, followed by 10% sucrose precedes cord dissection to optimize histology (Andrew, D. and A. D. Craig, Spinothalamic lamina I neurons selectively sensitive to histamine: a central neural pathway for itch. Nature Neuroscience, 2001. 4(1): p. 72-77.). From the four animals not receiving neural tracing, the cord in the region of injury will be recovered, then processed by longitudinal cryostat sectioning (14 µm) along the injured axis. For assessment of proliferative cells in the injury site, anti-PCNA antibodies are applied according to supplier's instruction. Cell-type staining for occupation of the matrix in the context of spinal repair will include astrocytes (glial fibrillary acidic protein, GFAP), oligodendrocytes (myelin proteolipid protein, mPLP), neurons (neuron specific enolase, NSE), GAP-43 (found in the growth cone of extending axons), monocytes/macrophages (CD45), lymphocytes (CD16), and endothelial cells (factor VIII).

Cervical Contusion Injury.

A contusion injury will be created using an electromagnetic SCI device. Animals will first be anesthetized and then a vertical incision will be made along the cervical vertebra and the superficial muscle and skin retracted. A laminectomy will be used to expose at cervical vertebra C5 and the spinal cord underneath (C5) while maintaining an intact dura mater. The cervical contusion injury will be created with a force of 3 Kdyn. The exposed C5 spinal cord will be rated as either mildly, moderately or severely injured as determined by displacement of the spinal cord by 0.80, 0.95, or 1.10 mm, respectively, with a single, brief displacement of 20 msec. After injury, the muscles and skin will be sutured in layers. The rats will recover in a warmed cage with water and food easily accessible. Gentamicin (5 mg/kg, intramuscular) will be administered immediately post-surgery and then daily for seven days. The analgesic, Buprenex (0.01 mg/kg of 0.3 mg/mL, subcutaneous;) will be delivered post-surgery and daily for 2 days to minimize animal discomfort. The rats were maintained for 1 week or 9 weeks after injury. For each time point and severity of injury, 20 animals will be treated and 10 animals will serve as controls. Harvested tissues will be examined for cavitation, gliosis and axonal regeneration.

While the present invention has been described with reference to the specific embodiments thereof, it should be understood by those skilled in the art that various changes may be made and equivalents may be substituted without departing from the true spirit and scope of the Invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for treating a disease, disorder or a condition in a subject in need thereof characterized by inhibiting excretion of TNF-α from monocytes selected from the group consisting of intimal hyperplasia, Crohn's disease, inflammatory bowel disease, and psoriasis, the method comprising the step of:
administering a therapeutic amount of a composition comprising an isolated polypeptide and a pharmaceutically acceptable carrier;
wherein the polypeptide comprises a sequence Z1-X1-X2-X3-X4-X5-X6-X7-X8-X9-X10-Z2 (Formula I) (SEQ ID NO: 69);
wherein Z1 and Z2 are independently absent or are transduction domains; and
wherein X1-X2-X3-X4-X5-X6-X7-X8-X9-X10 is an amino acid sequence
selected from the group consisting of the amino acid sequence KALARQLGVAA (SEQ ID NO: 62), the amino acid sequence KALNRQLAVAA (SEQ ID NO: 66), and the amino acid sequence KALNRQLGVA (SEQ ID NO: 68).

2. The method according to claim 1, further comprising the steps of monitoring a level of at least one biomarker in a target tissue, wherein the at least one biomarker is selected from the group consisting of: TGF01 expression; collagen I expression; CTGF expression; a-smooth muscle actin expression; TNF-α; IL-1; IL-6; IL-8; COX-2; MIP-1α; and MIP-2; and
maintaining the level of the biomarker in the target tissue substantially at normal levels during treatment.

3. The method of claim 1, wherein the polypeptide is KAFAKLAARLYRKALARQLGVAA (SEQ ID NO: 48).

4. The method of claim 1, wherein the polypeptide is FAKLAARLYRKALARQLGVAA (SEQ ID NO: 49).

5. The method of claim 1, wherein the polypeptide is YARAAARQARAKALNRQLGVA (SEQ ID NO. 55).

* * * * *

SEQUENCE LISTING

```
<160> NUMBER OF SEQ ID NOS: 78

<210> SEQ ID NO 1
<211> LENGTH: 9
<212> TYPE: PRT
<213> ORGANISM: Unknown
<220> FEATURE:
<223> OTHER INFORMATION: Mammalian Peptide
<220> FEATURE:
<221> NAME/KEY: MISC_FEATURE
<222> LOCATION: (1)..(9)
<223> OTHER INFORMATION: This sequence may encompass 4 to 9 "Arg"
      residues, wherein residues from positions 5 to 9 may be absent
```

```
<400> SEQUENCE: 1

Arg Arg Arg Arg Arg Arg Arg Arg
1               5

<210> SEQ ID NO 2
<211> LENGTH: 13
<212> TYPE: PRT
<213> ORGANISM: Unknown
<220> FEATURE:
<223> OTHER INFORMATION: Mammalian Peptide

<400> SEQUENCE: 2

Gly Arg Lys Lys Arg Arg Gln Arg Arg Arg Pro Pro Gln
1               5                   10

<210> SEQ ID NO 3
<211> LENGTH: 8
<212> TYPE: PRT
<213> ORGANISM: Unknown
<220> FEATURE:
<223> OTHER INFORMATION: Mammalian Peptide

<400> SEQUENCE: 3

Arg Gln Arg Arg Lys Lys Arg Gly
1               5

<210> SEQ ID NO 4
<211> LENGTH: 8
<212> TYPE: PRT
<213> ORGANISM: Unknown
<220> FEATURE:
<223> OTHER INFORMATION: Mammalian Peptide

<400> SEQUENCE: 4

Gly Arg Lys Lys Arg Arg Gln Arg
1               5

<210> SEQ ID NO 5
<211> LENGTH: 12
<212> TYPE: PRT
<213> ORGANISM: Unknown
<220> FEATURE:
<223> OTHER INFORMATION: Mammalian Peptide

<400> SEQUENCE: 5

Ala Tyr Ala Arg Ala Ala Ala Arg Gln Ala Arg Ala
1               5                   10

<210> SEQ ID NO 6
<211> LENGTH: 34
<212> TYPE: PRT
<213> ORGANISM: Unknown
<220> FEATURE:
<223> OTHER INFORMATION: Mammalian Peptide

<400> SEQUENCE: 6

Asp Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Pro
            20                  25                  30

Val Glu

<210> SEQ ID NO 7
<211> LENGTH: 27
<212> TYPE: PRT
```

```
<213> ORGANISM: Unknown
<220> FEATURE:
<223> OTHER INFORMATION: Mammalian Peptide

<400> SEQUENCE: 7

Gly Trp Thr Leu Asn Ser Ala Gly Tyr Leu Leu Gly Leu Ile Asn Leu
1               5                   10                  15

Lys Ala Leu Ala Ala Leu Ala Lys Lys Ile Leu
            20                  25

<210> SEQ ID NO 8
<211> LENGTH: 12
<212> TYPE: PRT
<213> ORGANISM: Unknown
<220> FEATURE:
<223> OTHER INFORMATION: Mammalian Peptide

<400> SEQUENCE: 8

Pro Leu Ser Ser Ile Phe Ser Arg Ile Gly Asp Pro
1               5                   10

<210> SEQ ID NO 9
<211> LENGTH: 16
<212> TYPE: PRT
<213> ORGANISM: Unknown
<220> FEATURE:
<223> OTHER INFORMATION: Mammalian Peptide

<400> SEQUENCE: 9

Ala Ala Val Ala Leu Leu Pro Ala Val Leu Leu Ala Leu Leu Ala Pro
1               5                   10                  15

<210> SEQ ID NO 10
<211> LENGTH: 12
<212> TYPE: PRT
<213> ORGANISM: Unknown
<220> FEATURE:
<223> OTHER INFORMATION: Mammalian Peptide

<400> SEQUENCE: 10

Ala Ala Val Leu Leu Pro Val Leu Leu Ala Ala Pro
1               5                   10

<210> SEQ ID NO 11
<211> LENGTH: 15
<212> TYPE: PRT
<213> ORGANISM: Unknown
<220> FEATURE:
<223> OTHER INFORMATION: Mammalian Peptide

<400> SEQUENCE: 11

Val Thr Val Leu Ala Leu Gly Ala Leu Ala Gly Val Gly Val Gly
1               5                   10                  15

<210> SEQ ID NO 12
<211> LENGTH: 21
<212> TYPE: PRT
<213> ORGANISM: Unknown
<220> FEATURE:
<223> OTHER INFORMATION: Mammalian Peptide

<400> SEQUENCE: 12

Gly Ala Leu Phe Leu Gly Trp Leu Gly Ala Ala Gly Ser Thr Met Gly
1               5                   10                  15

Ala Trp Ser Gln Pro
            20
```

<210> SEQ ID NO 13
<211> LENGTH: 27
<212> TYPE: PRT
<213> ORGANISM: Unknown
<220> FEATURE:
<223> OTHER INFORMATION: Mammalian Peptide

<400> SEQUENCE: 13

Gly Trp Thr Leu Asn Ser Ala Gly Tyr Leu Leu Gly Leu Ile Asn Leu
1               5                   10                  15

Lys Ala Leu Ala Ala Leu Ala Lys Lys Ile Leu
            20                  25

<210> SEQ ID NO 14
<211> LENGTH: 18
<212> TYPE: PRT
<213> ORGANISM: Unknown
<220> FEATURE:
<223> OTHER INFORMATION: Mammalian Peptide

<400> SEQUENCE: 14

Lys Leu Ala Leu Lys Leu Ala Leu Lys Ala Leu Lys Ala Ala Leu Lys
1               5                   10                  15

Leu Ala

<210> SEQ ID NO 15
<211> LENGTH: 21
<212> TYPE: PRT
<213> ORGANISM: Unknown
<220> FEATURE:
<223> OTHER INFORMATION: Mammalian Peptide

<400> SEQUENCE: 15

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 16
<211> LENGTH: 14
<212> TYPE: PRT
<213> ORGANISM: Unknown
<220> FEATURE:
<223> OTHER INFORMATION: Mammalian Peptide

<400> SEQUENCE: 16

Lys Ala Phe Ala Lys Leu Ala Ala Arg Leu Tyr Arg Lys Ala
1               5                   10

<210> SEQ ID NO 17
<211> LENGTH: 14
<212> TYPE: PRT
<213> ORGANISM: Unknown
<220> FEATURE:
<223> OTHER INFORMATION: Mammalian Peptide

<400> SEQUENCE: 17

Lys Ala Phe Ala Lys Leu Ala Ala Arg Leu Tyr Arg Ala Ala
1               5                   10

<210> SEQ ID NO 18
<211> LENGTH: 14
<212> TYPE: PRT
<213> ORGANISM: Unknown

-continued

<220> FEATURE:
<223> OTHER INFORMATION: Mammalian Peptide

<400> SEQUENCE: 18

Ala Ala Phe Ala Lys Leu Ala Ala Arg Leu Tyr Arg Lys Ala
1               5                   10

<210> SEQ ID NO 19
<211> LENGTH: 14
<212> TYPE: PRT
<213> ORGANISM: Unknown
<220> FEATURE:
<223> OTHER INFORMATION: Mammalian Peptide

<400> SEQUENCE: 19

Lys Ala Phe Ala Ala Leu Ala Ala Arg Leu Tyr Arg Lys Ala
1               5                   10

<210> SEQ ID NO 20
<211> LENGTH: 16
<212> TYPE: PRT
<213> ORGANISM: Unknown
<220> FEATURE:
<223> OTHER INFORMATION: Mammalian Peptide

<400> SEQUENCE: 20

Lys Ala Phe Ala Lys Leu Ala Ala Arg Leu Tyr Arg Lys Ala Gly Cys
1               5                   10                  15

<210> SEQ ID NO 21
<211> LENGTH: 16
<212> TYPE: PRT
<213> ORGANISM: Unknown
<220> FEATURE:
<223> OTHER INFORMATION: Mammalian Peptide

<400> SEQUENCE: 21

Lys Ala Phe Ala Lys Leu Ala Ala Arg Leu Tyr Arg Ala Ala Gly Cys
1               5                   10                  15

<210> SEQ ID NO 22
<211> LENGTH: 16
<212> TYPE: PRT
<213> ORGANISM: Unknown
<220> FEATURE:
<223> OTHER INFORMATION: Mammalian Peptide

<400> SEQUENCE: 22

Ala Ala Phe Ala Lys Leu Ala Ala Arg Leu Tyr Arg Lys Ala Gly Cys
1               5                   10                  15

<210> SEQ ID NO 23
<211> LENGTH: 16
<212> TYPE: PRT
<213> ORGANISM: Unknown
<220> FEATURE:
<223> OTHER INFORMATION: Mammalian Peptide

<400> SEQUENCE: 23

Lys Ala Phe Ala Ala Leu Ala Ala Arg Leu Tyr Arg Lys Ala Gly Cys
1               5                   10                  15

<210> SEQ ID NO 24
<211> LENGTH: 16
<212> TYPE: PRT
<213> ORGANISM: Unknown
<220> FEATURE:

<223> OTHER INFORMATION: Mammalian Peptide

<400> SEQUENCE: 24

Lys Ala Phe Ala Lys Leu Ala Ala Gln Leu Tyr Arg Lys Ala Gly Cys
1               5                   10                  15

<210> SEQ ID NO 25
<211> LENGTH: 16
<212> TYPE: PRT
<213> ORGANISM: Unknown
<220> FEATURE:
<223> OTHER INFORMATION: Mammalian Peptide

<400> SEQUENCE: 25

Ala Gly Gly Gly Gly Tyr Gly Arg Lys Lys Arg Arg Gln Arg Arg Arg
1               5                   10                  15

<210> SEQ ID NO 26
<211> LENGTH: 11
<212> TYPE: PRT
<213> ORGANISM: Unknown
<220> FEATURE:
<223> OTHER INFORMATION: Mammalian Peptide

<400> SEQUENCE: 26

Tyr Ala Arg Ala Ala Ala Arg Gln Ala Arg Ala
1               5                   10

<210> SEQ ID NO 27
<211> LENGTH: 11
<212> TYPE: PRT
<213> ORGANISM: Unknown
<220> FEATURE:
<223> OTHER INFORMATION: Mammalian Peptide

<400> SEQUENCE: 27

Tyr Gly Arg Lys Lys Arg Arg Gln Arg Arg Arg
1               5                   10

<210> SEQ ID NO 28
<211> LENGTH: 14
<212> TYPE: PRT
<213> ORGANISM: Unknown
<220> FEATURE:
<223> OTHER INFORMATION: Mammalian Peptide

<400> SEQUENCE: 28

Trp Leu Arg Arg Ile Lys Ala Trp Leu Arg Arg Ile Lys Ala
1               5                   10

<210> SEQ ID NO 29
<211> LENGTH: 21
<212> TYPE: PRT
<213> ORGANISM: Unknown
<220> FEATURE:
<223> OTHER INFORMATION: Mammalian Peptide

<400> SEQUENCE: 29

Trp Leu Arg Arg Ile Lys Ala Trp Leu Arg Arg Ile Lys Ala Trp Leu
1               5                   10                  15

Arg Arg Ile Lys Ala
            20

<210> SEQ ID NO 30
<211> LENGTH: 12
<212> TYPE: PRT

<213> ORGANISM: Unknown
<220> FEATURE:
<223> OTHER INFORMATION: Mammalian Peptide

<400> SEQUENCE: 30

Phe Ala Lys Leu Ala Ala Arg Leu Tyr Arg Lys Ala
1               5                   10

<210> SEQ ID NO 31
<211> LENGTH: 14
<212> TYPE: PRT
<213> ORGANISM: Unknown
<220> FEATURE:
<223> OTHER INFORMATION: Mammalian Peptide

<400> SEQUENCE: 31

Lys Ala Phe Ala Ala Leu Ala Ala Arg Leu Tyr Arg Lys Ala
1               5                   10

<210> SEQ ID NO 32
<211> LENGTH: 14
<212> TYPE: PRT
<213> ORGANISM: Unknown
<220> FEATURE:
<223> OTHER INFORMATION: Mammalian Peptide

<400> SEQUENCE: 32

Lys Ala Phe Ala Lys Leu Ala Ala Arg Leu Tyr Arg Ala Ala
1               5                   10

<210> SEQ ID NO 33
<211> LENGTH: 13
<212> TYPE: PRT
<213> ORGANISM: Unknown
<220> FEATURE:
<223> OTHER INFORMATION: Mammalian Peptide

<400> SEQUENCE: 33

Lys Ala Phe Ala Lys Leu Ala Ala Arg Leu Tyr Arg Ala
1               5                   10

<210> SEQ ID NO 34
<211> LENGTH: 12
<212> TYPE: PRT
<213> ORGANISM: Unknown
<220> FEATURE:
<223> OTHER INFORMATION: Mammalian Peptide

<400> SEQUENCE: 34

Phe Ala Lys Leu Ala Ala Arg Leu Tyr Arg Ala Ala
1               5                   10

<210> SEQ ID NO 35
<211> LENGTH: 11
<212> TYPE: PRT
<213> ORGANISM: Unknown
<220> FEATURE:
<223> OTHER INFORMATION: Mammalian Peptide

<400> SEQUENCE: 35

Phe Ala Lys Leu Ala Ala Arg Leu Tyr Arg Ala
1               5                   10

<210> SEQ ID NO 36
<211> LENGTH: 22
<212> TYPE: PRT
<213> ORGANISM: Unknown

```
<220> FEATURE:
<223> OTHER INFORMATION: Mammalian Peptide

<400> SEQUENCE: 36

Tyr Ala Arg Ala Ala Ala Arg Gln Ala Arg Ala Lys Ala Leu Ala Arg
1               5                   10                  15
Gln Leu Gly Val Ala Ala
            20

<210> SEQ ID NO 37
<211> LENGTH: 22
<212> TYPE: PRT
<213> ORGANISM: Unknown
<220> FEATURE:
<223> OTHER INFORMATION: Mammalian Peptide

<400> SEQUENCE: 37

Tyr Gly Arg Lys Lys Arg Arg Gln Arg Arg Lys Ala Leu Ala Arg
1               5                   10                  15
Gln Leu Gly Val Ala Ala
            20

<210> SEQ ID NO 38
<211> LENGTH: 19
<212> TYPE: PRT
<213> ORGANISM: Unknown
<220> FEATURE:
<223> OTHER INFORMATION: Mammalian Pepitde

<400> SEQUENCE: 38

Arg Gln Arg Arg Lys Lys Arg Gly Lys Ala Leu Ala Arg Gln Leu Gly
1               5                   10                  15
Val Ala Ala

<210> SEQ ID NO 39
<211> LENGTH: 19
<212> TYPE: PRT
<213> ORGANISM: Unknown
<220> FEATURE:
<223> OTHER INFORMATION: Mammalian Peptide

<400> SEQUENCE: 39

Gly Arg Lys Lys Arg Arg Gln Arg Lys Ala Leu Ala Arg Gln Leu Gly
1               5                   10                  15
Val Ala Ala

<210> SEQ ID NO 40
<211> LENGTH: 25
<212> TYPE: PRT
<213> ORGANISM: Unknown
<220> FEATURE:
<223> OTHER INFORMATION: Mammalian Peptide

<400> SEQUENCE: 40

Trp Leu Arg Arg Ile Lys Ala Trp Leu Arg Arg Ile Lys Ala Lys Ala
1               5                   10                  15
Leu Ala Arg Gln Leu Gly Val Ala Ala
            20                  25

<210> SEQ ID NO 41
<211> LENGTH: 32
<212> TYPE: PRT
<213> ORGANISM: Unknown
<220> FEATURE:
```

<223> OTHER INFORMATION: Mammalian Peptide

<400> SEQUENCE: 41

Trp Leu Arg Arg Ile Lys Ala Trp Leu Arg Arg Ile Lys Ala Trp Leu
1               5                   10                  15
Arg Arg Ile Lys Ala Lys Ala Leu Ala Arg Gln Leu Gly Val Ala Ala
            20                  25                  30

<210> SEQ ID NO 42
<211> LENGTH: 24
<212> TYPE: PRT
<213> ORGANISM: Unknown
<220> FEATURE:
<223> OTHER INFORMATION: Mammalian Peptide

<400> SEQUENCE: 42

Tyr Ala Arg Ala Ala Ala Arg Gln Ala Arg Ala Lys Lys Lys Ala Leu
1               5                   10                  15
Ala Arg Gln Leu Gly Val Ala Ala
            20

<210> SEQ ID NO 43
<211> LENGTH: 24
<212> TYPE: PRT
<213> ORGANISM: Unknown
<220> FEATURE:
<223> OTHER INFORMATION: Mammalian Peptide

<400> SEQUENCE: 43

Tyr Gly Arg Lys Lys Arg Arg Gln Arg Arg Lys Lys Lys Ala Leu
1               5                   10                  15
Ala Arg Gln Leu Gly Val Ala Ala
            20

<210> SEQ ID NO 44
<211> LENGTH: 21
<212> TYPE: PRT
<213> ORGANISM: Unknown
<220> FEATURE:
<223> OTHER INFORMATION: Mammalian Peptide

<400> SEQUENCE: 44

Arg Gln Arg Arg Lys Lys Arg Gly Lys Lys Ala Leu Ala Arg Gln
1               5                   10                  15
Leu Gly Val Ala Ala
            20

<210> SEQ ID NO 45
<211> LENGTH: 21
<212> TYPE: PRT
<213> ORGANISM: Unknown
<220> FEATURE:
<223> OTHER INFORMATION: Mammalian Peptide

<400> SEQUENCE: 45

Gly Arg Lys Lys Arg Arg Gln Arg Lys Lys Lys Ala Leu Ala Arg Gln
1               5                   10                  15
Leu Gly Val Ala Ala
            20

<210> SEQ ID NO 46
<211> LENGTH: 27
<212> TYPE: PRT
<213> ORGANISM: Unknown

```
<220> FEATURE:
<223> OTHER INFORMATION: Mammalian Peptide

<400> SEQUENCE: 46

Trp Leu Arg Arg Ile Lys Ala Trp Leu Arg Arg Ile Lys Ala Lys Lys
1               5                   10                  15

Lys Ala Leu Ala Arg Gln Leu Gly Val Ala Ala
            20                  25

<210> SEQ ID NO 47
<211> LENGTH: 34
<212> TYPE: PRT
<213> ORGANISM: Unknown
<220> FEATURE:
<223> OTHER INFORMATION: Mammalian Peptide

<400> SEQUENCE: 47

Trp Leu Arg Arg Ile Lys Ala Trp Leu Arg Arg Ile Lys Ala Trp Leu
1               5                   10                  15

Arg Arg Ile Lys Ala Lys Lys Ala Leu Ala Arg Gln Leu Gly Val
            20                  25                  30

Ala Ala

<210> SEQ ID NO 48
<211> LENGTH: 23
<212> TYPE: PRT
<213> ORGANISM: Unknown
<220> FEATURE:
<223> OTHER INFORMATION: Mammalian Peptide

<400> SEQUENCE: 48

Lys Ala Phe Ala Lys Leu Ala Ala Arg Leu Tyr Arg Lys Ala Leu Ala
1               5                   10                  15

Arg Gln Leu Gly Val Ala Ala
            20

<210> SEQ ID NO 49
<211> LENGTH: 21
<212> TYPE: PRT
<213> ORGANISM: Unknown
<220> FEATURE:
<223> OTHER INFORMATION: Mammalian Peptide

<400> SEQUENCE: 49

Phe Ala Lys Leu Ala Ala Arg Leu Tyr Arg Lys Ala Leu Ala Arg Gln
1               5                   10                  15

Leu Gly Val Ala Ala
            20

<210> SEQ ID NO 50
<211> LENGTH: 23
<212> TYPE: PRT
<213> ORGANISM: Unknown
<220> FEATURE:
<223> OTHER INFORMATION: Mammalian Peptide

<400> SEQUENCE: 50

Lys Ala Phe Ala Lys Leu Ala Ala Arg Leu Tyr Arg Ala Ala Leu Ala
1               5                   10                  15

Arg Gln Leu Gly Val Ala Ala
            20

<210> SEQ ID NO 51
```

-continued

```
<211> LENGTH: 22
<212> TYPE: PRT
<213> ORGANISM: Unknown
<220> FEATURE:
<223> OTHER INFORMATION: Mammalian Peptide

<400> SEQUENCE: 51

Lys Ala Phe Ala Lys Leu Ala Ala Arg Leu Tyr Arg Ala Leu Ala Arg
1               5                   10                  15

Gln Leu Gly Val Ala Ala
            20

<210> SEQ ID NO 52
<211> LENGTH: 23
<212> TYPE: PRT
<213> ORGANISM: Unknown
<220> FEATURE:
<223> OTHER INFORMATION: Mammalian Peptide

<400> SEQUENCE: 52

Lys Ala Phe Ala Ala Leu Ala Ala Arg Leu Tyr Arg Ala Ala Leu Ala
1               5                   10                  15

Arg Gln Leu Gly Val Ala Ala
            20

<210> SEQ ID NO 53
<211> LENGTH: 21
<212> TYPE: PRT
<213> ORGANISM: Unknown
<220> FEATURE:
<223> OTHER INFORMATION: Mammalian Peptide

<400> SEQUENCE: 53

Phe Ala Lys Leu Ala Ala Arg Leu Tyr Arg Ala Ala Leu Ala Arg Gln
1               5                   10                  15

Leu Gly Val Ala Ala
            20

<210> SEQ ID NO 54
<211> LENGTH: 23
<212> TYPE: PRT
<213> ORGANISM: Unknown
<220> FEATURE:
<223> OTHER INFORMATION: Mammalian Peptide

<400> SEQUENCE: 54

Trp Leu Arg Arg Ile Lys Ala Trp Leu Arg Arg Ile Lys Ala Leu Asn
1               5                   10                  15

Arg Gln Leu Gly Val Ala Ala
            20

<210> SEQ ID NO 55
<211> LENGTH: 21
<212> TYPE: PRT
<213> ORGANISM: Unknown
<220> FEATURE:
<223> OTHER INFORMATION: Mammalian Peptide

<400> SEQUENCE: 55

Tyr Ala Arg Ala Ala Ala Arg Gln Ala Arg Ala Lys Ala Leu Asn Arg
1               5                   10                  15

Gln Leu Gly Val Ala
            20
```

```
<210> SEQ ID NO 56
<211> LENGTH: 23
<212> TYPE: PRT
<213> ORGANISM: Unknown
<220> FEATURE:
<223> OTHER INFORMATION: Mammalian Peptide

<400> SEQUENCE: 56

Lys Ala Phe Ala Lys Leu Ala Ala Arg Leu Tyr Arg Lys Ala Leu Asn
1               5                   10                  15

Arg Gln Leu Ala Val Ala Ala
            20

<210> SEQ ID NO 57
<211> LENGTH: 21
<212> TYPE: PRT
<213> ORGANISM: Unknown
<220> FEATURE:
<223> OTHER INFORMATION: Mammalian Peptide

<400> SEQUENCE: 57

Phe Ala Lys Leu Ala Ala Arg Leu Tyr Arg Lys Ala Leu Asn Arg Gln
1               5                   10                  15

Leu Ala Val Ala Ala
            20

<210> SEQ ID NO 58
<211> LENGTH: 23
<212> TYPE: PRT
<213> ORGANISM: Unknown
<220> FEATURE:
<223> OTHER INFORMATION: Mammalian Peptide

<400> SEQUENCE: 58

Lys Ala Phe Ala Lys Leu Ala Ala Arg Leu Tyr Arg Lys Ala Leu Asn
1               5                   10                  15

Arg Gln Leu Gly Val Ala Ala
            20

<210> SEQ ID NO 59
<211> LENGTH: 21
<212> TYPE: PRT
<213> ORGANISM: Unknown
<220> FEATURE:
<223> OTHER INFORMATION: Mammalian Peptide

<400> SEQUENCE: 59

Phe Ala Lys Leu Ala Ala Arg Leu Tyr Arg Lys Ala Leu Asn Arg Gln
1               5                   10                  15

Leu Gly Val Ala Ala
            20

<210> SEQ ID NO 60
<211> LENGTH: 11
<212> TYPE: PRT
<213> ORGANISM: Unknown
<220> FEATURE:
<223> OTHER INFORMATION: Mammalian Peptide

<400> SEQUENCE: 60

Lys Ala Leu Asn Arg Gln Leu Gly Val Ala Ala
1               5                   10

<210> SEQ ID NO 61
<211> LENGTH: 11
```

```
<212> TYPE: PRT
<213> ORGANISM: Unknown
<220> FEATURE:
<223> OTHER INFORMATION: Mammalian Peptide

<400> SEQUENCE: 61

Lys Ala Ala Asn Arg Gln Leu Gly Val Ala Ala
1               5                   10

<210> SEQ ID NO 62
<211> LENGTH: 11
<212> TYPE: PRT
<213> ORGANISM: Unknown
<220> FEATURE:
<223> OTHER INFORMATION: Mammalian Peptide

<400> SEQUENCE: 62

Lys Ala Leu Ala Arg Gln Leu Gly Val Ala Ala
1               5                   10

<210> SEQ ID NO 63
<211> LENGTH: 11
<212> TYPE: PRT
<213> ORGANISM: Unknown
<220> FEATURE:
<223> OTHER INFORMATION: Mammalian Peptide

<400> SEQUENCE: 63

Lys Ala Leu Asn Ala Gln Leu Gly Val Ala Ala
1               5                   10

<210> SEQ ID NO 64
<211> LENGTH: 11
<212> TYPE: PRT
<213> ORGANISM: Unknown
<220> FEATURE:
<223> OTHER INFORMATION: Mammalian Peptide

<400> SEQUENCE: 64

Lys Ala Leu Asn Arg Ala Leu Gly Val Ala Ala
1               5                   10

<210> SEQ ID NO 65
<211> LENGTH: 11
<212> TYPE: PRT
<213> ORGANISM: Unknown
<220> FEATURE:
<223> OTHER INFORMATION: Mammalian Peptide

<400> SEQUENCE: 65

Lys Ala Leu Asn Arg Gln Ala Gly Val Ala Ala
1               5                   10

<210> SEQ ID NO 66
<211> LENGTH: 11
<212> TYPE: PRT
<213> ORGANISM: Unknown
<220> FEATURE:
<223> OTHER INFORMATION: Mammalian Peptide

<400> SEQUENCE: 66

Lys Ala Leu Asn Arg Gln Leu Ala Val Ala Ala
1               5                   10

<210> SEQ ID NO 67
<211> LENGTH: 11
<212> TYPE: PRT
```

-continued

```
<213> ORGANISM: Unknown
<220> FEATURE:
<223> OTHER INFORMATION: Mammalian Peptide

<400> SEQUENCE: 67

Lys Ala Leu Asn Arg Gln Leu Gly Ala Ala Ala
1               5                   10

<210> SEQ ID NO 68
<211> LENGTH: 10
<212> TYPE: PRT
<213> ORGANISM: Unknown
<220> FEATURE:
<223> OTHER INFORMATION: Mammalian Peptide

<400> SEQUENCE: 68

Lys Ala Leu Asn Arg Gln Leu Gly Val Ala
1               5                   10

<210> SEQ ID NO 69
<211> LENGTH: 81
<212> TYPE: PRT
<213> ORGANISM: Unknown
<220> FEATURE:
<223> OTHER INFORMATION: Mammalian Peptide
<220> FEATURE:
<221> NAME/KEY: MISC_FEATURE
<222> LOCATION: (1)..(34)
<223> OTHER INFORMATION: May encompass 4 to 9 "Arg" residues, wherein
      residues from positions 5 to 9 may be absent and residues from
      positions 10-34 are absent
<220> FEATURE:
<221> NAME/KEY: MISC_FEATURE
<222> LOCATION: (1)..(34)
<223> OTHER INFORMATION: Residues 1 to 13 are Gly Arg Lys Lys Arg Arg
      Gln Arg Arg Arg Pro Pro Gln and residues 14-34 are absent
<220> FEATURE:
<221> NAME/KEY: MISC_FEATURE
<222> LOCATION: (1)..(34)
<223> OTHER INFORMATION: Residues 1 to 8 are Arg Gln Arg Arg Lys Lys Arg
      Gly and residues 9 to 34 are absent
<220> FEATURE:
<221> NAME/KEY: MISC_FEATURE
<222> LOCATION: (1)..(34)
<223> OTHER INFORMATION: Residues 1 to 8 are Gly Arg Lys Lys Arg Arg Gln
      Arg and residues 9 to 34 are absent
<220> FEATURE:
<221> NAME/KEY: MISC_FEATURE
<222> LOCATION: (1)..(34)
<223> OTHER INFORMATION: Residues 1 to 12 are Ala Tyr Ala Arg Ala Ala
      Ala Arg Gln Ala Arg Ala and residues 13 to 34 are absent
<220> FEATURE:
<221> NAME/KEY: MISC_FEATURE
<222> LOCATION: (1)..(34)
<223> OTHER INFORMATION: Residues 1 to 34 are Asp Ala Ala Thr Ala Thr
      Arg Gly Arg Ser Ala Ala Ser Arg Pro Thr Glu Arg Pro Arg Ala Pro
      Ala Arg Ser Ala Ser Arg Pro Arg Arg Pro Val Glu
<220> FEATURE:
<221> NAME/KEY: MISC_FEATURE
<222> LOCATION: (1)..(34)
<223> OTHER INFORMATION: Residues 1 to 27 are Gly Trp Thr Leu Asn Ser
      Ala Gly Tyr Leu Leu Gly Leu Ile Asn Leu Lys Ala Leu Ala Ala Leu
      Ala Lys Lys Ile Leu and residues 28 to 34 are absent
<220> FEATURE:
<221> NAME/KEY: MISC_FEATURE
<222> LOCATION: (1)..(34)
<223> OTHER INFORMATION: Residues 1 to 12 are Pro Leu Ser Ser Ile Phe
      Ser Arg Ile Gly Asp Pro and residues 13-34 are absent
<220> FEATURE:
<221> NAME/KEY: MISC_FEATURE
<222> LOCATION: (1)..(34)
<223> OTHER INFORMATION: Residues 1 to 16 are Ala Ala Val Ala Leu Leu
      Pro Ala Val Leu Leu Ala Leu Leu Ala Pro and residues 17 to 34 are
      absent
<220> FEATURE:
```

```
<221> NAME/KEY: MISC_FEATURE
<222> LOCATION: (1)..(34)
<223> OTHER INFORMATION: Residues 1 to 12 are Ala Ala Val Leu Leu Pro
      Val Leu Leu Ala Ala Pro and residues 13 to 34 are absent
<220> FEATURE:
<221> NAME/KEY: MISC_FEATURE
<222> LOCATION: (1)..(34)
<223> OTHER INFORMATION: Residues 1 to 15 are Val Thr Val Leu Ala Leu
      Gly Ala Leu Ala Gly Val Gly Val Gly and residues 16- 34 are absent
<220> FEATURE:
<221> NAME/KEY: MISC_FEATURE
<222> LOCATION: (1)..(34)
<223> OTHER INFORMATION: Residues 1 to 21 are Gly Ala Leu Phe Leu Gly
      Trp Leu Gly Ala Ala Gly Ser Thr Met Gly Ala Trp Ser Gln Pro and
      residues 22-34 are absent
<220> FEATURE:
<221> NAME/KEY: MISC_FEATURE
<222> LOCATION: (1)..(34)
<223> OTHER INFORMATION: Residues 1 to 27 are Gly Trp Thr Leu Asn Ser
      Ala Gly Tyr Leu Leu Gly Leu Ile Asn Leu Lys Ala Leu Ala Ala Leu
      Ala Lys Lys Ile Leu and residues 28 to 34 are absent
<220> FEATURE:
<221> NAME/KEY: MISC_FEATURE
<222> LOCATION: (1)..(34)
<223> OTHER INFORMATION: Residues 1 to 18 are Lys Leu Ala Leu Lys Leu
      Ala Leu Lys Ala Leu Lys Ala Ala Leu Lys Leu Ala and residues 19
      to 34 are absent
<220> FEATURE:
<221> NAME/KEY: MISC_FEATURE
<222> LOCATION: (1)..(34)
<223> OTHER INFORMATION: Residues 1 to 21 are Lys Glu Thr Trp Trp Glu
      Thr Trp Trp Thr Glu Trp Ser Gln Pro Lys Lys Lys Arg Lys Val and
      residues 22-34 are absent
<220> FEATURE:
<221> NAME/KEY: MISC_FEATURE
<222> LOCATION: (1)..(34)
<223> OTHER INFORMATION: Residues 1 to 14 are Lys Ala Phe Ala Lys Leu
      Ala Ala Arg Leu Tyr Arg Lys Ala and residues 15 to 34 are absent
<220> FEATURE:
<221> NAME/KEY: MISC_FEATURE
<222> LOCATION: (1)..(34)
<223> OTHER INFORMATION: Residues 1 to 14 are Lys Ala Phe Ala Lys Leu
      Ala Ala Arg Leu Tyr Arg Ala Ala and residues 15 to 34 are absent
<220> FEATURE:
<221> NAME/KEY: MISC_FEATURE
<222> LOCATION: (1)..(34)
<223> OTHER INFORMATION: Residues 1 to 14 are Ala Ala Phe Ala Lys Leu
      Ala Ala Arg Leu Tyr Arg Lys Ala and residues 15 to 34 are absent
<220> FEATURE:
<221> NAME/KEY: MISC_FEATURE
<222> LOCATION: (1)..(34)
<223> OTHER INFORMATION: Residues 1 to 14 are Lys Ala Phe Ala Ala Leu
      Ala Ala Arg Leu Tyr Arg Lys Ala and residues 15 to 34 are absent
<220> FEATURE:
<221> NAME/KEY: MISC_FEATURE
<222> LOCATION: (1)..(34)
<223> OTHER INFORMATION: Residues 1 to 16 are Lys Ala Phe Ala Lys Leu
      Ala Ala Arg Leu Tyr Arg Lys Ala Gly Cys and residues 17 to 34 are
      absent
<220> FEATURE:
<221> NAME/KEY: MISC_FEATURE
<222> LOCATION: (1)..(34)
<223> OTHER INFORMATION: Residues 1 to 16 are Lys Ala Phe Ala Lys Leu
      Ala Ala Arg Leu Tyr Arg Ala Ala Gly Cys and residues 17 to 34 are
      absent
<220> FEATURE:
<221> NAME/KEY: MISC_FEATURE
<222> LOCATION: (1)..(34)
<223> OTHER INFORMATION: Residues 1 to 16 are Ala Ala Phe Ala Lys Leu
      Ala Ala Arg Leu Tyr Arg Lys Ala Gly Cys and residues 17 to 34 are
      absent
<220> FEATURE:
<221> NAME/KEY: MISC_FEATURE
<222> LOCATION: (1)..(34)
<223> OTHER INFORMATION: Residues 1 to 16 are Lys Ala Phe Ala Ala Leu
      Ala Ala Arg Leu Tyr Arg Lys Ala Gly Cys and residues 17 to 34 are
      absent
<220> FEATURE:
<221> NAME/KEY: MISC_FEATURE
```

```
<222> LOCATION: (1)..(34)
<223> OTHER INFORMATION: Residues 1 to 16 are Lys Ala Phe Ala Lys Leu
      Ala Ala Gln Leu Tyr Arg Lys Ala Gly Cys and residues 17 to 34 are
      absent
<220> FEATURE:
<221> NAME/KEY: MISC_FEATURE
<222> LOCATION: (1)..(34)
<223> OTHER INFORMATION: Residues 1 to 16 are Ala Gly Gly Gly Gly Tyr
      Gly Arg Lys Lys Arg Arg Gln Arg Arg Arg and residues 17 to 34 are
      absent
<220> FEATURE:
<221> NAME/KEY: MISC_FEATURE
<222> LOCATION: (1)..(34)
<223> OTHER INFORMATION: Residues 1 to 11 are Tyr Ala Arg Ala Ala Ala
      Arg Gln Ala Arg Ala and residues 12 to 34 are absent
<220> FEATURE:
<221> NAME/KEY: MISC_FEATURE
<222> LOCATION: (1)..(34)
<223> OTHER INFORMATION: Residues 1 to 11 are Tyr Gly Arg Lys Lys Arg
      Arg Gln Arg Arg Arg and residues 12 to 34 are absent
<220> FEATURE:
<221> NAME/KEY: MISC_FEATURE
<222> LOCATION: (1)..(34)
<223> OTHER INFORMATION: Residues 1 to 14 are Trp Leu Arg Arg Ile Lys
      Ala Trp Leu Arg Arg Ile Lys Ala and residues 15 to 34 are absent
<220> FEATURE:
<221> NAME/KEY: MISC_FEATURE
<222> LOCATION: (1)..(34)
<223> OTHER INFORMATION: Residues 1 to 21 are Trp Leu Arg Arg Ile Lys
      Ala Trp Leu Arg Arg Ile Lys Ala Trp Leu Arg Arg Ile Lys Ala and
      residues 22 to 34 are absent
<220> FEATURE:
<221> NAME/KEY: MISC_FEATURE
<222> LOCATION: (1)..(34)
<223> OTHER INFORMATION: Residues 1 to 12 are Phe Ala Lys Lue Ala Ala
      Arg Leu Tyr Arg Lys Ala and residues 13 to 34 are absent
<220> FEATURE:
<221> NAME/KEY: MISC_FEATURE
<222> LOCATION: (1)..(34)
<223> OTHER INFORMATION: Residues 1 to 14 are Lys Ala Phe Ala Ala Leu
      Ala Ala Arg Leu Tyr Arg Lys Ala and residues 15 to 34 are absent
<220> FEATURE:
<221> NAME/KEY: MISC_FEATURE
<222> LOCATION: (1)..(34)
<223> OTHER INFORMATION: Residues 1 to 14 are Lys Ala Phe Ala Lys Leu
      Ala Ala Arg Leu Tyr Arg Ala Ala and residues 15 to 34 are absent
<220> FEATURE:
<221> NAME/KEY: MISC_FEATURE
<222> LOCATION: (1)..(34)
<223> OTHER INFORMATION: Residues 1 to 13 are Lys Ala Phe Ala Lys Leu
      Ala Ala Arg Leu Tyr Arg Ala and residues 14 to 34 are absent
<220> FEATURE:
<221> NAME/KEY: MISC_FEATURE
<222> LOCATION: (1)..(34)
<223> OTHER INFORMATION: Residues 1 to 12 are Phe Ala Lys Leu Ala Ala
      Arg Leu Tyr Arg Ala Ala and residues 13 to 3t4 are absent
<220> FEATURE:
<221> NAME/KEY: MISC_FEATURE
<222> LOCATION: (1)..(34)
<223> OTHER INFORMATION: Residues 1 to 11 are Phe Ala Lys Leu Ala Ala
      Arg Leu Tyr Arg Ala and residues 12 to 34 are absent
<220> FEATURE:
<221> NAME/KEY: MISC_FEATURE
<222> LOCATION: (1)..(34)
<223> OTHER INFORMATION: Residues 1 to 34 are absent
<220> FEATURE:
<221> NAME/KEY: MISC_FEATURE
<222> LOCATION: (35)..(38)
<223> OTHER INFORMATION: Residues 35 is Ala and residues 36 to 38 are
      absent
<220> FEATURE:
<221> NAME/KEY: MISC_FEATURE
<222> LOCATION: (35)..(38)
<223> OTHER INFORMATION: Residues 35 to 38 are absent
<220> FEATURE:
<221> NAME/KEY: MISC_FEATURE
<222> LOCATION: (35)..(38)
<223> OTHER INFORMATION: Residues 35 to 36 are Lys Ala and residues 37
      to 38 are absent
```

```
<220> FEATURE:
<221> NAME/KEY: MISC_FEATURE
<222> LOCATION: (35)..(38)
<223> OTHER INFORMATION: Residues 35 to 37 are Lys Lys Ala and residue
      38 is absent
<220> FEATURE:
<221> NAME/KEY: MISC_FEATURE
<222> LOCATION: (35)..(38)
<223> OTHER INFORMATION: Residues 35 to 38 are Lys Lys Lys Ala
<220> FEATURE:
<221> NAME/KEY: MISC_FEATURE
<222> LOCATION: (35)..(38)
<223> OTHER INFORMATION: Residues 35 to 36 are Arg Ala and residues 37
      to 38 are absent
<220> FEATURE:
<221> NAME/KEY: MISC_FEATURE
<222> LOCATION: (39)..(39)
<223> OTHER INFORMATION: Residue 39 is Gly, Leu, Ala, Val, Ile, Met,
      Tyr, Trp, Phe or an aliphatic amino acid
<220> FEATURE:
<221> NAME/KEY: MISC_FEATURE
<222> LOCATION: (40)..(40)
<223> OTHER INFORMATION: Residue 40 is Val, Leu, Ile, Ala, Gly, Gln,
      Asn, Ser, Thr, Cys or an aliphaticamino acid
<220> FEATURE:
<221> NAME/KEY: MISC_FEATURE
<222> LOCATION: (41)..(41)
<223> OTHER INFORMATION: Residue 41 is Gln, Asn, His, Arg or Lys
<220> FEATURE:
<221> NAME/KEY: MISC_FEATURE
<222> LOCATION: (42)..(42)
<223> OTHER INFORMATION: Residue 42 is Gln or Asn
<220> FEATURE:
<221> NAME/KEY: MISC_FEATURE
<222> LOCATION: (43)..(43)
<223> OTHER INFORMATION: Residue 43 is Cys, Ala, Gly, Leu, Val, Ile,
      Met, Tyr, Trp, Phe or an aliphatic amino acid
<220> FEATURE:
<221> NAME/KEY: MISC_FEATURE
<222> LOCATION: (44)..(44)
<223> OTHER INFORMATION: Residue 44 is Ser, Ala, Cuys, Thr, Gly or an
      aliphatic amino acid
<220> FEATURE:
<221> NAME/KEY: MISC_FEATURE
<222> LOCATION: (45)..(45)
<223> OTHER INFORMATION: Residue 45 is Val, Leu, Ile or Met
<220> FEATURE:
<221> NAME/KEY: MISC_FEATURE
<222> LOCATION: (46)..(46)
<223> OTHER INFORMATION: Residue 46 is any amino acid or is absent
<220> FEATURE:
<221> NAME/KEY: MISC_FEATURE
<222> LOCATION: (47)..(47)
<223> OTHER INFORMATION: Residue 47 is any amino acid or is absent
<220> FEATURE:
<221> NAME/KEY: MISC_FEATURE
<222> LOCATION: (48)..(81)
<223> OTHER INFORMATION: May encompass 4 to 9 "Arg" residues, wherein
      residues from positions 52 to 56 may be absent and residues from
      positions 57 to 81 are absent
<220> FEATURE:
<221> NAME/KEY: MISC_FEATURE
<222> LOCATION: (48)..(81)
<223> OTHER INFORMATION: Residues 48 to 60 are Gly Arg Lys Lys Arg Arg
      Gln Arg Arg Arg Pro Pro Gln and residues 61 to 81 are absent
<220> FEATURE:
<221> NAME/KEY: MISC_FEATURE
<222> LOCATION: (48)..(81)
<223> OTHER INFORMATION: Residues 48 to 55 are Arg Gln Arg Arg Lys Lys
      Arg Gly and residues 56 to 81 are absent
<220> FEATURE:
<221> NAME/KEY: MISC_FEATURE
<222> LOCATION: (48)..(81)
<223> OTHER INFORMATION: Residues 48 to 55 are Gly Arg Lys Lsy Arg Arg
      Gln Arg and residues 56 to 81 are absent
<220> FEATURE:
<221> NAME/KEY: MISC_FEATURE
<222> LOCATION: (48)..(81)
<223> OTHER INFORMATION: Residues 48 to 59 are Ala Tyr Ala Arg Ala Ala
```

```
        Ala Arg Gln Ala Arg Ala and residues 60 to 81 are absent
<220> FEATURE:
<221> NAME/KEY: MISC_FEATURE
<222> LOCATION: (48)..(81)
<223> OTHER INFORMATION: Residues 48 to 81 are Asp Ala Ala Thr Ala Thr
      Arg Gly Arg Ser Ala Ala Ser Arg Pro Thr Glu Arg Pro Arg Ala Pro
      Ala Arg Ser Ala Ser Arg Pro Arg Arg Pro Val Glu
<220> FEATURE:
<221> NAME/KEY: MISC_FEATURE
<222> LOCATION: (48)..(81)
<223> OTHER INFORMATION: Residues 48 to 74 are Gly Trp Thr Leu Asn Ser
      Ala Gly Tyr Leu Leu Gly Leu Ile Asn Leu Lys Ala Leu Ala Ala Leu
      Ala Lys Lys Ile Leu and residues 75 to 81 are absent
<220> FEATURE:
<221> NAME/KEY: MISC_FEATURE
<222> LOCATION: (48)..(81)
<223> OTHER INFORMATION: Residues 48 to 59 are Pro Leu Ser Ser Ile Phe
      Ser Arg Ile Gly Asp Pro and residues 60 to 81 are absent
<220> FEATURE:
<221> NAME/KEY: MISC_FEATURE
<222> LOCATION: (48)..(81)
<223> OTHER INFORMATION: Residues 48 to 63 are Ala Ala Val Ala Leu Leu
      Pro Ala Val Leu Leu Ala Leu Leu Ala Pro and residues 64 to 81 are
      absent
<220> FEATURE:
<221> NAME/KEY: MISC_FEATURE
<222> LOCATION: (48)..(81)
<223> OTHER INFORMATION: Residues 48 to 59 are Ala Ala Val Leu Leu Pro
      Val Leu Leu Ala Ala Pro and residues 60 to 81 are absent
<220> FEATURE:
<221> NAME/KEY: MISC_FEATURE
<222> LOCATION: (48)..(81)
<223> OTHER INFORMATION: Residues 48 to 62 are Val Thr Val Leu Ala Leu
      Gly Ala Leu Ala Gly Val Gly Val Gly and residues 63 to 81 are
      absent
<220> FEATURE:
<221> NAME/KEY: MISC_FEATURE
<222> LOCATION: (48)..(81)
<223> OTHER INFORMATION: Residues 48 to 68 are Gly Ala Leu Phe Leu Gly
      Trp Leu Gly Ala Ala Gly Ser Thr Met Gly Ala Trp Ser Gln Pro and
      residues 69 to 81 are absent
<220> FEATURE:
<221> NAME/KEY: MISC_FEATURE
<222> LOCATION: (48)..(81)
<223> OTHER INFORMATION: Residues 48 to 74 are Gly Trp Thr Leu Asn Ser
      Ala Gly Tyr Leu Leu Gly Leu Ile Asn Leu Lys Ala Leu Ala Ala Leu
      Ala Lys Lys Ile Leu and residues 75 to 81 are absent
<220> FEATURE:
<221> NAME/KEY: MISC_FEATURE
<222> LOCATION: (48)..(81)
<223> OTHER INFORMATION: Residues 48 to 65 are Lys Leu Ala Leu Lys Leu
      Ala Leu Lys Ala Leu Lys Ala Ala Leu Lys Leu Ala and residues 66
      to 81 are absent
<220> FEATURE:
<221> NAME/KEY: MISC_FEATURE
<222> LOCATION: (48)..(81)
<223> OTHER INFORMATION: Residues 48 to 68 are Lys Glu Thr Trp Trp Glu
      Thr Trp Trp Thr Glu Trp Ser Gln Pro Lys Lys Lys Arg Lys Val  and
      residues 69 to 81 are absent
<220> FEATURE:
<221> NAME/KEY: MISC_FEATURE
<222> LOCATION: (48)..(81)
<223> OTHER INFORMATION: Residues 48 to 61 are Lys Ala Phe Ala Lys Leu
      Ala Ala Arg Leu Tyr Arg Lys Ala and residues 62 to 81 are absent
<220> FEATURE:
<221> NAME/KEY: MISC_FEATURE
<222> LOCATION: (48)..(81)
<223> OTHER INFORMATION: Residues 48 to 61 are Lys Ala Phe Ala Lys Leu
      Ala Ala Arg Leu Tyr Arg Ala Ala and residues 62 to 81 are absent
<220> FEATURE:
<221> NAME/KEY: MISC_FEATURE
<222> LOCATION: (48)..(81)
<223> OTHER INFORMATION: Residues 48 to 61 are Ala Ala Phe Ala Lys Leu
      Ala Ala Arg Leu Tyr Arg Lys Ala and residues 62 to 81 are absent
<220> FEATURE:
<221> NAME/KEY: MISC_FEATURE
<222> LOCATION: (48)..(81)
<223> OTHER INFORMATION: Residues 48 to 61 are Lys Ala Phe Ala Ala Leu
      Ala Ala Arg Leu Tyr Arg Lys Ala and residues 62 to 81 are absent
```

-continued

```
<220> FEATURE:
<221> NAME/KEY: MISC_FEATURE
<222> LOCATION: (48)..(81)
<223> OTHER INFORMATION: Residues 48 to 63 are Lys Ala Phe Ala Lys Leu
      Ala Ala Arg Leu Tyr Arg Lys Ala Gly Cys and residues 64 to 81 are
      absent
<220> FEATURE:
<221> NAME/KEY: MISC_FEATURE
<222> LOCATION: (48)..(81)
<223> OTHER INFORMATION: Residues 48 to 63 are Lys Ala Phe Ala Lys Leu
      Ala Ala Arg Leu Tyr Arg Ala Ala Gly Cys and residues 64 to 81 are
      absent
<220> FEATURE:
<221> NAME/KEY: MISC_FEATURE
<222> LOCATION: (48)..(81)
<223> OTHER INFORMATION: Residues 48 to 63 are Ala Ala Phe Ala Lys Leu
      Ala Ala Arg Leu Tyr Arg Lys Ala Gly Cys and residues 64 to 81 are
      absent
<220> FEATURE:
<221> NAME/KEY: MISC_FEATURE
<222> LOCATION: (48)..(81)
<223> OTHER INFORMATION: Residues 48 to 63 are Lys Ala Phe Ala Ala Leu
      Ala Ala Arg Leu Tyr Arg Lys Ala Gly Cys and residues 64 to 81 are
      absent
<220> FEATURE:
<221> NAME/KEY: MISC_FEATURE
<222> LOCATION: (48)..(81)
<223> OTHER INFORMATION: Residues 48 to 63 are Lys Ala Phe Ala Lys Leu
      Ala Ala Gln Leu Tyr Arg Lys Ala Gly Cys and residues 64 to 81 are
      absent
<220> FEATURE:
<221> NAME/KEY: MISC_FEATURE
<222> LOCATION: (48)..(81)
<223> OTHER INFORMATION: Residues 48 to 63 are Ala Gly Gly Gly Gly Tyr
      Gly Arg Lys Lys Arg Arg Gln Arg Arg Arg and residues 64 to 81 are
      absent
<220> FEATURE:
<221> NAME/KEY: MISC_FEATURE
<222> LOCATION: (48)..(81)
<223> OTHER INFORMATION: Residues 48 to 58 are Tyr Ala Arg Ala Ala Ala
      Arg Gln Ala Arg Ala and residues 59 to 81 are absent
<220> FEATURE:
<221> NAME/KEY: MISC_FEATURE
<222> LOCATION: (48)..(81)
<223> OTHER INFORMATION: Residues 48 to 58 are Tyr Gly Arg Lys Lys Arg
      Arg Gln Arg Arg Arg and residues 59 to 81 are absent
<220> FEATURE:
<221> NAME/KEY: MISC_FEATURE
<222> LOCATION: (48)..(81)
<223> OTHER INFORMATION: Residues 48 to 61 are Trp Leu Arg Arg Ile Lys
      Ala Trp Leu Arg Arg Ile Lys Ala and residues 62 to 81 are absent
<220> FEATURE:
<221> NAME/KEY: MISC_FEATURE
<222> LOCATION: (48)..(81)
<223> OTHER INFORMATION: Residues 48 to 68 are Trp Leu Arg Arg Ile Lys
      Ala Trp Leu Arg Arg Ile Lys Ala Trp Leu Arg Arg Ile Lys Ala and
      residues 69 to 81 are absent
<220> FEATURE:
<221> NAME/KEY: MISC_FEATURE
<222> LOCATION: (48)..(81)
<223> OTHER INFORMATION: Residues 48 to 59 are Phe Ala Lys Leu Ala Ala
      Arg Leu Tyr Arg Lys Ala and residues 60 to 81 are absent
<220> FEATURE:
<221> NAME/KEY: MISC_FEATURE
<222> LOCATION: (48)..(81)
<223> OTHER INFORMATION: Residues 48 to 61 are Lys Ala Phe Ala Ala Leu
      Ala Ala Arg Leu Tyr Arg Lys Ala and residues 62 to 81 are absent
<220> FEATURE:
<221> NAME/KEY: MISC_FEATURE
<222> LOCATION: (48)..(81)
<223> OTHER INFORMATION: Residues 48 to 61 are Lys Ala Phe Ala Lys Leu
      Ala Ala Arg Leu Tyr Arg Ala Ala and residues 62 to 81 are absent
<220> FEATURE:
<221> NAME/KEY: MISC_FEATURE
<222> LOCATION: (48)..(81)
<223> OTHER INFORMATION: Residues 48 to 60 are Lys Ala Phe Ala Lys Leu
      Ala Ala Arg Leu Tyr Arg Ala and residues 61 to 81 are absent
<220> FEATURE:
<221> NAME/KEY: MISC_FEATURE
```

```
<222> LOCATION: (48)..(81)
<223> OTHER INFORMATION: Residues 48 to 59 are Phe Ala Lys Leu Ala Ala
      Arg Leu Tyr Arg Ala Ala and residues 60 to 81 are absent
<220> FEATURE:
<221> NAME/KEY: MISC_FEATURE
<222> LOCATION: (48)..(81)
<223> OTHER INFORMATION: Residues 48 to 58 are Phe Ala Lys Leu Ala Ala
      Arg Leu Tyr Arg Ala and residues 59 to 81 are absent
<220> FEATURE:
<221> NAME/KEY: MISC_FEATURE
<222> LOCATION: (48)..(81)
<223> OTHER INFORMATION: Residues 48 to 81 are absent

<400> SEQUENCE: 69

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa

<210> SEQ ID NO 70
<211> LENGTH: 4
<212> TYPE: PRT
<213> ORGANISM: Unknown
<220> FEATURE:
<223> OTHER INFORMATION: Mammalian Peptide

<400> SEQUENCE: 70

Lys Lys Lys Ala
1

<210> SEQ ID NO 71
<211> LENGTH: 11
<212> TYPE: PRT
<213> ORGANISM: Unknown
<220> FEATURE:
<223> OTHER INFORMATION: Mammalian Peptide
<220> FEATURE:
<221> NAME/KEY: MISC_FEATURE
<222> LOCATION: (3)..(3)
<223> OTHER INFORMATION: D-Amino Acid

<400> SEQUENCE: 71

Lys Ala Leu Asn Arg Gln Leu Gly Val Ala Ala
1               5                   10

<210> SEQ ID NO 72
<211> LENGTH: 13
<212> TYPE: PRT
<213> ORGANISM: Unknown
<220> FEATURE:
<223> OTHER INFORMATION: Mammalian Peptide

<400> SEQUENCE: 72

Lys Lys Lys Ala Leu Asn Arg Gln Leu Gly Val Ala Ala
1               5                   10

<210> SEQ ID NO 73
<211> LENGTH: 4
<212> TYPE: PRT
```

```
<213> ORGANISM: Unknown
<220> FEATURE:
<223> OTHER INFORMATION: Mammalian Peptide

<400> SEQUENCE: 73

Tyr Ala Arg Ala
1

<210> SEQ ID NO 74
<211> LENGTH: 11
<212> TYPE: PRT
<213> ORGANISM: Unknown
<220> FEATURE:
<223> OTHER INFORMATION: Mammalian Peptide
<220> FEATURE:
<221> NAME/KEY: MISC_FEATURE
<222> LOCATION: (6)..(6)
<223> OTHER INFORMATION: D-Amino Acid

<400> SEQUENCE: 74

Lys Ala Leu Asn Arg Gln Leu Gly Val Ala Ala
1               5                   10

<210> SEQ ID NO 75
<211> LENGTH: 11
<212> TYPE: PRT
<213> ORGANISM: Unknown
<220> FEATURE:
<223> OTHER INFORMATION: Mammalian Peptide
<220> FEATURE:
<221> NAME/KEY: MISC_FEATURE
<222> LOCATION: (7)..(7)
<223> OTHER INFORMATION: D-Amino Acid

<400> SEQUENCE: 75

Lys Ala Leu Asn Arg Gln Leu Gly Val Ala Ala
1               5                   10

<210> SEQ ID NO 76
<211> LENGTH: 11
<212> TYPE: PRT
<213> ORGANISM: Unknown
<220> FEATURE:
<223> OTHER INFORMATION: Mammalian Peptide
<220> FEATURE:
<221> NAME/KEY: MISC_FEATURE
<222> LOCATION: (9)..(9)
<223> OTHER INFORMATION: D-Amino Acid

<400> SEQUENCE: 76

Lys Ala Leu Asn Arg Gln Leu Gly Val Ala Ala
1               5                   10

<210> SEQ ID NO 77
<211> LENGTH: 11
<212> TYPE: PRT
<213> ORGANISM: Unknown
<220> FEATURE:
<223> OTHER INFORMATION: Mammalian Peptide
<220> FEATURE:
<221> NAME/KEY: MISC_FEATURE
<222> LOCATION: (4)..(4)
<223> OTHER INFORMATION: D-Amino Acid

<400> SEQUENCE: 77

Lys Ala Leu Asn Arg Gln Leu Gly Val Ala Ala
1               5                   10

<210> SEQ ID NO 78
```

```
<211> LENGTH: 11
<212> TYPE: PRT
<213> ORGANISM: Unknown
<220> FEATURE:
<223> OTHER INFORMATION: Mammalian Peptide
<220> FEATURE:
<221> NAME/KEY: MISC_FEATURE
<222> LOCATION: (5)..(5)
<223> OTHER INFORMATION: D-Amino Acid

<400> SEQUENCE: 78

Lys Ala Leu Asn Arg Gln Leu Gly Val Ala Ala
1               5                   10
```